US012735672B2

(12) United States Patent
De Bruijn et al.

(10) Patent No.: US 12,735,672 B2
(45) Date of Patent: Sep. 15, 2026

(54) ***SACCHAROMYCES* YEAST CELL AND FERMENTATION PROCESS USING SUCH**

(71) Applicant: DANISCO US INC., Palo Alto, CA (US)

(72) Inventors: Hans Marinus Charles Johannes De Bruijn, Echt (NL); Phillip E. Bureman, Echt (NL); Evert Tjeerd Van Rij, Echt (NL); René Marcel De Jong, Echt (NL)

(73) Assignee: DANISCO US INC., Palo Alto, CA (US)

( * ) Notice: Subject to any disclaimer, the term of this patent is extended or adjusted under 35 U.S.C. 154(b) by 485 days.

(21) Appl. No.: 18/030,026

(22) PCT Filed: Oct. 5, 2021

(86) PCT No.: PCT/EP2021/077334
§ 371 (c)(1),
(2) Date: Apr. 3, 2023

(87) PCT Pub. No.: WO2022/073952
PCT Pub. Date: Apr. 14, 2022

(65) Prior Publication Data

US 2023/0374443 A1 Nov. 23, 2023

Related U.S. Application Data

(60) Provisional application No. 63/087,642, filed on Oct. 5, 2020.

(51) Int. Cl.

| | |
|---|---|
| ***C12N 1/185*** | (2026.01) |
| ***C12N 9/06*** | (2006.01) |
| ***C12P 7/06*** | (2006.01) |
| ***C12R 1/865*** | (2006.01) |

(52) U.S. Cl.
CPC ........... *C12N 1/185* (2021.05); *C12N 9/0044* (2013.01); *C12P 7/06* (2013.01); *C12R 2001/865* (2021.05)

(58) Field of Classification Search
CPC ........ C12N 1/185; C12N 9/0044; C12N 1/18; C12N 15/52; C12P 7/06; C12R 2001/865; Y02E 50/10; C07K 14/245
See application file for complete search history.

(56) References Cited

U.S. PATENT DOCUMENTS

| | | | | |
|---|---|---|---|---|
| 7,589,257 | B2 * | 9/2009 | Hershey | C07K 14/415 800/278 |
| 8,343,764 | B2 * | 1/2013 | Abad | C12N 15/8241 800/298 |
| 8,541,208 | B1 * | 9/2013 | Plesch | C07K 14/245 435/106 |
| 9,234,223 | B2 * | 1/2016 | Yamazaki | C12N 9/88 |
| 10,604,772 | B2 * | 3/2020 | Argyros | C12N 9/0008 |
| 2025/0283121 | A1 * | 9/2025 | Vugt-Van Lutz | C12P 7/06 |

FOREIGN PATENT DOCUMENTS

| | | |
|---|---|---|
| WO | 2013/076144 A2 | 5/2013 |
| WO | 2020/209718 A1 | 10/2020 |

OTHER PUBLICATIONS

Banerjee et al., Improving enzymes for biomass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Ingledew, W. M., et al. "Yeast Foods and Ethyl Carbamate Formation in Wine" American Journal of Enology and Viticulture, vol. 38, No. 4, pp. 332-335, Jan. 1987.
International Search Report and Written Opinion issued Jan. 4, 2022 in International Patent Application No. PCT/EP2021/077334 (12 pages).
Linder, Tomas. "Nitrogen Assimilation Pathways in Budding Yeasts", In: Sibirny, A. (eds) Non-conventional Yeasts: from Basic Research to Application, Chapter 7. Springer, Cham. Aug. 2019.
Nissen, Torben L., et al. "Anaerobic and aerobic batch cultivations of *Saccharomyces cerevisiae* mutants impaired in glycerol synthesis" Yeast, vol. 16, No. 5, pp. 463-474, Mar. 2000.
Siverio, Jose M. "Assimilation of Nitrate by Yeasts" FEMS Microbiology Reviews, vol. 26, pp. 277-284, Aug. 2002.

(Continued)

*Primary Examiner* — Ganapathirama Raghu

(57) ABSTRACT

A *Saccharomyces* yeast cell, preferably a *Saccharomyces cerevisae* yeast cell, comprising one or more nucleic acid sequences encoding an enzyme having NADH-dependent nitrate reductase activity and/or one or more nucleic acid sequences encoding an enzyme having NADH-dependent nitrite reductase activity. An anaerobic fermentation process for the production of a fermentation product using such *Saccharomyces* yeast cell and a fermentation co-product produced.

20 Claims, 1 Drawing Sheet

Specification includes a Sequence Listing.

(56) References Cited

OTHER PUBLICATIONS

Truong, Hoai-Nam, et al. "Characteristics of Nicotiana tabacum nitrate reductase protein produced in *Saccharomyces cerevisiae*" Biochem Journal, vol. 278, pp. 393-397, Sep. 1991.
Yao, Linxing, et al. "Quantitative Analysis of Ethyl Carbamate in Distillers Grains Co-products and Bovine Plasma by Gas Chromatography—Mass Spectrometry" Journal of Agricultural and Food Chemistry, vol. 68, pp. 10984-10991, Sep. 2020.

* cited by examiner

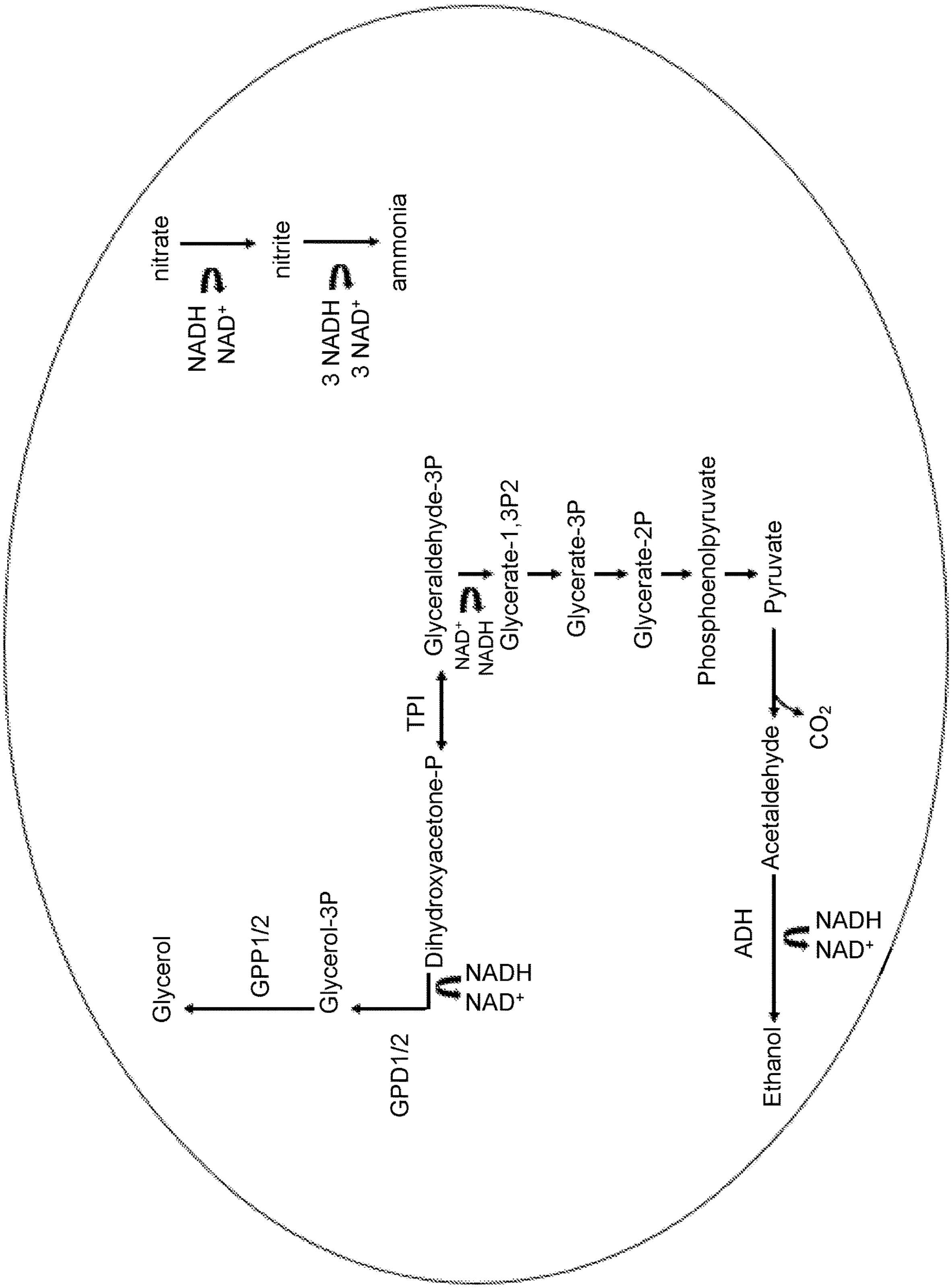
nitrate
NADH
NAD+
nitrite
3 NADH
3 NAD+
ammonia
Glyceraldehyde-3P
NAD+
NADH
Glycerate-1,3P2
Glycerate-3P
Glycerate-2P
Phosphoenolpyruvate
Pyruvate
$CO_2$
Acetaldehyde
ADH
NADH
NAD+
Ethanol
TPI
Dihydroxyacetone-P
NADH
NAD+
GPD1/2
Glycerol-3P
GPP1/2
Glycerol

*SACCHAROMYCES* YEAST CELL AND FERMENTATION PROCESS USING SUCH

CROSS-REFERENCE TO RELATED APPLICATIONS

This application is the National Stage entry of International Application No. PCT/EP2021/077334, filed 5 Oct. 2021, which claims priority to U.S. Patent Application No. 63/087,642, filed 5 Oct. 2020. The entire contents of each of which are hereby incorporated by reference for all purposes.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-600000_ST25" created on Apr. 3, 2023, and 97,842 bytes in size) is submitted concurrently with the instant application, and the entire contents of the Sequence Listing are incorporated herein by reference.

BACKGROUND

Field

The invention relates to a yeast cell having the ability to produce a desired fermentation product and to a process for producing a fermentation product wherein said yeast cell is used.

Description of Related Art

Yeast-based fermentation processes are applied for industrial production of a broad and rapidly expanding range of chemical compounds from conventional and renewable carbohydrate feedstocks.

Especially in anaerobic fermentation processes, redox balancing of the cofactor couple NADH/$NAD^+$ can cause important challenges for product yields. For example, a major challenge relating to the stoichiometry of yeast-based ethanol production is that substantial amounts of glycerol are invariably formed as a byproduct. It has been estimated that, in typical industrial ethanol processes, up to about 4 wt. % of the sugar feedstock is converted into glycerol (Nissen et al. Yeast 16 (2000) 463-474).

Glycerol production under anaerobic conditions is primarily linked to the redox balancing mechanisms in the yeast cell. During anaerobic growth of *S. cerevisiae*, sugar dissimilation occurs via so-called alcoholic fermentation. In this process, the NADH formed via the NAD+-dependent glycolytic glyceraldehyde-3-phosphate dehydrogenase reaction is reoxidized by converting acetaldehyde, formed by decarboxylation of pyruvate, to ethanol via NADH-dependent alcohol dehydrogenase. The fixed stoichiometry of this redox-neutral dissimilatory pathway causes problems when a net reduction of NAD+ to NADH occurs elsewhere in the metabolism. Under anaerobic conditions, in this situation, NADH reoxidation in *S. cerevisiae* is strictly dependent on reduction of sugar to glycerol. Glycerol formation is initiated by reduction of the glycolytic intermediate dihydroxyacetone phosphate (DHAP) to glycerol 3-phosphate (glycerol-3P), a reaction catalyzed by NADH-dependent glycerol 3-phosphate dehydrogenase. Subsequently, the glycerol 3-phosphate formed in this reaction is hydrolysed by glycerol-3-phosphatase to yield glycerol. Consequently, glycerol is a major by-product during anaerobic production of ethanol by *S. cerevisiae*. The production of glycerol is undesired as it reduces overall conversion of sugar to a desired fermentation product such as ethanol. Further, the presence of glycerol in effluents of fermentation plants may impose costs for waste-water treatment.

Nitrogen is a key nutrient for yeast cells. As described by Linder in his chapter 7 on Nitrogen Assimilation Pathways in Budding Yeasts, in the handbook "*Non-conventional Yeasts: from Basic Research to Application*", edited by Sibirney, published by Springer Nature Switzerland AG (2019) pages 197 and following, ammonia (NH3) is one of the simplest nitrogen substrates used as a nitrogen source by budding yeasts.

According to Linder, the vast majority of biosynthetic pathways for nitrogen-containing biomolecules in yeast first require ammonia to be converted into L-glutamate and L-glutamine, which are then used as amino group donors in downstream anabolic transamination reactions. The enzyme NADP+-dependent glutamate dehydrogenase (EC 1.4.1.4; encoded by the GDH1 gene) catalyzes the amination of α-ketoglutarate to form I-glutamate, while the enzyme glutamine synthetase (EC 6.3.1.2; encoded by the GLN1 gene) catalyzes the amination of I-glutamate to form I-glutamine. A second copy of the GDH1 gene (termed GDH3) has been described in *S. cerevisiae* and appears to play a distinct physiological role in nitrogen metabolism.

According to Linder, the ability to assimilate inorganic nitrogen sources other than ammonia is thought to be rare among budding yeasts. Nitrate ($NO_3^-$) is said to be assimilated by a two-step reduction via nitrite ($NO_2^-$) to produce ammonia. The reduction of nitrate into nitrite is said to be carried out by the enzyme nitrate reductase (EC 1.7.1.2/EC 1.7.1.3), which is encoded by the YNR1 gene. Linder indicates that in addition to the presence of flavin adenine dinucleotide (FAD) and heme prosthetic groups, nitrate reductase is one of the few enzymes currently known in budding yeasts that require the molybdenum cofactor (MoCo) for its activity. Linder explains that the redox cofactor requirements for yeast nitrate reductase appear to differ between species. The nitrate reductase in *Blastobotrys adeninivorans* (family Trichomonascaceae) is thought specific for NADPH, while the nitrate reductases of *Candida boidinii* (family Pichiaceae), *Cyberlindnera jadinii* (family Phaffomycetaceae), and *Ogataea polymorpha* (family Pichiaceae) are thought to be able to use both NADH and NADPH. Nitrite is said to be further reduced to ammonia by the FAD-containing enzyme nitrite reductase (EC 1.7.1.4), which is encoded by the YNI1 gene. The redox cofactor specificity for budding yeast nitrite reductases is indicated by Linder to have not been studied in a comprehensive manner.

Also in the article by Siverio, titled "*Assimilation of nitrate by yeasts*", published in FEMS Microbiology Reviews vol. 26 (2002) pages 277-284, it is mentioned that yeasts are able to use a great variety of compounds as nitrogen sources. However, the use of nitrate and nitrite is restricted to relatively few species of different genera. It is mentioned that yeasts of the genera *Saccharomyces* and *Schizosaccharomyces* are unable to use nitrate or nitrite as sole nitrogen source. The yeast studied by Siverio, *Hansenula polymorpha*, now renamed as *Pichia angusta*, was found to do comprise nitrate-reductase activity.

As indicated by Linder above, ammonia is a preferred nitrogen source for yeast cultivation. Urea can be a cheap source of ammonia. Urea can be easily broken down into two molecules of ammonium ion and one molecule of carbon dioxide. However, as indicated by Ingledew et al, in their article titled "*Yeast foods and ethyl carbamate formation in wine*", published in the American Journal of Enology and Viticulture, (1987), vol. 38, pages 332-335, many countries have now banned the use of urea as a yeast food ingredient for potable alcohol manufacturing because it leads to the production of small amounts of urethane (ethyl carbamate) which is a suspected carcinogen in foods. Yoa et al, in their article titled "*Quantitative Analysis of Ethyl Carbamate in Distillers Grains Coproducts and Bovine Plasma by Gas Chromatography-Mass Spectrometry*", published in the J. Agric. Food Chem. (2020), vol. 68, 10984-10991 have developed a gas chromatography-mass spectrometry assay to quantify ethyl carbamate (abbreviated as EC, mentioned to be a Group 2A probable human carcinogen) extracted from various distillers grains co-products and found that corn condensed distillers solubles contained the highest concentration of ethyl carbamate, ranging from 1618 to 2956 ng/g. Concentrations of ethyl carbamate in other types of distillers grains co-products varied from 17 to 917 ng/g. Cattle fed distillers grains coproducts that constituted 19-38% of the total feed (as-fed) were found to contain 2-3 ng/mL of ethyl carbamate in blood plasma.

WO2013/076144A2 describes a recombinant microorganism engineered for the production of 2,3-butanediol (BDO). The patent publication describes that 2,3-butanediol is a by-product of alcoholic fermentation by yeast and usually one of the most abundant minor constituent of wine. It is indicated that numerous attempts have been made to engineer *Saccharomyces cerevisiae* strains with reduced acetoin yields, by re-orienting carbons toward glycerol and 2,3-BDO to obtain low-alcohol yeasts with desirable organoleptic features, permitting the decrease of the ethanol contents in wines. WO2013076144A2 is related to a recombinant microorganism engineered to produce 2,3-butanediol (BDO) wherein said microorganism is chosen among bacterium or yeast and overexpresses at least one gene encoding a polypeptide involved in the conversion of pyruvate into 2,3-butanediol. Six different metabolic pathways are exemplified applying NADH-dependent butanediol dehydrogenase and/or NADH-dependent acetoin dehydrogenase.

In WO2013/076144A2 a number of optimizations of 2,3-butanediol production are described. In passing, as an example, it is mentioned that NADH-dependant glyceraldehyde-3-phosphate dehydrogenase can be replaced by an NADPH-dependant enzyme. It is noted that in this specific case the BDO producing organism will produce an excess of NADPH. It is mentioned that this NADPH in turn can be used via assimilatory nitrate reduction, requiring the introduction of nitrate reductase into certain yeast strains that lack this enzyme.

It would be an advancement in the art to provide a novel yeast cell, which is suitable for an anaerobic fermentation process for the production of a fermentation product, such as ethanol, which has a reduced glycerol production compared to its corresponding wild-type organism or which lacks glycerol production if the cell is used for the fermentative preparation of ethanol.

It would further be an advancement in the art to provide a novel yeast cell, the use of which leads to less contamination with lactic acid bacteria in an anaerobic fermentation process. Without wishing to be bound by any kind of theory, it is thought that contamination by lactic acid bacteria can reduce ethanol yield during fermentation of starch-based feedstocks by *Saccharomyces* yeast cells.

It would further be an advancement in the art to provide a novel yeast cell, which—when used in an anaerobic fermentation process—leads to the production of a commercially interesting yield of distillers grains co-products containing a reduced amount of ethylcarbamate and/or an otherwise improved quality as compared to distillers grains co-products obtained with its wild-type counterpart.

SUMMARY

Accordingly this invention provides a *Saccharomyces* yeast cell, preferably a *Saccharomyces cerevisae* yeast cell, comprising one or more nucleic acid sequences encoding an enzyme having NADH-dependent nitrate reductase activity and/or one or more nucleic acid sequences encoding an enzyme having NADH-dependent nitrite reductase activity.

Preferably such *Saccharomyces* yeast cell further comprises one or more nucleic acid sequences encoding an enzyme having nitrate and/or nitrite transporter activity.

Further, such *Saccharomyces* yeast cell may preferably comprise flavin adenine dinucleotide (FAD), one or more heme prosthetic groups, and/or a molybdenum cofactor (MoCo) and/or one or more nucleic acid sequences encoding a flavin adenine dinucleotide (FAD), one or more heme prosthetic groups, and/or a molybdenum cofactor (MoCo).

Preferably the *Saccharomyces* yeast cell is a transgenic, recombinant and/or genetically modified *Saccharomyces* yeast cell. In such case, the above nucleic acid sequences are preferably nucleic acid sequences that are heterologous to the host cell that is used to construe such transgenic, recombinant and/or genetically modified *Saccharomyces* yeast cell.

Advantageously the *Saccharomyces* yeast cell, when used in a fermentation process, may produce less ethyl carbamate compared to corresponding wild-type cells.

Advantageously the *Saccharomyces* yeast cell, when used in a fermentation process, may produce less glycerol compared to corresponding wild-type cells. Preferably the *Saccharomyces* yeast cells may either be free of glycerol phosphate phosphatase activity or have reduced glycerol phosphate phosphatase activity compared to corresponding wild-type cells. More preferably the *Saccharomyces* yeast cells may comprise a genomic mutation in at least one gene selected from the group consisting of GPD1, GPD2, GPP1 and GPP2, preferably a deletion of one or more genes selected from the group consisting of GPD1, GPD2, GPP1 and GPP2.

Preferably the *Saccharomyces* yeast cell may further comprise:

- one or more nucleic acid sequences encoding a glycerol dehydrogenase; and/or
- one or more nucleic acid sequences encoding a dihydroxyacetone kinase; and/or
- one or more nucleic acid sequences encoding a glycerol transporter.

In addition the invention provides an anaerobic fermentation process for the production of a fermentation product, comprising fermenting of a feed, which feed comprises an oxidized nitrogen source and a fermentable carbon source, using a *Saccharomyces* yeast cell as described herein.

Preferably the fermentable carbon source comprises or consists of one or more monosaccharides, disaccharides and/or polysaccharides, such as starch. Preferably the oxidized nitrogen source comprises or consists of:

- an acid, salt or ion of nitrate; and/or
- an acid, salt or ion of nitrite.

Conveniently the oxidized nitrogen source may be part of a composition comprising nitrate and/or nitrite in combination with one or more other nitrogen sources selected from the group consisting of ammonium, ammonia and urea.

Advantageously a fermentation product may be produced selected from the group consisting of ethanol, n-butanol, isobutanol, lactic acid, 3-hydroxy-propionic acid, acrylic acid, acetic acid, succinic acid, fumaric acid, malic acid, itaconic acid, maleic acid, citric acid, adipic acid.

In addition a fermentation co-product may be produced, which fermentation co-product preferably comprises or consists of distillers grains, such as for example distillers wet grains and/or distillers dried grains, with or without solubles. Such fermentation co-product, such as such distillers grains, may advantageously comprise equal to or less than 17 ng/g of ethyl carbamate.

The invention further provides a product comprising distillers grains, obtained or obtainable by a fermentation process as described herein. In addition, the invention provides a product comprising distillers grains comprising equal to or less than 17 ng/g of ethyl carbamate. Such distillers grains may comprise or consist of distillers wet grains and/or distillers dried grains, with or without solubles.

The invention further provide a use of a fermentation co-product as described herein in an animal feed and/or in a fertilizer.

The *Saccharomyces* yeast cell according to the invention has in particular been found advantageous in that glycerol production and/or ethyl carbamate production may be considerably reduced or essentially eliminated and production of desired products, for example ethanol, may be increased. The invention allows one to increase the cytosolic NADH level in the *Saccharomyces* yeast cell. For example, in an ethanol fermentation process, this can advantageously lead to an improved yield of ethanol and/or a reduction in the formation of glycerol. These advantages are further detailed herein below.

In addition, the invention allows the *Saccharomyces* yeast cell to have an advantage over contaminants such as lactic acid bacteria, when fermentation is carried out with a feed or medium comprising an oxidized nitrogen source. Due to the capability of the *Saccharomyces* yeast cell to convert the oxidized nitrogen source, whereas the lactic acid bacteria may not have this capability or may have this capability to a lesser extent, the risk that the lactic acid bacteria reach a critical concentration is reduced.

BRIEF DESCRIPTION OF THE SEQUENCE LISTING

This application contains a Sequence Listing in computer readable form, which is incorporated herein by reference. An overview is provided by Table 1 below:

TABLE 1

Overview of sequence listings:

| SEQ ID NO: | Enzyme Name | Organism | Type |
|---|---|---|---|
| SEQ ID NO: 1 | NR1 nitrate reductase [Uniprot accession no: Q9XGW5] | *Zea mays* | Protein (amino acid sequenc) |
| SEQ ID NO: 2 | NIA Nitrate reductase [Uniprot accession no: P23312] | *Spinacia oleracea* | Protein |
| SEQ ID NO: 3 | nirD Nitrite reductase (small subunit) | *Escherichia coli* | Protein |
| SEQ ID NO: 4 | nirB Nitite reductase (large subunit) | *Escherichia coli* | Protein |
| SEQ ID NO: 5 | niiA Nitrite reductase | *Emericella nidulans* (*Aspergillus nidulans*) | Protein |
| SEQ ID NO: 6 | YNT1 Nitrate/Nitrite transporter | *Pichia angusta* (*Hansenula polymorpha*) | Protein |
| SEQ ID NO: 7 | MoaA_ECOLI GTP 3',8-cyclase | *Escherichia coli* | Protein |
| SEQ ID NO: 8 | MoaC_ECOLI Cyclic pyranopterin monophosphate synthase | *Escherichia coli* | Protein |
| SEQ ID NO: 9 | MoaD_ECOLI Molybdopterin synthase sulfur carrier subunit | *Escherichia coli* | Protein |
| SEQ ID NO: 10 | MoaE_ECOLI Molybdopterin synthase catalytic subunit | *Escherichia coli* | Protein |
| SEQ ID NO: 11 | MobA_ECOLI Molybdenum cofactor guanylyltransferase | *Escherichia coli* | Protein |
| SEQ ID NO: 12 | MobB_ECOLI Molybdopterin-guanine dinucleotide biosynthesis adapter protein | *Escherichia coli* | Protein |
| SEQ ID NO: 13 | MocA_ECOLI Molybdenum cofactor cytidylyltransferase | *Escherichia coli* | Protein |
| SEQ ID NO: 14 | ModA_ECOLI Molybdate-binding protein ModA | *Escherichia coli* | Protein |
| SEQ ID NO: 15 | ModB_BPT4 NAD--protein ADP-ribosyltransferase modB | Enterobacteria phage T4 | Protein |
| SEQ ID NO: 16 | ModC_ECOLI Molybdenum import ATP-binding protein ModC | *Escherichia coli* | Protein |
| SEQ ID NO: 17 | ModE_ECOLI DNA-binding transcriptional dual regulator ModE | *Escherichia coli* | Protein |
| SEQ ID NO: 18 | MoeA_ECOLI Molybdopterin molybdenumtransferase | *Escherichia coli* | Protein |
| SEQ ID NO: 19 | MoeB_ECOLI Molybdopterin-synthase adenylyltransferase | *Escherichia coli* | Protein |
| SEQ ID NO: 20 | MogA_ECOLI Molybdopterin adenylyltransferase | *Escherichia coli* | Protein |
| SEQ ID NO: 21 | IscS_ECOLI Cysteine desulfurase IscS | *Escherichia coli* | Protein |
| SEQ ID NO: 22 | Siroheme synthase CysG | *Escherichia coli* | Protein |

TABLE 1-continued

| Overview of sequence listings: | | | |
|---|---|---|---|
| SEQ ID NO: | Enzyme Name | Organism | Type |
| SEQ ID NO: 23 | MET8_YEAST Siroheme biosynthesis protein | *Saccharomyces cerevisiae* | Protein |
| SEQ ID NO: 24 | CNX1_ARATH Molybdopterin biosynthesis protein | *Arabidopsis thaliana* | Protein |
| SEQ ID NO: 25 | CNX2_ARATH GTP 3',8-cyclase, mitochondrial | *Arabidopsis thaliana* | Protein |
| SEQ ID NO: 26 | CNX3_ARATH Cyclic pyranopterin monophosphate synthase, mitochondrial | *Arabidopsis thaliana* | Protein |
| SEQ ID NO: 27 | MOCS3_ARATH Adenylyltransferase and sulfurtransferase MOCS3 | *Arabidopsis thaliana* | Protein |
| SEQ ID NO: 28 | MOC2B_ARATH Molybdopterin synthase catalytic subunit | *Arabidopsis thaliana* | Protein |
| SEQ ID NO: 29 | MOC2A_ARATH Molybdopterin synthase sulfur carrier subunit | *Arabidopsis thaliana* | Protein |

In the context of this patent application, each of the above protein/amino acid sequences is preferably encoded by a DNA/nucleic acid sequence that is codon-pair optimized for expression in *S. cerevisiae*. In order to reach an optimal expression one or more promoters may be added. Promoters may be regulated from strong to weak and may include one or more of TDH3, FBA1, ENO2, PGK1, TEF1, HTA1, HHF2, RPL8A, CHO1, RPS3, EFT2, HTA2, ACT1, PFY1, CUP1, ZUO1, VMA6 and/or ANB1, HEM13, YHK8, FET4, TIR4, AAC3.

BRIEF DESCRIPTION OF THE DRAWINGS

FIG. 1 provides an overview of the metabolic pathways involved in the yeast cell.

DETAILED DESCRIPTION OF A PREFERRED EMBODIMENT

Unless defined otherwise or clearly indicated by context, all technical and scientific terms used herein have the same meaning as commonly understood by one of ordinary skill in the art.

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element. When referring to a noun (e.g. a compound, an additive, etc.) in the singular, the plural is meant to be included. Thus, when referring to a specific moiety, e.g. "gene", this means "at least one" of that gene, e.g. "at least one gene", unless specified otherwise.

When referring to a compound of which several isomers exist (e.g. a D and an L enantiomer), the compound in principle includes all enantiomers, diastereomers and cis/trans isomers of that compound that may be used in the particular aspect of the invention; in particular when referring to such as compound, it includes the natural isomer(s).

The term "carbon source" refers to a source of carbon, preferably a compound or molecule comprising carbon. Preferably the carbon source is a carbohydrate. A carbohydrate is understood herein to be an organic compound made of carbon, oxygen and hydrogen. Suitably the carbon source may be selected from the group consisting of mono-, di- and/or polysaccharides, polyols, acids and acid salts. More preferably the carbon source is a compound selected from the group of glucose, arabinose, xylose, galactose, mannose, rhamnose, fructose, glycerol and acetic acid or a salt thereof.

The term "ferment", and variations thereof such as "fermenting", "fermentation" and/or "fermentative", is used herein in a classical sense, i.e. to indicate that a process is or has been carried out under anaerobic conditions. An anaerobic fermentation is herein defined to be a fermentation carried out under anaerobic conditions. Anaerobic conditions are herein defined as conditions without any oxygen or in which essentially no oxygen is consumed by the yeast cell. Conditions in which essentially no oxygen is consumed suitably corresponds to an oxygen consumption of less than 5 mmol/l.$h^{-1}$, in particular to an oxygen consumption of less than 2.5 mmol/l.$h^{-1}$, or less than 1 mmol/l.$h^{-1}$. More preferably 0 mmol/L/h is consumed (i.e. oxygen consumption is not detectable). This suitably corresponds to a dissolved oxygen concentration in a culture broth of less than 5% of air saturation, more suitably to a dissolved oxygen concentration of less than 1% of air saturation, or less than 0.2% of air saturation.

The term "cell" refers to a eukaryotic or prokaryotic organism, preferably occurring as a single cell. In the present invention the cell is a yeast cell. That is, the recombinant cell is selected from the group of genera consisting of yeast.

The terms "yeast" and "yeast cell" are used herein interchangeably and refer to a phylogenetically diverse group of single-celled fungi, most of which are in the division of Ascomycota and Basidiomycota. The budding yeasts ("true yeasts") are classified in the order Saccharomycetales. The yeast cell according to the invention is a *Saccharomyces* yeast cell and is defined as a yeast cell derived from the genus of *Saccharomyces*. Preferably the yeast cell is a yeast cell of the species *Saccharomyces cerevisiae*.

The term "recombinant", for example referring to a "recombinant yeast", a "recombinant cell", "recombinant micro-organism" and/or "recombinant strain" as used herein, refers to a yeast, cell, micro-organism or strain, respectively, containing nucleic acid which is the result of one or more genetic modifications. Simply put the yeast, cell, micro-organism or strain contains a different combination of nucleic acid from (either of) its parent(s). To construe a recombinant yeast, cell, micro-organism or strain recombinant DNA technique(s) and/or another mutagenic technique(s) can be used. In particular a recombinant yeast and/or a recombinant yeast cell may comprise nucleic acid not present in the corresponding wild-type yeast and/or cell, which nucleic acid has been introduced into that yeast and/or yeast cell using recombinant DNA techniques (i.e. a transgenic yeast and/or cell), or which nucleic acid not present in said wild-type yeast and/or cell is the result of one or more mutations—for example using recombinant DNA techniques or another mutagenesis technique such as UV-irradiation—in a nucleic acid sequence present in said wild-type yeast and/or yeast cell (such as a gene encoding a wild-type polypeptide) or wherein the nucleic acid sequence of a gene has been modified to target the polypeptide product (encoding it) towards another cellular compartment. Further, the term "recombinant" may suitably relate to a yeast, cell, micro-organism or strain from which nucleic acid sequences have been removed, for example using recombinant DNA techniques.

By a recombinant yeast comprising or having a certain activity is herein understood that the recombinant yeast may comprise one or more nucleic acid sequences encoding for an enzyme having such activity. Hence allowing the recombinant yeast to functionally express such a protein.

The term "transgenic" as used herein, for example referring to a "transgenic yeast" and/or a "transgenic cell", refers to a yeast and/or cell, respectively, containing nucleic acid not naturally occurring in that yeast and/or cell and which has been introduced into that yeast and/or cell using recombinant DNA techniques, such as a recombinant yeast and/or cell.

The term "mutated" as used herein regarding proteins or polypeptides means that at least one amino acid in the wild-type or naturally occurring protein or polypeptide sequence has been replaced with a different amino acid, inserted or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning-A Laboratory Manual, 2nd ed., Vol. 1-3 (1989). The term "mutated" as used herein regarding genes means that at least one nucleotide in the nucleic acid sequence of that gene or a regulatory sequence thereof, has been replaced with a different nucleotide, or has been deleted from the sequence via mutagenesis, resulting in the transcription of a protein sequence with a qualitatively of quantitatively altered function or the knock-out of that gene. In the context of this invention an "altered gene" has the same meaning as a mutated gene.

The term "gen" or "gene", as used herein, refers to a nucleic acid sequence that can be transcribed into mRNAs that are then translated into protein. A gene encoding for a certain protein refers to the one or more nucleic acid sequence(s) encoding for such a protein.

The term "nucleic acid" as used herein, refers to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

When an enzyme is mentioned with reference to an enzyme class (EC), the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at chem.qmul.ac.uk/iubmb/enzyme/. Other suitable enzymes that have not (yet) been classified in a specified class but may be classified as such, are meant to be included.

If referred herein to a protein or a nucleic acid sequence, such as a gene, by reference to a accession number, this number in particular is used to refer to a protein or nucleic acid sequence (gene) having a sequence as can be found via ncbi.nlm.nih.gov/, (as available on 1 Oct. 2020) unless specified otherwise.

Every nucleic acid sequence herein that encodes a polypeptide also includes any conservatively modified variants thereof. This includes that, by reference to the genetic code, it describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

Any exogenous gene coding for an enzyme herein comprises a nucleotide sequence coding for an amino acid sequence with at least 40, 50, 60, 65, 70, 75, 80, 85, 86, 87, 88, 89, 90, 91, 92, 93, 94, 95, 96, 97, 98, 99 or 100% amino acid sequence identity with any of SEQ ID's NO: X, wherein SEQ ID NO:X is any of the protein sequences in the sequence listing of this application. The exogenous gene coding for an enzyme may also comprises a nucleotide sequence coding for an amino acid sequence having one or several substitutions, insertions and/or deletions as compared to the amino acid sequence of any of SEQ ID NO: X. Preferably the amino acid sequence has no more than 300, 250, 200, 150, 100, 75, 50, 40, 30, 20, 10, 9, 8, 7, 6, 5, 4, 3, 2, or 1 amino acid substitutions, insertions and/or deletions as compared to SEQ ID's NO: X.

Any exogenous gene coding for an enzyme herein comprises a nucleotide sequence with at least 40, 50, 60, 65, 70, 75, 80, 85, 86, 87, 88, 89, 90, 95, 96, 97, 98, 99% or 100% nucleotide (DNA) sequence identity with any of SEQ ID's NO: Y, wherein SEQ ID NO: Y is any of the nucleotide (DNA) sequences in the sequence listing of this application.

The term "functional homologue" (or in short "homologue") of a polypeptide and/or amino acid sequence having a specific sequence (e.g. "SEQ ID NO: X"), as used herein, refers to a polypeptide and/or amino acid sequence comprising said specific sequence with the proviso that one or more amino acids are substituted, deleted, added, and/or inserted, and which polypeptide has (qualitatively) the same enzymatic functionality for substrate conversion. This functionality may be tested by use of an assay system comprising a recombinant cell comprising an expression vector for the expression of the homologue in yeast, said expression vector comprising a heterologous nucleic acid sequence operably linked to a promoter functional in the yeast and said heterologous nucleic acid sequence encoding the homologous polypeptide of which enzymatic activity for converting acetyl-Coenzyme A to acetaldehyde in the cell is to be tested, and assessing whether said conversion occurs in said cells. With respect to nucleic acid sequences, the term functional homologue is meant to include nucleic acid sequences which differ from another nucleic acid sequence due to the degeneracy of the genetic code and encode the same polypeptide sequence.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl/). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labeled in the output of the program as "longest-identity".

A variant of a nucleotide or amino acid sequence disclosed herein may also be defined as a nucleotide or amino acid sequence having one or several substitutions, insertions and/or deletions as compared to the nucleotide or amino acid sequence specifically disclosed herein (e.g. in de the sequence listing).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. In an embodiment, conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. In an embodiment, conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro;

His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Nucleotide sequences of the invention may also be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

"Expression" refers to the transcription of a gene into structural RNA (rRNA, tRNA) or messenger RNA (mRNA) with subsequent translation into a protein. "Overexpression" refers to expression of a gene by a recombinant cell in excess to its expression in a corresponding wild-type cell. Such overexpression can for example be arranged for by: increasing the frequency of transcription of one or more nucleic acid sequences, for example by operational linking of the nucleic acid sequence to a promoter functional within the recombinant cell; and/or by increasing the number of copies of a certain nucleic acid sequence.

Nucleic acid sequences (i.e. polynucleotides) or proteins (i.e. polypeptides) may be homologous or heterologous to the genome of the host cell.

"Homologous" with respect to a host cell, means that the nucleic acid sequence does naturally occur in the genome of the host cell or that the protein is naturally produced by that cell. Homologous protein expression may e.g. be an overexpression or expression under control of a different promoter. In the present inventions the host cell is a yeast.

The term "heterologous", with respect to the host cell, means that the polynucleotide does not naturally occur in the genome of the host cell or that the polypeptide is not naturally produced by that cell. Heterologous protein expression involves expression of a protein that is not naturally produced in the host cell. As used herein, "heterologous" may refer to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in eukaryotic host cell systems such as yeast are well known to those of skill in the art. A polynucleotide comprising a nucleic acid sequence of a gene encoding an enzyme with a specific activity can be expressed in such a eukaryotic system. In some embodiments, transformed/transfected cells may be employed as expression systems for the expression of the enzymes. Expression of heterologous proteins in yeast is well known. Sherman, F., et al., Methods in Yeast Genetics, Cold Spring Harbor Laboratory (1982) is a well-recognized work describing the various methods available to express proteins in yeast. Two widely utilized yeasts are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

As used herein "promoter" is a DNA sequence that directs the transcription of a (structural) gene. Typically, a promoter is located in the 5'-region of a gene, proximal to the transcriptional start site of a (structural) gene. Promoter sequences may be constitutive, inducible or repressible. In an embodiment there is no (external) inducer needed.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleic acid sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

By "host cell" is herein understood a cell, such as a yeast cell, that is to be transformed with one or more nucleic acid sequences encoding for one or more heterologous proteins, to construe a transformed cell, also referred to as a recombinant cell. For example, the transformed cell may contain a vector and may support the replication and/or expression of the vector.

"Transformation" and "transforming", as used herein, refers to the insertion of an exogenous polynucleotide (i.e. an exogenous nucleic acid sequence) into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

By "disruption" is herein understood any disruption of activity, including, but not limited to, deletion, mutation and reduction of the affinity of the disrupted gene and expression of RNA complementary to such disrupted gene. It includes all nucleic acid modifications such as nucleotide deletions or substitutions, gene knock-outs, and other actions which affect the translation or transcription of the corresponding polypeptide and/or which affect the enzymatic (specific) activity, its substrate specificity, and/or or stability. It also includes modifications that may be targeted on the coding sequence or on the promotor of the gene. A gene disruptant is a cell that has one or more disruptions of the respective gene. Native to yeast herein is understood as that the gene is present in the yeast cell before the disruption.

The term "encoding" has the same meaning as "coding for". Thus, by way of example, "one or more genes encoding a glycerol dehydrogenase" has the same meaning as "one or more genes coding for a glycerol dehydrogenase". As far as genes encoding an enzyme are concerned, the phrase "one or more genes encoding a X", wherein X denotes an enzyme, has the same meaning as "one or more genes encoding an enzyme having X activity". Thus, by way of example, "one or more genes encoding a NADH-dependent nitrate reductase" has the same meaning as "one or more genes encoding an enzyme having NADH-dependent nitrate reductase activity"; and "one or more heterologous genes encoding a NADH-dependent nitrite reductase" has the same meaning as "one or more heterologous genes encoding an enzyme having NADH-dependent nitrite reductase activity".

The abbreviation "NADH" refers to reduced, hydrogenated form of nicotinamide adenine dinucleotide. The abbreviation "NAD+" refers to the oxidized form of nicotinamide adenine dinucleotide. Nicotinamide adenine dinucleotide may act as a so-called cofactor, assisting in biochemical reactions and/or transformations in a cell.

"NADH dependent" is herein equivalent to NADH specific and "NADH dependency" is herein equivalent to NADH specificity.

By a NADH-dependent enzyme is herein understood an enzyme that is exclusively depended on NADH as a cofactor or that is predominantly dependent on NADH as a cofactor. By an "exclusive NADH-dependent" enzyme is herein understood an enzyme that has an absolute requirement for NADH over NADPH. That is, it is only active when NADH is applied as cofactor. By a "predominantly NADH-dependent" enzyme is herein understood an enzyme that has a higher specificity and/or a higher catalytic efficiency for NADH as a cofactor than for NADPH as a cofactor.

The enzyme's specificity characteristics can be described by the formula:

$$1<K_m\ NADP^+/K_m NAD^+<\infty\text{(infinity)}$$

wherein $K_m$ is the so-called Michaelis constant.

For a predominantly NADH-dependent enzyme, preferably $K_m NADP^+/K_m NAD^+$ is between 1 and 1000, between 1 and 500, between 1 and 200, between 1 and 100, between 1 and 50, between 1 and 10, between 5 and 100, between 5 and 50, between 5 and 20 or between 5 and 10. The $K_m$'s for the enzymes herein can be determined as enzyme specific, for $NAD^+$ and $NADP^+$ respectively, using know analysis techniques, calculations and protocols. These are described for instance in Lodish et al., Molecular Cell Biology 6$^{th}$ Edition, Ed. Freeman, pages 80 and 81, e.g. FIG. 3-22.

For an predominantly NADH-dependent enzyme, preferably the ratio of the catalytic efficiency for NADPH/NADP+ as a cofactor $(k_{cat}/K_m)^{NADP+}$ to NADH/NAD+ as cofactor $(k_{cat}/K_m)^{NAD+}$, i.e. the catalytic efficiency ratio $(k_{cat}/K_m)^{NADP+}:(k_{cat}/K_m)^{NAD+}$, is more than 1:1, more preferably equal to or more than 2:1, still more preferably equal to or more than 5:1, even more preferably equal to or more than 10:1, yet even more preferably equal to or more than 20:1, even still more preferably equal to or more than 100:1, and most preferably equal to or more than 1000:1.

There is no upper limit, but for practical reasons the predominantly NADH-dependent enzyme may have a catalytic efficiency ratio $(k_{cat}/K_m)^{NADP+}:(k_{cat}/K_m)^{NAD+}$ of equal to or less than 1.000.000.000:1 (i.e. $1.10^9$:1).

The *Saccharomyces* Yeast Cell

The *Saccharomyces* yeast cell is preferably a yeast cell derived from a yeast cell of the species *Saccharomyces cerevisiae*, herein also referred to as a *Saccharomyces cerevisae* yeast cell.

In an alternative embodiment, the *Saccharomyces* yeast cell as described herein may be replaced with a *Schizosaccharomyces* yeast cell, for example a *Schizosaccharomyces pompe* yeast cell, and such *Schizosaccharomyces* yeast cell may be used instead.

Preferably the *Saccharomyces* yeast cell is an industrial yeast cell. The living environments of yeast cells in industrial processes are significantly different from that in the laboratory. Industrial yeast cells must be able to perform well under multiple environmental conditions which may vary during the process. Such variations include changes in nutrient sources, pH, ethanol concentration, temperature, oxygen concentration, etc., which together have potential impact on the cellular growth and ethanol production of the yeast cell. An industrial yeast cell can be understood to refer to a yeast cell that, when compared to a laboratory counterpart, has a more robust performance. That is, when compared to a laboratory counterpart, the industrial yeast cell shows less variation in performance when one or more environmental conditions selected from the group of nutrient sources, pH, ethanol concentration, temperature, oxygen concentration, are varied during fermentation. Preferably, the *Saccharomyces* yeast cell is constructed on the basis of an industrial *Saccharomyces* yeast cell as a host, wherein the construction is conducted as described hereinafter.

Examples of industrial *Saccharomyces* yeast cells are Ethanol Red® (Fermentis) Fermiol® (DSM) and Thermosacc® (Lallemand).

The *Saccharomyces* yeast cell comprises one or more genes encoding a NADH-dependent nitrate reductase and/or one or more genes encoding a NADH-dependent nitrite reductase. In addition, the *Saccharomyces* yeast cell described herein may comprise one or more genes encoding a nitrate and/or nitrite transporter and optionally one or more genes encoding further enzymes.

The *Saccharomyces* yeast cell described herein may be derived from any host cell capable of producing a fermentation product. Preferably the *Saccharomyces* yeast cell described herein is derived from a host cell having the ability to produce ethanol. Preferably the host cell is a *Saccharomyces* yeast cell, more preferably an industrial *Saccharomyces* yeast cell as described herein above.

The *Saccharomyces* yeast cell described herein may be derived from the host cell through any technique known by one skilled in the art to be suitable for incorporation of the desired genes. Such techniques may include any one or more of mutagenesis, recombinant DNA technology (including, but not limited to, CRISPR-CAS techniques), selective and/or adaptive evolution, mating, cell fusion, and/or cytoduction between yeast strains. Suitably the one or more genes encoding a NADH-dependent nitrate reductase and/or the one or more genes encoding a NADH-dependent nitrite reductase and/or any further genes are incorporated in the *Saccharomyces* yeast cell by a combination of one or more of the above techniques.

Nitrate Reductase

Nitrate reductase (NR) catalyzes the reduction of nitrate ($NO_3^-$) to nitrite ($NO_2^-$). Nitrite reductase catalyzes the reduction of nitrite to ammonia ($NH_3$). Nitrate reductase and/or nitrite reductase can be part of a so-called nitrogen assimilation pathway in certain cells. Cells comprising nitrate reductase activity and/or nitrite reductase activity include certain plant cells and bacterial cells and a few yeast cells. As indicated by Linder, the ability to assimilate inorganic nitrogen sources other than ammonia is thought to be rare among budding yeasts. Among the few fungi that are naturally capable to assimilate nitrate or nitrite are *Blastobotrys adeninivorans* (family Trichomonascaceae) *Candida boidinii* (family Pichiaceae), *Cyberlindnera jadinii* (family Phaffomycetaceae), and *Ogataea polymorpha* (family Pichiaceae).

Preferably the *Saccharomyces* yeast cell as described herein comprises at least one or more genes encoding a NADH-dependent nitrate reductase.

By a NADH-dependent nitrate reductase is herein understood a nitrate reductase that is exclusively depended on NADH as a co-factor or that is predominantly dependent on NADH as a cofactor. Preferably the NADH-dependent nitrate reductase has a ratio of catalytic efficiency for NADPH/NADP+ as a cofactor $(k_{cat}/K_m)^{NADP+}$ to NADH/NAD+ as cofactor $(k_{cat}/K_m)^{NAD+}$, i.e. a catalytic efficiency ratio $(k_{cat}/K_m)^{NADP+}:(k_{cat}/K_m)^{NAD+}$, of more than 1:1, more preferably of equal to or more than 2:1, still more preferably of equal to or more than 5:1, even more preferably of equal to or more than 10:1, yet even more preferably of equal to or more than 20:1, even still more preferably of equal to or more than 100:1, and most preferably equal to or more than 1000:1. There is no upper limit, but for practical reasons the NADH-dependent nitrate reductase may have a catalytic efficiency ratio $(k_{cat}/K_m)^{NADP+}:(k_{cat}/K_m)^{NAD+}$ of equal to or less than 1.000.000.000:1 (i.e. $1.10^9$). Most preferably the NADH-dependent nitrate reductase is exclusively depended on NADH/NAD+ as a co-factor. That is, most preferably the NADH-dependent nitrate reductase has an absolute requirement for NADH/NAD+ as a cofactor instead of NADPH/NADP+ as a cofactor.

Preferably the NADH-dependent nitrate reductase is a NADH-dependent nitrate reductase with enzyme classification EC 1.7.1.1. (i.e. with EC number EC 1.7.1.1) or enzyme classification EC.1.6.6.1 (i.e. with EC number 1.6.6.1). Suitably the NADH-dependent nitrate reductase, also referred to as NADH-dependent nitrate oxidoreductase, is an enzyme that catalyzes at least the following chemical reaction:

$$nitrate+NADH+H^+\rightarrow nitrite+NAD^++H_2O$$

Suitable NADH-dependent nitrate reductases may include one or more NADH-dependent nitrate reductases as obtained or derived from *Agrostemma githago, Amaranthus hybridus, Amaranthus tricolor, Ankistrodesmus braunii, Arabidopsis thaliana, Aspergillus niger, Aspergillus nidulans, Auxenochlorella pyrenoidosa, Bradyrhizobium* sp., *Bradyrhizobium* sp. 750, *Brassica juncea, Brassica, oleracea, Camellia sinensis, Candida boidinii, Candida utilis, Capsicum frutescens, Chenopodium album, Cyberlindnera jadinii, Brassica juncea, Brassica oleracea, Camellia sinensis, Capsicum frutescens, Chenopodium album, Chlamydomonas reinhardtii, Chlorella fusca, Chlorella* sp. *Chlorella* sp. Berlin, *Chlorella vulgaris, Conticribra weissflogii, Cucumis sativus, Cucurbita maxima, Cucurbita pepo, Cucurbita* sp., *Dunaliella tertiolecta, Emiliania huxleyi, Emericella nidulans, Fusarium oxysporum, Fusarium oxysporum* JCM 11502, *Glyceria maxima, Glycine max, Gossypium hirsutum, Gracilaria chilensis, Gracilaria tenuistipitata, Helianthus annuus, Hordeum vulgare, Lactuca sativa, Lemna minor, Lupinus albus, Mycobactyerium tuberculosis, Nicotiana plumbaginifolia, Nicotiana tabacum, Ogataea* angusta, *Ogataea polymorpha, Oryza sativa, Phaeocystis Antarctica, Phragmites australis, Physcomitrella patens, Pisum arvense, Polytrichum commune, Pyropia yezoensis, Raphanus sativus, Rhodobacter capsulatus, Rhodobacter capsulatus* E1F1, *Ricinus communis, Selaginella kraussiana, Sinapis alba, Skeletonema costatum, Skeletonema tropicum, Solanum lycopersicum, Spinacia oleracea, Suaeda maritima, Tetraselmis gracilis, Thalassia Testudinum, Thalassiosira Antarctica, Thalassiosira pseudonana, Triticum aestivum, Triticum turgidum* subsp *durum, Ulva* sp. And/or *Zea mays*; and/or functional homologues of such NADH-dependent nitrate reductases comprising an amino acid sequence with at least 50, 60, 65, 70, 75, 80, 85, 90, 95, 98 or at least 99% amino acid sequence identity with one or more of such aforementioned NADH-dependent nitrate reductases; and/or functional homologues of such NADH-dependent nitrate reductases comprising an amino acid sequence having one or several substitutions, insertions and/or deletions as compared to the amino acid sequence of one or more of such aforementioned NADH-dependent nitrate reductases, wherein preferably the amino acid sequence of any of the above functional homologues has no more than 300, 250, 200, 150, 100, 75, 50, 40, 30, 20, 10 or 5 amino acid substitutions, insertions and/or deletions as compared to such aforementioned NADH-dependent nitrate reductases.

Preferred NADH-dependent nitrate reductases include the NADH-dependent nitrate reductases as obtained or derived from *Candida boidinii* (a nitrate reductase capable of utilizing both NADH and NADPH as electron donors), *Candida utilis* (a nitrate reductase capable of utilizing both NADH and NADPH as electron donors), *Fusarium oxyspo-*

*rum* (as described by Fujii et al, in their article titled "Denitrification by the Fungus *Fusarium oxysporum* Involves NADH-Nitrate Reductase" published in Biosci. Biotechnol. Biochem., 72 (2), pages 412-420, 2008, incorporated herein by reference), *Spinacia oleracea* and *Zea Mays*.

Preferred NADH-dependent nitrate reductases hence include: NADH-dependent nitrate reductases comprising a polypeptide having an amino acid sequence of SEQ ID NO:1 and/or SEQ ID NO:2, as described herein; and/or functional homologues of SEQ ID NO:1 and/or SEQ ID NO:2 comprising an amino acid sequence with at least 40, 50, 60, 65, 70, 75, 80, 85, 90, 95, 98 or at least 99% amino acid sequence identity with one or more of SEQ ID NO:1 and/or SEQ ID NO:2 respectively; and/or functional homologues of SEQ ID NO:1 and/or SEQ ID NO:2 comprising an amino acid sequence having one or several substitutions, insertions and/or deletions as compared to the amino acid sequence of one or more of SEQ ID NO:1 and/or SEQ ID NO:2 respectively. Preferably the amino acid sequence of any of the above functional homologues has no more than 300, 250, 200, 150, 100, 75, 50, 40, 30, 20, 10 or 5 amino acid substitutions, insertions and/or deletions as compared to SEQ ID NO:1 and/or SEQ ID NO:2 respectively.

Preferably the *Saccharomyces* yeast cell comprises an exogenous gene coding for an enzyme with NADH-dependent nitrate reductase activity. More preferably the *Saccharomyces* yeast cell comprises an exogenous gene coding for an enzyme with NADH-dependent nitrate reductase activity selected from the group consisting of NADH-dependent nitrate reductases as obtained or derived from *Agrostemma githago, Amaranthus hybridus, Amaranthus tricolor, Ankistrodesmus braunii, Arabidopsis thaliana, Aspergillus niger, Aspergillus nidulans, Auxenochlorella pyrenoidosa, Bradyrhizobium* sp., *Bradyrhizobium* sp. 750, *Brassica juncea, Brassica, oleracea, Camellia sinensis, Candida boidinii, Candida utilis, Capsicum frutescens, Chenopodium album, Cyberlindnera jadinii, Brassica juncea, Brassica oleracea, Camellia sinensis, Capsicum frutescens, Chenopodium album, Chlamydomonas reinhardtii, Chlorella fusca, Chlorella* sp. *Chlorella* sp. *Berlin, Chlorella vulgaris, Conticribra weissflogii, Cucumis sativus, Cucurbita maxima, Cucurbita pepo, Cucurbita* sp., *Dunaliella tertiolecta, Emiliania huxleyi, Emericella nidulans, Fusarium oxysporum, Fusarium oxysporum* JCM 11502, *Glyceria maxima, Glycine max, Gossypium hirsutum, Gracilaria chilensis, Gracilaria tenuistipitata, Helianthus annuus, Hordeum vulgare, Lactuca sativa, Lemna minor, Lupinus albus, Mycobactyerium tuberculosis, Nicotiana plumbaginifolia, Nicotiana tabacum, Ogataea angusta, Ogataea polymorpha, Oryza sativa, Phaeocystis Antarctica, Phragmites australis, Physcomitrella patens, Pisum arvense, Polytrichum commune, Pyropia yezoensis, Raphanus sativus, Rhodobacter capsulatus, Rhodobacter capsulatus* E1F1, *Ricinus communis, Selaginella kraussiana, Sinapis alba, Skeletonema costatum, Skeletonema tropicum, Solanum lycopersicum, Spinacia oleracea, Suaeda maritima, Tetraselmis gracilis, Thalassia Testudinum, Thalassiosira Antarctica, Thalassiosira pseudonana, Triticum aestivum, Triticum turgidum* subsp *durum, Ulva* sp. and *Zea mays*, and functional homologues of such NADH-dependent nitrate reductases comprising an amino acid sequence with at least 50, 60, 65, 70, 75, 80, 85, 90, 95, 98 or at least 99% amino acid sequence identity with one or more of such aforementioned NADH-dependent nitrate reductases; and functional homologues of such NADH-dependent nitrate reductases comprising an amino acid sequence having one or several substitutions, insertions and/or deletions as compared to the amino acid sequence of one or more of such aforementioned NADH-dependent nitrate reductases, wherein preferably the amino acid sequence of any of the above functional homologues has no more than 300, 250, 200, 150, 100, 75, 50, 40, 30, 20, 10 or 5 amino acid substitutions, insertions and/or deletions as compared to such aforementioned NADH-dependent nitrate reductases.

Suitably the *Saccharomyces* yeast cell may comprise a nucleotide sequence coding for an amino acid sequence of any of SEQ ID NO:1 and/or SEQ ID NO:2 or an amino acid sequence having one or several substitutions, insertions and/or deletions as compared to the amino acid sequence of any of SEQ ID NO:1 and/or SEQ ID NO:2. Preferably the amino acid sequence has no more than 300, 250, 200, 150, 100, 75, 50, 40, 30, 20, 10 or 5 amino acid substitutions, insertions and/or deletions as compared to SEQ ID NO:1 and/or SEQ ID NO:2 respectively.

The *Saccharomyces* yeast cell may combine one or more genes encoding the above NADH-dependent nitrate reductase with one or more genes encoding an NADPH-dependent nitrite reductase. Preferably, however, the *Saccharomyces* yeast cell combines one or more genes encoding the above NADH-dependent nitrate reductase with one or more genes encoding a NADH-dependent nitrite reductase.

Examples of suitable NADH-dependent nitrate reductases, their UniProt Database Accession number (as can be found on the Uniprot website (uniprot.org/as per 4 Oct. 2020), their description, the organism from which they may be derived, and their amino acid sequence identity with SEQ ID NO:1, are listed in Table 2 below.

TABLE 2

Examples of suitable NADH-dependent nitrate reductases, their UniProt Database Accession number (as can be found on the Uniprot website (uniprot.org/ as per 4 Oct. 2020), their description, the organism from which they may be derived, and their amino acid sequence identity with SEQ ID NO: 1, are listed in Table 2 below.

| UNIPROT DATABASE ACCESSION NUMBER | DESCRIPTION | ORGANISM | IDENTITY TO SEQ ID 1 [%] |
|---|---|---|---|
| K3YG56 | Cluster: Nitrate reductase | PACMAD clade | 94.06 |
| P16081 | Cluster: Nitrate reductase [NADH] 1 | cellular organisms | 90.54 |
| UPI0004DEBCF9 | Cluster: nitrate reductase [NADH]-like | *Zea mays* | 88.57 |

TABLE 2-continued

Examples of suitable NADH-dependent nitrate reductases, their UniProt Database Accession number (as can be found on the Uniprot website (uniprot.org/ as per 4 Oct. 2020), their description, the organism from which they may be derived, and their amino acid sequence identity with SEQ ID NO: 1, are listed in Table 2 below.

| UNIPROT DATABASE ACCESSION NUMBER | DESCRIPTION | ORGANISM | IDENTITY TO SEQ ID 1 [%] |
|---|---|---|---|
| A0A6G1CIJ1 | Cluster: Uncharacterized protein | *Oryza meyeriana* var. *granulata* | 85.7 |
| P27967 | Cluster: Nitrate reductase [NADH] | *Pooideae* | 85.37 |
| A0A3B6T8X1 | Cluster: Nitrate reductase | *Triticinae* | 86.11 |
| A0A4S8IHP6 | Cluster: Nitrate reductase | *Musaceae* | 78.55 |
| A0A2T7D896 | Cluster: Nitrate reductase | *Panicum* | 78.22 |
| A0A199UYK8 | Cluster: Nitrate reductase | *Ananas comosus* | 77.45 |
| A0A4S8J849 | Cluster: Nitrate reductase | *Mesangiospermae* | 77.67 |
| A0A2H3Y7X8 | Cluster: Nitrate reductase | *Arecaceae* | 76.68 |
| A0A4S8JVI1 | Cluster: Nitrate reductase | *Musa balbisiana* | 75.58 |
| A0A200QET5 | Cluster: Nitrate reductase | *Macleaya cordata* | 72.39 |
| F6H0M5 | Cluster: Nitrate reductase | *Vitis* | 72.61 |
| A0A4Y7J3A8 | Cluster: Nitrate reductase | *Papaver somniferum* | 71.95 |
| A0A218XU44 | Cluster: Nitrate reductase | *Punica granatum* | 71.73 |
| A0A2C9PIN3 | Cluster: Nitrate reductase | *Phellodendron amurense* | 72.06 |
| UPI000B8CEBA2 | Cluster: nitrate reductase [NADH]-like | *Carica papaya* | 71.51 |
| A0A2R6RP67 | Cluster: Nitrate reductase | *Actinidia chinensis* var. *chinensis* | 70.63 |
| A0A5J5BUB1 | Cluster: Nitrate reductase | *Nyssa sinensis* | 71.29 |
| V4TCH9 | Cluster: Nitrate reductase | Citrus | 71.51 |
| P36859 | Cluster: Nitrate reductase [NADH] | *Petunia hybrida* | 71.62 |
| A0A0E0GDD5 | Cluster: Nitrate reductase | *Oryzinae* | 74.76 |
| UPI001263D0A7 | Cluster: nitrate reductase [NAD(P)H]-like | *Pistacia vera* | 71.4 |
| A0A061FFV7 | Cluster: Nitrate reductase | *Byttnerioideae* | 70.85 |
| K3YPT2 | Cluster: Nitrate reductase | *Panicoideae* | 75.21 |
| A0A1U7ZDA9 | Cluster: Nitrate reductase | *Nelumbo nucifera* | 72.17 |
| A0A0P0VPX4 | Cluster: Nitrate reductase | *Oryza* | 74.17 |
| A0A6A3CP56 | Cluster: Nitrate reductase | *Hibiscus syriacus* | 69.97 |
| A0A067KLT8 | Cluster: Nitrate reductase | *Jatropha curcas* | 70.08 |
| A0A214H0D3 | Cluster: Nitrate reductase | *Juglans regia* | 69.86 |
| A0A5J9UYH6 | Cluster: Uncharacterized protein (Fragment) | PACMAD clade | 74.26 |
| A0A5N6RHU6 | Cluster: Nitrate reductase | fabids | 70.63 |
| A0A1U8KZC0 | Cluster: Nitrate reductase | *Malvaceae* | 70.74 |
| UPI000C0393D8 | Cluster: nitrate reductase [NADH]-like | *Durio zibethinus* | 73.33 |
| B9H7A1 | Cluster: Nitrate reductase | *Saliceae* | 70.41 |

TABLE 2-continued

Examples of suitable NADH-dependent nitrate reductases, their UniProt Database Accession number (as can be found on the Uniprot website (uniprot.org/ as per 4 Oct. 2020), their description, the organism from which they may be derived, and their amino acid sequence identity with SEQ ID NO: 1, are listed in Table 2 below.

| UNIPROT DATABASE ACCESSION NUMBER | DESCRIPTION | ORGANISM | IDENTITY TO SEQ ID 1 [%] |
|---|---|---|---|
| P17569 | Cluster: Nitrate reductase [NADH] | *Cucurbitaceae* | 70.74 |
| UPI000581598E | Cluster: nitrate reductase [NADH] 2-like | *Sesamum indicum* | 70.41 |
| UPI000F7C3BDF | Cluster: nitrate reductase [NADH] 2 isoform X1 | *Abrus precatorius* | 74.12 |
| P08509 | Cluster: Nitrate reductase [NADH] 2 | *Solanaceae* | 70.08 |
| P39867 | Cluster: Nitrate reductase [NADH], clone PBNBR1405 | *Brassiceae* | 71.65 |
| UPI000C1D548F | Cluster: nitrate reductase [NADH] 2-like | *Olea europaea* var. *sylvestris* | 71.22 |
| P39866 | Cluster: Nitrate reductase [NADH] 2 | *Phaseoleae* | 73.88 |
| P27968 | Cluster: Nitrate reductase [NAD(P)H] | *Triticeae* | 72.82 |
| A8IJ84 | Cluster: Nitrate reductase | *Beta vulgaris* | 71.14 |
| A0A2U1KIT7 | Cluster: Nitrate reductase | *Artemisia annua* | 69.64 |
| A0A165XNP4 | Cluster: Nitrate reductase | *Daucus carota* subsp. *sativus* | 69.31 |
| B9RJB1 | Cluster: Nitrate reductase | *Mesangiospermae* | 74 |
| P43101 | Cluster: Nitrate reductase [NADH] | *Asteraceae* | 69.86 |
| I1LW34 | Cluster: Nitrate reductase | *Glycine* subgen. *Soja* | 74.49 |
| UPI000980E182 | Cluster: nitrate reductase [NADH]-like | *Ananas comosus* | 75.54 |
| A0A4P1R4X1 | Cluster: Nitrate reductase | *Lupinus angustifolius* | 71.22 |
| Q8H1T7 | Cluster: Nitrate reductase | *Tilia platyphyllos* | 69.42 |
| I1IER4 | Cluster: Nitrate reductase | *Brachypodium distachyon* | 73.47 |
| A0A1U7Z2Y3 | Cluster: Nitrate reductase | *Nelumbo nucifera* | 72.45 |
| A0A068VGB5 | Cluster: Nitrate reductase | *Coffea* | 68.87 |
| A0A2T7F896 | Cluster: Nitrate reductase | *Panicum* | 73.27 |
| A0A2Z7C1Z2 | Cluster: Nitrate reductase | *Dorcoceras hygrometricum* | 69.31 |
| UPI00053C7726 | Cluster: nitrate reductase [NADH] 2 | *Tarenaya hassleriana* | 69.64 |
| A0A445BT68 | Cluster: Nitrate reductase (NADH) | *Arachis* | 72.55 |
| P39869 | Cluster: Nitrate reductase [NADH] | *Lotus japonicus* | 73.76 |
| UPI0010FB6302 | Cluster: nitrate reductase [NADH] 2 | *Cajanus cajan* | 73.64 |
| Q93XS1 | Cluster: Nitrate reductase | *Prunus* | 73.76 |
| A0A022Q6Q6 | Cluster: Nitrate reductase | *Erythranthe guttata* | 69.2 |
| A0A1U8NV83 | Cluster: Nitrate reductase | *Gossypium* | 73.04 |
| P27783 | Cluster: Nitrate reductase [NAD(P)H] | fabids | 69.53 |
| A0A2T8KWM5 | Cluster: Nitrate reductase | *Panicum hallii* | 72.93 |
| A0A214GBD5 | Cluster: Nitrate reductase | *Juglans regia* | 69.42 |

TABLE 2-continued

Examples of suitable NADH-dependent nitrate reductases, their UniProt Database Accession number (as can be found on the Uniprot website (uniprot.org/ as per 4 Oct. 2020), their description, the organism from which they may be derived, and their amino acid sequence identity with SEQ ID NO: 1, are listed in Table 2 below.

| UNIPROT DATABASE ACCESSION NUMBER | DESCRIPTION | ORGANISM | IDENTITY TO SEQ ID 1 [%] |
|---|---|---|---|
| A0A5N6PSR2 | Cluster: Nitrate reductase | *Mikania micrantha* | 69.2 |
| A0A2P6PI42 | Cluster: Nitrate reductase | *Mesangiospermae* | 73.88 |
| E7ELN7 | Cluster: Nitrate reductase | IRL clade | 70.41 |
| A0A4U5QSR8 | Cluster: Nitrate reductase | *Populus* | 73.64 |
| A0A2K2BFU1 | Cluster: Nitrate reductase | *Saliceae* | 74.12 |
| A0A1Z5RNB1 | Cluster: Nitrate reductase | *Sorghum bicolor* | 76.67 |
| A0A0M4P4G3 | Cluster: Nitrate reductase | rosids | 73.28 |
| M4CVT6 | Cluster: Nitrate reductase | *Brassica campestris* | 70.47 |
| A0A251SAE9 | Cluster: Nitrate reductase | *Helianthus annuus* | 72.55 |
| A0A2G5DUU4 | Cluster: Nitrate reductase | *Aquilegia coerulea* | 71.24 |
| P23312 | Cluster: Nitrate reductase [NADH] | *Chenopodioideae* | 72.79 |
| P11832 | Cluster: Nitrate reductase [NADH] 1 | *Brassicaceae* | 71.22 |
| P11035 | Cluster: Nitrate reductase [NADH] 2 | rosids | 68.76 |
| W1NJD0 | Cluster: Nitrate reductase | *Magnoliopsida* | 69.31 |
| UPI000C048389 | Cluster: nitrate reductase [NADH]-like | *Durio zibethinus* | 71.36 |
| A0A6A3C902 | Cluster: Nitrate reductase | *Hibiscus syriacus* | 73.16 |
| P39870 | Cluster: Inducible nitrate reductase [NADH] 2 | *Glycine* subgen. *Soja* | 73.52 |
| UPI000F7C9CC8 | Cluster: inducible nitrate reductase [NADH] 2 | *Abrus precatorius* | 72.79 |
| A0A6A5MI86 | Cluster: Nitrate reductase | *Lupinus* | 70.31 |

Nitrite Reductase

As indicated above, nitrite reductase catalyzes the reduction of nitrite to ammonia ($NH_3$).

Preferably the *Saccharomyces* yeast cell as described herein comprises at least one or more genes encoding a NADH-dependent nitrite reductase.

By a NADH-dependent nitrite reductase is herein understood a nitrite reductase that is exclusively depended on NADH as a co-factor or that is predominantly dependent on NADH as a cofactor. Preferably the NADH-dependent nitrite reductase has a ratio of catalytic efficiency for NADPH/NADP+ as a cofactor $(k_{cat}/K_m)^{NAD+}$ to NADH/NAD+ as cofactor $(k_{cat}/K_m)^{NAD+}$, i.e. a catalytic efficiency ratio $(k_{cat}/K_m)^{NADP+}:(k_{cat}/K_m)^{NAD+}$, of more than 1:1, more preferably of equal to or more than 2:1, still more preferably of equal to or more than 5:1, even more preferably of equal to or more than 10:1, yet even more preferably of equal to or more than 20:1, even still more preferably of equal to or more than 100:1, and most preferably equal to or more than 1000:1. There is no upper limit, but for practical reasons the NADH-dependent nitrite reductase may have a catalytic efficiency ratio $(k_{cat}/K_m)^{NADP+}:(k_{cat}/K_m)^{NAD+}$ of equal to or less than 1.000.000.000:1 (i.e. $1.10^9$). Most preferably the NADH-dependent nitrite reductase is exclusively depended on NADH/NAD+ as a co-factor. That is, most preferably the NADH-dependent nitrite reductase has an absolute requirement for NADH/NAD+ as a cofactor instead of NADPH/NADP+ as a cofactor.

Preferably the NADH-dependent nitrite reductase is a NADH-dependent nitrite reductase with enzyme classification EC 1.7.1.15 (i.e. with EC number EC 1.7.1.15). Suitably the NADH-dependent nitrite reductase, also referred to as NADH-dependent nitrite oxidoreductase, is an enzyme that catalyzes at least the following chemical reaction:

$$\text{nitrite}+3\text{NADH}+5\text{H}^+\rightarrow\text{ammonia}+3\text{NAD}^++2\text{H}_2\text{O}$$

The person skilled in the art will understand that the ammonia may also be present and/or referred to as so-called ammonium hydroxide $NH_4OH$ Suitable NADH-dependent nitrite reductases may include one or more NADH-dependent nitrite reductases as derived from *Aspergillus nidulans* (also called *Emericella nidulans*), *Arcobacter ellisii, Arcobacter pacificus Bacillus subtilis, Bacillus subtilis* JH642, *Cupriavidus taiwanensis Escheri-*

*chia coli, Ralstonia taiwanensis, Ralstonia syzygii, Ralstonia solanacearum, Rhodobacter capsulatus, Rhodobacter capsulatus, Paraburkholderia ribeironis*; and/or functional homologues of such NADH-dependent nitrite reductases comprising an amino acid sequence with at least 40, 50, 60, 65, 70, 75, 80, 85, 90, 95, 98 or at least 99% amino acid sequence identity with one or more of such aforementioned NADH-dependent nitrite reductases; and/or functional homologues of such NADH-dependent nitrite reductases comprising an amino acid sequence having one or several substitutions, insertions and/or deletions as compared to the amino acid sequence of one or more of such aforementioned NADH-dependent nitrite reductases, wherein preferably the amino acid sequence of any of the above functional homologues has no more than 300, 250, 200, 150, 100, 75, 50, 40, 30, 20, 10 or 5 amino acid substitutions, insertions and/or deletions as compared to such aforementioned NADH-dependent nitrite reductases.

*Escherichia coli* utilizes several distinct enzymes in its nitrite assimilation pathway. The nirD gene encodes a NADH-dependent nitrite reductase (NADH) small subunit, whilst the nirB gene encodes a NADH-dependent nitrite reductase (NADH) large subunit.

Preferred NADH-dependent nitrite reductases include the NADH-dependent nitrite reductases as derived from *Aspergillus nidulans* (also called *Emericella nidulans*), a nitrite reductase capable of utilizing both NADH and NADPH as electron donors, and/or *Escherichia coli*. At high nitrate and/or nitrite concentrations, the nitrite reductase encoded by the nirB gene of *Escherichia coli* is especially preferred.

Preferred NADH-dependent nitrite reductases hence include: NADH-dependent nitrite reductases comprising a polypeptide having an amino acid sequence of SEQ ID NO:3 (*E. coli* nitrate reductase small subunit encoded by nirD) and/or SEQ ID NO:4 (*E. coli* nitrate reductase large subunit encoded by nirB) and/or SEQ ID NO:5 (*Emericella nidulans* nitrate reductase encoded by niiA), as described herein; and/or functional homologues of SEQ ID NO:3 and/or SEQ ID NO:4 and/or SEQ ID NO:5 comprising an amino acid sequence with at least 40, 50, 60, 65, 70, 75, 80, 85, 90, 95, 98 or at least 99% amino acid sequence identity with one or more of SEQ ID NO:3 and/or SEQ ID NO:4 and/or SEQ ID NO:5 respectively; and/or functional homologues of SEQ ID NO:3 and/or SEQ ID NO:4 and/or SEQ ID NO:5 comprising an amino acid sequence having one or several substitutions, insertions and/or deletions as compared to the amino acid sequence of one or more of SEQ ID NO:3 and/or SEQ ID NO:4 and/or SEQ ID NO:5 respectively. Preferably the amino acid sequence of any of the above functional homologues has no more than 300, 250, 200, 150, 100, 75, 50, 40, 30, 20, 10 or 5 amino acid substitutions, insertions and/or deletions as compared to SEQ ID NO:3 and/or SEQ ID NO:4 and/or SEQ ID NO:5 respectively.

Preferably the *Saccharomyces* yeast cell comprises an exogenous gene coding for an enzyme with NADH-dependent nitrite reductase activity. More preferably the *Saccharomyces* yeast cell comprises an exogenous gene coding for an enzyme with NADH-dependent nitrite reductase activity selected from the group consisting of NADH-dependent nitrite reductases as derived from *Aspergillus nidulans* (also called *Emericella nidulans*), *Arcobacter ellisii, Arcobacter pacificus Bacillus subtilis, Bacillus subtilis* JH642, *Cupriavidus taiwanensis Escherichia coli, Ralstonia taiwanensis, Ralstonia syzygii, Ralstonia solanacearum, Rhodobacter capsulatus, Rhodobacter capsulatus, Paraburkholderia ribeironis*; and/or functional homologues of such NADH-dependent nitrite reductases comprising an amino acid sequence with at least 40, 50, 60, 65, 70, 75, 80, 85, 90, 95, 98 or at least 99% amino acid sequence identity with one or more of such aforementioned NADH-dependent nitrite reductases; and/or functional homologues of such NADH-dependent nitrite reductases comprising an amino acid sequence having one or several substitutions, insertions and/or deletions as compared to the amino acid sequence of one or more of such aforementioned NADH-dependent nitrite reductases, wherein preferably the amino acid sequence of any of the above functional homologues has no more than 300, 250, 200, 150, 100, 75, 50, 40, 30, 20, 10 or 5 amino acid substitutions, insertions and/or deletions as compared to such aforementioned NADH-dependent nitrite reductases.

Suitably the *Saccharomyces* yeast cell may comprise a nucleotide sequence coding for an amino acid sequence of any of SEQ ID NO:3 (*E. coli* nitrate reductase small subunit encoded by nirD) and/or SEQ ID NO:4 (*E. coli* nitrate reductase large subunit encoded by nirB) and/or SEQ ID NO:5 (*Emericella nidulans* nitrate reductase encoded by niiA), or an amino acid sequence having one or several substitutions, insertions and/or deletions as compared to the amino acid sequence of any of SEQ ID NO:3 and/or SEQ ID NO:4 and/or SEQ ID NO:5. Preferably the amino acid sequence has no more than 300, 250, 200, 150, 100, 75, 50, 40, 30, 20, 10 or 5 amino acid substitutions, insertions and/or deletions as compared to SEQ ID NO:3 and/or SEQ ID NO:4 and/or SEQ ID NO:5 respectively.

The *Saccharomyces* yeast cell may combine one or more genes encoding one or more of the above NADH-dependent nitrite reductases with one or more genes encoding an NADPH-dependent nitrate reductase. Preferably, however, the *Saccharomyces* yeast cell combines one or more genes encoding one or more of the above NADH-dependent nitrite reductases with one or more genes encoding a NADH-dependent nitrate reductase.

Examples of suitable NADH-dependent nitrite reductases, their UniProt Database Accession number (as can be found on the Uniprot website (uniprot.org/as per 4 Oct. 2020), their description, the organism from which they may be derived, and their amino acid sequence identity with SEQ ID NO:3 (small subunit encoded by nirD), are listed in Table 3 below.

Examples of suitable NADH-dependent nitrite reductases, their UniProt Database Accession number (as can be found on the Uniprot website (uniprot.org/as per 4 Oct. 2020), their description, the organism from which they may be derived, and their amino acid sequence identity with SEQ ID NO:4 (large subunit encoded by nirB), are listed in Table 4 below.

TABLE 3

Examples of suitable NADH-dependent nitrite reductases, their UniProt Database Accession number (as can be found on the Uniprot website (uniprot.org/ as per 4 Oct. 2020), their description, the organism from which they may be derived, and their amino acid sequence identity with SEQ ID NO: 3 (small subunit encoded by nirD).

| UNIPROT DATABASE ACCESSION NUMBER | DESCRIPTION | ORGANISM | IDENTITY TO SEQ ID 3 [%] |
|---|---|---|---|
| E2QFM2 | Cluster: Nitrite reductase | Gammaproteobacteria | 99.07 |
| A0A078LHD3 | Cluster: Nitrite reductase small subunit | *Enterobacteriaceae* | 94.44 |
| P0A230 | Cluster: Nitrite reductase (NADH) small subunit | Bacteria | 93.52 |
| A0A170JME2 | Cluster: Nitrite reductase [NAD(P)H] small subunit | *Enterobacteriaceae* | 91.67 |
| A0A0F6TX22 | Cluster: Nitrite reductase | Gammaproteobacteria | 91.67 |
| A0A6D0EPI7 | Cluster: Nitrite reductase small subunit NirD | *Enterobacteriaceae* | 87.04 |
| A0A198H1N5 | Cluster: Nitrite reductase [NAD(P)H] small subunit | Bacteria | 86.11 |
| A0A447MQ21 | Cluster: Nitrite reductase [NAD(P)H] small subunit | *Enterobacteriaceae* | 84.26 |
| UPI00077B73C7 | Cluster: nitrite reductase small subunit NirD | *Enterobacter timonensis* | 83.33 |
| A0A094XNF5 | Cluster: Nitrite reductase (NADH) small subunit | *Enterobacterales* | 82.41 |
| UPI00105F841D | Cluster: nitrite reductase small subunit NirD | *Enterobacter* sp. OV724 | 81.48 |
| A0A1X0XB32 | Cluster: Nitrite reductase small subunit | *Enterobacterales* | 81.48 |
| A0A1A9FFN3 | Cluster: Nitrite reductase small subunit | *Lelliottia amnigena* | 81.48 |
| UPI0002D5E0A7 | Cluster: nitrite reductase small subunit NirD | *Metakosakonia massiliensis* | 80.56 |
| UPI0004E24438 | Cluster: nitrite reductase small subunit NirD | *Siccibacter colletis* | 79.63 |
| A0A514EKN7 | Cluster: Nitrite reductase [NAD(P)H] small subunit | *Enterobacteriaceae* | 77.78 |
| A0A2P8VHS5 | Cluster: Nitrite reductase small subunit NirD | *Enterobacteriaceae* | 80.56 |
| A0A4V3BP91 | Cluster: Nitrite reductase (NADH) small subunit | cellular organisms | 80.56 |
| A0A3R9F800 | Cluster: Nitrite reductase small subunit NirD | *Enterobacteriaceae* | 79.63 |
| R9VMQ4 | Cluster: Nitrite reductase small subunit | *Enterobacteriaceae* | 78.7 |
| A0A285KH74 | Cluster: Nitrite reductase (NADH) small subunit | *Enterobacter* sp. CC120223-11 | 80.37 |
| A0A658U6S1 | Cluster: Assimilatory nitrite reductase (NAD(P)H) small subunit | *Enterobacter* | 77.78 |
| A0A085A429 | Cluster: Nitrite reductase [NAD(P)H] small subunit | *Enterobacteriaceae* | 78.7 |
| A0A1V0L823 | Cluster: Nitrite reductase small subunit | *Kosakonia* | 76.85 |
| UPI001431C56A | Cluster: nitrite reductase small subunit NirD | *Cedecea colo* | 75 |

TABLE 3-continued

Examples of suitable NADH-dependent nitrite reductases, their UniProt Database Accession number (as can be found on the Uniprot website (uniprot.org/ as per 4 Oct. 2020), their description, the organism from which they may be derived, and their amino acid sequence identity with SEQ ID NO: 3 (small subunit encoded by nirD).

| UNIPROT DATABASE ACCESSION NUMBER | DESCRIPTION | ORGANISM | IDENTITY TO SEQ ID 3 [%] |
|---|---|---|---|
| A0A085G1A1 | Cluster: Nitrite reductase [NAD(P)H] small subunit | *Enterobacteriaceae* | 75 |
| A0A089PL75 | Cluster: Nitrite reductase | *Pluralibacter gergoviae* | 76.85 |
| A0A3C0H311 | Cluster: Nitrite reductase small subunit | *Enterobacteriaceae* | 77.78 |
| A0A3N2DXC8 | Cluster: Assimilatory nitrite reductase (NAD(P)H) small subunit | unclassified *Enterobacter* | 75.93 |
| A0A0L0ATR1 | Cluster: Nitrite reductase | *Enterobacteriaceae* | 78.5 |
| K8AGI3 | Cluster: Nitrite reductase [NAD(P)H] small subunit | *Cronobacter condimenti* 1330 | 75 |
| A0A1I6EAU0 | Cluster: Nitrite reductase (NADH) small subunit | *Enterobacter* sp. kpr-6 | 75 |
| A0A0D5X0Q1 | Cluster: Nitrite reductase | *Enterobacteriaceae* | 75 |
| C9Y259 | Cluster: Nitrite reductase [NAD(P)H] small subunit | *Enterobacteriaceae* | 74.07 |
| A0A4R0GWC0 | Cluster: Nitrite reductase small subunit NirD | *Kosakonia quasisacchari* | 75 |
| UPI00057BF926 | Cluster: nitrite reductase small subunit NirD | *Enterobacter* sp. Bisph1 | 73.15 |
| A0A495AHM0 | Cluster: Nitrite reductase small subunit NirD | *Enterobacter* sp. R1(2018) | 72.22 |
| A0A447QKU3 | Cluster: Nitrite reductase [NAD(P)H] small subunit | *Yersiniaceae* | 75.47 |
| I2B4C9 | Cluster: Nitrite reductase (NAD(P)H) | *Shimwellia blattae* (strain ATCC 29907/DSM 4481/JCM 1650/NBRC 105725/CDC 9005-74) | 73.83 |
| UPI0012B7CAE2 | Cluster: nitrite reductase small subunit NirD | *Erwinia* sp. CPCC 100877 | 72.22 |
| UPI00073DB139 | Cluster: nitrite reductase small subunit NirD | [*Erwinia*] *teleogrylli* | 73.83 |
| UPI000237D150 | Cluster: nitrite reductase small subunit NirD | *Enterobacter mori* | 80.56 |
| A0A4P8YE33 | Cluster: Nitrite reductase small subunit NirD | *Enterobacteriaceae* | 72.22 |
| UPI0005DC1E97 | Cluster: nitrite reductase small subunit NirD | *Yersinia rohdei* | 71.03 |
| A0A0U1HQI4 | Cluster: Nitrite reductase small subunit | *Yersinia* | 71.03 |
| A0A0K0HM15 | Cluster: Nitrite reductase [NAD(P)H] small subunit | *Enterobacterales* | 72.9 |
| H8NP95 | Cluster: Nitrite reductase small subunit | *Yersiniaceae* | 69.16 |
| A0A2S4QQ85 | Cluster: Nitrite reductase small subunit | *Enterobacteriaceae* | 69.44 |
| A0A0A7RXK3 | Cluster: Assimilatory nitrite reductase (NAD(P)H) small subunit | *Frischella perrara* | 71.3 |

TABLE 3-continued

Examples of suitable NADH-dependent nitrite reductases, their UniProt Database Accession number (as can be found on the Uniprot website (uniprot.org/ as per 4 Oct. 2020), their description, the organism from which they may be derived, and their amino acid sequence identity with SEQ ID NO: 3 (small subunit encoded by nirD).

| UNIPROT DATABASE ACCESSION NUMBER | DESCRIPTION | ORGANISM | IDENTITY TO SEQ ID 3 [%] |
|---|---|---|---|
| D4DYL5 | Cluster: Nitrite reductase [NAD(P)H], small subunit | *Serratia odorifera* DSM 4582 | 73.58 |
| A0A370QTS9 | Cluster: Assimilatory nitrite reductase (NAD(P)H) small subunit | *Enterobacillus tribolii* | 71.7 |
| A0A1B9JUB0 | Cluster: Nitrite reductase small subunit | *Gilliamella apicola* | 69.16 |
| A0A085U6Z8 | Cluster: Nitrite reductase [NAD(P)H] small subunit | *Yersinia ruckeri* | 72.22 |
| UPI00156B8D43 | Cluster: UPI00156B8D43 related cluster | unknown | 70.75 |
| A0A0T9KRE5 | Cluster: Nitrite reductase small subunit | *Yersinia* | 70.37 |
| A0A066TFS8 | Cluster: Nitrite reductase [NAD(P)H] small subunit | *Gilliamella* | 69.16 |
| A0A1B9M9X4 | Cluster: Nitrite reductase small subunit | *Gilliamella* | 68.22 |
| A0A0E1NM95 | Cluster: Nitrite reductase (NAD(P)H) | *Yersiniaceae* | 68.52 |
| A0A080K0G0 | Cluster: Ferredoxin subunits of nitrite reductase and ring-hydroxylating dioxygenase | *Snodgrassella alvi* SCGC AB-598-O02 | 69.16 |
| A0A0Q4N870 | Cluster: Nitrite reductase small subunit | *Enterobacterales* | 67.29 |
| UPI0004A391D4 | Cluster: nitrite reductase small subunit NirD | *Tatumella saanichensis* | 69.81 |
| A0A1B9ZVE6 | Cluster: Nitrite reductase small subunit | *Gilliamella apicola* | 67.29 |
| A0A0T9JI92 | Cluster: Nitrite reductase small subunit | *Yersinia* | 68.52 |
| A0A2N5EJM2 | Cluster: Nitrite reductase small subunit NirD | *Chimaeribacter* | 67.59 |
| A0A2V4E983 | Cluster: Nitrite reductase small subunit | *Gilliamella* | 65.74 |
| A0A419N5U0 | Cluster: Nitrite reductase small subunit NirD | *Yersiniaceae* | 67.29 |
| A0A0F7H970 | Cluster: Nitrite reductase | *Serratia* | 70.75 |
| A0A318NZT5 | Cluster: Nitrite reductase small subunit NirD | *Yersiniaceae* | 69.81 |
| A0A250B1W9 | Cluster: Nitrite reductase small subunit | *Gibbsiella quercinecans* | 69.81 |
| A0A6G9I849 | Cluster: Nitrite reductase small subunit NirD | *Orbus* sp. IPMB12 | 65.74 |
| A0A419M923 | Cluster: Nitrite reductase small subunit NirD | *Rahnella inusitata* | 67.92 |
| A0A389M9P6 | Cluster: Nitrite reductase (NADH) small subunit | *Enterobacterales* | 67.29 |
| A0A0N8GUB4 | Cluster: Nitrite reductase (NADH) small subunit | *Vibrionales* | 67.96 |
| A0A443IEH9 | Cluster: Nitrite reductase | *Pantoea* sp. LMG 27579 | 68.87 |
| A0A1X1MLP8 | Cluster: Nitrite reductase | *Vibrio* sp. qd031 | 69.9 |

TABLE 3-continued

Examples of suitable NADH-dependent nitrite reductases, their UniProt Database Accession number (as can be found on the Uniprot website (uniprot.org/ as per 4 Oct. 2020), their description, the organism from which they may be derived, and their amino acid sequence identity with SEQ ID NO: 3 (small subunit encoded by nirD).

| UNIPROT DATABASE ACCESSION NUMBER | DESCRIPTION | ORGANISM | IDENTITY TO SEQ ID 3 [%] |
|---|---|---|---|
| A0A542BGK2 | Cluster: Assimilatory nitrite reductase (NAD(P)H) small subunit | *Serratia fonticola* | 68.87 |
| A0A2U3B6U3 | Cluster: Nitrite reductase small subunit | *Vibrio* sp. E4404 | 67.92 |
| A0A240CDV1 | Cluster: Nitrite reductase [NAD(P)H] small subunit | Gammaproteobacteria | 67.92 |
| A0A2S9I8J3 | Cluster: Nitrite reductase small subunit | Bacteria | 67.29 |
| A0A495RE76 | Cluster: Assimilatory nitrite reductase (NAD(P)H) small subunit | *Orbus hercynius* | 67.59 |
| A0A178KL05 | Cluster: Nitrite reductase small subunit | Photobacterium | 66.04 |
| A0A198GJ99 | Cluster: Nitrite reductase [NAD(P)H] small subunit | *Cosenzaea myxofaciens* ATCC 19692 | 63.55 |
| A0A2N0W0U3 | Cluster: Nitrite reductase small subunit | *Enterobacterales* | 66.36 |
| A0A1B9JKC9 | Cluster: Nitrite reductase small subunit | *Gilliamella apicola* | 66.67 |
| UPI0011BEE383 | Cluster: nitrite reductase small subunit NirD | *Pantoea* sp. CCBC3-3-1 | 65.09 |
| A0A085G554 | Cluster: Nitrite reductase [NAD(P)H] small subunit | *Ewingella americana* | 67.29 |
| A0A1B1NU77 | Cluster: Nitrite reductase (NADH) | *Vibrio* | 67.96 |
| A0A2N7G6C9 | Cluster: Nitrite reductase small subunit | *Vibrio* sp. 10N.261.55.A7 | 67.96 |
| A0A349FFE1 | Cluster: Nitrite reductase small subunit | *Vibrio* sp. | 69.52 |
| A0A1B9JS56 | Cluster: Nitrite reductase small subunit | *Gilliamella apicola* | 64.49 |
| A0A366XH21 | Cluster: Nitrite reductase small subunit | *Vibrionales* | 66.67 |
| UPI00062A46AC | Cluster: nitrite reductase small subunit NirD | *Tatumella morbirosei* | 67.59 |
| UPI00046A4834 | Cluster: nitrite reductase small subunit NirD | *Pantoea* sp. IMH | 68.87 |

TABLE 4

Examples of suitable NADH-dependent nitrite reductases, their UniProt Database Accession number (as can be found on the Uniprot website (uniprot.org/ as per 4 Oct. 2020), their description, the organism from which they may be derived, and their amino acid sequence identity with SEQ ID NO: 4 (large subunit encoded by nirB).

| UNIPROT DATABASE ACCESSION NUMBER | DESCRIPTION | ORGANISM | IDENTITY TO SEQ ID 4 [%] |
|---|---|---|---|
| W9B2S1 | Cluster: NirB protein | Bacteria | 93.27 |
| A0A486K457 | Cluster: Nitrite reductase [NAD(P)H] | *Enterobacterales* | 93.15 |
| A0A1B7KIV8 | Cluster: Nitrite reductase [NAD(P)H] large subunit | *Enterobacterales* | 85.41 |

TABLE 4-continued

Examples of suitable NADH-dependent nitrite reductases, their UniProt Database Accession number (as can be found on the Uniprot website (uniprot.org/ as per 4 Oct. 2020), their description, the organism from which they may be derived, and their amino acid sequence identity with SEQ ID NO: 4 (large subunit encoded by nirB).

| UNIPROT DATABASE ACCESSION NUMBER | DESCRIPTION | ORGANISM | IDENTITY TO SEQ ID 4 [%] |
|---|---|---|---|
| A0A087L3N6 | Cluster: Nitrite reductase | *Serratia* | 84.6 |
| A0A654DEI2 | Cluster: Nitrite reductase, large subunit, nucleotide-and Fe/S-cluster binding | *Enterobacterales* | 84.36 |
| UPI00156BAB07 | Cluster: UPI00156BAB07 related cluster | unknown | 81.3 |
| A0A2I0FWV2 | Cluster: Nitrite reductase (NAD(P)H) | *Enterobacterales* bacterium CwR94 | 81.52 |
| I2B4D0 | Cluster: Nitrite reductase (NAD(P)H) | *Shimwellia blattae* (strain ATCC 29907/DSM 4481/JCM 1650/NBRC 105725/CDC 9005-74) | 85.24 |
| A0A370QTZ7 | Cluster: Assimilatory nitrite reductase (NAD(P)H) large subunit | *Enterobacillus tribolii* | 83.39 |
| UPI000DEFBD5D | Cluster: nitrite reductase large subunit | *Edaphovirga cremea* | 83.53 |
| A0A380ASL5 | Cluster: Nitric oxide reductase FIRd-NAD(+) reductase | cellular organisms | 84.36 |
| A0A443IEI0 | Cluster: Nitrite reductase | unclassified *Pantoea* | 81.42 |
| A0A221T4L0 | Cluster: Nitrite reductase [NAD(P)H] large subunit | *Enterobacterales* | 80.45 |
| A0A2N5EJN0 | Cluster: Nitrite reductase (NAD(P)H) | *Enterobacterales* | 82.68 |
| A0A377N6S4 | Cluster: Benzene 1,2-dioxygenase system ferredoxin--NAD(+) reductase subunit | *Enterobacterales* | 82.82 |
| A0A4P8SFP8 | Cluster: Nitrite reductase (NAD(P)H) | *Nissabacter* sp. SGAir0207 | 82.11 |
| A0A0L7TEE8 | Cluster: Nitrite reductase | *Erwinia iniecta* | 79.62 |
| A0A1W6B3D3 | Cluster: Nitrite reductase large subunit | *Erwiniaceae* | 79.88 |
| A0A506V9E3 | Cluster: Nitrite reductase large subunit | *Mixta* | 79.41 |
| UPI000468AD1D | Cluster: nitrite reductase large subunit | *Erwiniaceae* | 81.02 |
| A0A0N0Z921 | Cluster: Nitrite reductase [NAD(P)H] large subunit | *Moellerella wisconsensis* | 79.34 |
| B4EXR2 | Cluster: Nitrite reductase [NAD(P)H] large subunit | *Enterobacterales* | 78.34 |
| A0A198GKA3 | Cluster: Nitrite reductase [NAD(P)H] large subunit | *Cosenzaea myxofaciens* ATCC 19692 | 78.11 |
| A0A0F3LTP0 | Cluster: Nitrite reductase | *Enterobacterales* | 78.46 |
| E1SGS9 | Cluster: Nitrite reductase (NAD(P)H) subunit | *Erwiniaceae* | 77.78 |
| A0A1X1EZA9 | Cluster: Nitrite reductase large subunit | *Pantoea cypripedii* | 78.25 |
| A0A3A9I4K8 | Cluster: Nitrite reductase large subunit | *Erwiniaceae* | 77.9 |
| A0A2S9I8J4 | Cluster: Nitrite reductase (NAD(P)H) | *Erwiniaceae* | 79.48 |

TABLE 4-continued

Examples of suitable NADH-dependent nitrite reductases, their UniProt Database Accession number (as can be found on the Uniprot website (uniprot.org/ as per 4 Oct. 2020), their description, the organism from which they may be derived, and their amino acid sequence identity with SEQ ID NO: 4 (large subunit encoded by nirB).

| UNIPROT DATABASE ACCESSION NUMBER | DESCRIPTION | ORGANISM | IDENTITY TO SEQ ID 4 [%] |
|---|---|---|---|
| A0A0R4FQI6 | Cluster: Nitrite reductase, large subunit, nucleotide-binding | *Xenorhabdus nematophila* | 76.42 |
| UPI001265FD68 | Cluster: nitrite reductase large subunit | *Erwinia endophytica* | 77.49 |
| UPI00146D663B | Cluster: nitrite reductase large subunit | *Rahnella* sp. SAP-1 | 78.32 |
| A0A3S4CWL7 | Cluster: Rubredoxin-NAD(+) reductase | *Enterobacterales* | 78.65 |
| A0A1Y2S8S4 | Cluster: NADH oxidase | *Xenorhabdus vietnamensis* | 76.78 |
| A0A0A3YW59 | Cluster: Nitrite reductase | *Erwinia typographi* | 79.31 |
| A0A506PS78 | Cluster: Nitrite reductase large subunit | *Pantoea* | 76.12 |
| D8MY05 | Cluster: Nitrite reductase [NAD(P)H] large subunit | *Erwinia* | 79.12 |
| E6WGY1 | Cluster: Nitrite reductase (NAD(P)H), large subunit | unclassified *Pantoea* | 75.62 |
| A0A3R8ZPT1 | Cluster: Nitrite reductase large subunit | unclassified *Erwinia* | 75.3 |
| A0A5M7NEQ9 | Cluster: Nitrite reductase large subunit | *Enterobacterales* | 75.3 |
| A0A2V2BEC9 | Cluster: Assimilatory nitrite reductase (NAD(P)H) large subunit | *Pantoea* | 76.36 |
| A0A1X0W567 | Cluster: Nitrite reductase large subunit | *Rouxiella* | 77.88 |
| A0A6G9I851 | Cluster: Nitrite reductase large subunit | *Orbus* sp. IPMB12 | 77.66 |
| UPI0011BF5221 | Cluster: nitrite reductase large subunit | *Pantoea* sp. CCBC3-3-1 | 76.66 |
| A0A556RIT3 | Cluster: Nitrite reductase large subunit | *Gilliamella* | 74.91 |
| A0A1R4J5I6 | Cluster: Nitrite reductase [NAD(P)H] large subunit | *Vibrio* | 72.82 |
| A0A1B9MVL8 | Cluster: Nitrite reductase large subunit | *Gilliamella* | 75.03 |
| UPI0013596BEF | Cluster: nitrite reductase large subunit | unclassified Psychromonas | 72.59 |
| A0A1B9L8J9 | Cluster: Nitrite reductase large subunit | *Gilliamella apicola* | 74.79 |
| A0A095TED5 | Cluster: Nitrite reductase | *Tatumella* | 74.67 |
| A0A2S7VXZ8 | Cluster: Nitrite reductase large subunit | *Photobacterium* | 73.6 |
| A0A495REZ8 | Cluster: Assimilatory nitrite reductase (NAD(P)H) large subunit | *Orbus hercynius* | 75.15 |
| A0A2T3QB92 | Cluster: Nitric oxide reductase FIRd-NAD(+) reductase | *Photobacterium damselae* | 75.18 |
| A0A1X0WF55 | Cluster: Nitrite reductase large subunit | Gammaproteobacteria | 76.51 |
| A0A218TVB9 | Cluster: Nitrite reductase large subunit | *Vibrio* | 75.33 |
| A0A2T3NPM2 | Cluster: Nitrite reductase large subunit | *Photobacterium sanctipauli* | 74.85 |
| R9PFS3 | Cluster: Nitrite reductase | *Agarivorans* | 73.18 |

TABLE 4-continued

Examples of suitable NADH-dependent nitrite reductases, their UniProt Database Accession number (as can be found on the Uniprot website (uniprot.org/ as per 4 Oct. 2020), their description, the organism from which they may be derived, and their amino acid sequence identity with SEQ ID NO: 4 (large subunit encoded by nirB).

| UNIPROT DATABASE ACCESSION NUMBER | DESCRIPTION | ORGANISM | IDENTITY TO SEQ ID 4 [%] |
|---|---|---|---|
| A0A0B7J736 | Cluster: Nitrite reductase, large subunit, NAD(P)H-binding | *Photobacterium* | 73.6 |
| U4KF90 | Cluster: Nitrite reductase [NAD(P)H] large subunit | *Vibrio nigripulchritudo* | 73.78 |
| A0A1Y6IN13 | Cluster: Nitrite reductase [NAD(P)H] | *Vibrio mangrovi* | 73.54 |
| A0A1L9L1Z8 | Cluster: Nitrite reductase [NAD(P)H] | *Vibrionaceae* | 73.78 |
| A0A0A7RZE6 | Cluster: Assimilatory nitrite reductase (NAD(P)H) large subunit | *Frischella perrara* | 73.24 |
| A0A1Q9GSK0 | Cluster: Nitrite reductase large subunit | *Photobacterium* | 74.97 |
| UPI000200DAF9 | Cluster: nitrite reductase large subunit | *Vibrio furnissii* | 74.97 |
| A0A378PW16 | Cluster: Nitric oxide reductase FIRd-NAD(+) reductase | *Vibrionaceae* | 72.82 |
| A0A1B9JKB8 | Cluster: Nitrite reductase large subunit | *Gilliamella apicola* | 72.65 |
| D4ZBU5 | Cluster: Nitrite reductase [NAD(P)H], large subunit | *Shewanella violacea* (strain JCM 10179/ CIP 106290/LMG 19151/DSS12) | 72.4 |
| UPI00117F52C3 | Cluster: nitrite reductase large subunit | *Vibrio furnissii* | 74.97 |
| UPI0001B93571 | Cluster: nitrite reductase large subunit | *Vibrio furnissii* | 74.97 |
| A0A1B1NUU8 | Cluster: Nitrite reductase (NADH) | *Vibrionaceae* | 72.94 |
| A0A178KL92 | Cluster: Nitrite reductase large subunit | *Photobacterium* | 73.39 |
| A0A1T4RZM3 | Cluster: Nitrite reductase (NADH) large subunit | *Vibrio cincinnatiensis* | 74.37 |
| UPI0012ADB8F8 | Cluster: nitrite reductase large subunit | *Vibrio furnissii* | 74.97 |
| A0A418YIX2 | Cluster: Nitrite reductase large subunit | *Motilimonas* sp. PLHSC7-2 | 73 |
| Q6LS87 | Cluster: Putative nitrite reductase (NAD(P)H), large subunit | *Photobacterium* | 73.67 |
| A0A4R3I7X5 | Cluster: Nitrite reductase (NADH) large subunit | *Reinekea marinisedimentorum* | 73.72 |
| UPI0003F87F52 | Cluster: nitrite reductase large subunit | *Psychromonas* | 72.02 |
| UPI00037B4F3D | Cluster: nitrite reductase large subunit | *Uliginosibacterium gangwonense* | 70.2 |
| A0A2N7DBN5 | Cluster: Nitrite reductase large subunit | *Vibrio* sp. 10N.286.49.B3 | 73.06 |
| A0A484GE91 | Cluster: Nitrite reductase large subunit | *Candidatus Schmidhempelia bombi* str. *Bimp* | 72.16 |
| A0A2M8H0G2 | Cluster: Nitrite reductase (NAD(P)H) | unclassified Vibrio | 73.84 |
| U3CNX4 | Cluster: Nitrite reductase large subunit | *Vibrio* | 73.78 |
| UPI0010A63CB5 | Cluster: nitrite reductase large subunit | *Vibrio* sp. H11 | 73.12 |
| A0A090IJG5 | Cluster: Nitrite reductase (NAD(P)H) large subunit | *Moritella* | 71.92 |
| A0A2N0WYN5 | Cluster: Nitrite reductase (NAD(P)H) | *Psychromonas* | 72.87 |

TABLE 4-continued

Examples of suitable NADH-dependent nitrite reductases, their UniProt Database Accession number (as can be found on the Uniprot website (uniprot.org/ as per 4 Oct. 2020), their description, the organism from which they may be derived, and their amino acid sequence identity with SEQ ID NO: 4 (large subunit encoded by nirB).

| UNIPROT DATABASE ACCESSION NUMBER | DESCRIPTION | ORGANISM | IDENTITY TO SEQ ID 4 [%] |
|---|---|---|---|
| UPI000B356675 | Cluster: nitrite reductase large subunit | *Thaumasiovibrio subtropicus* | 73.12 |
| A0A1R4LRM2 | Cluster: Nitrite reductase [NAD(P)H] | *Vibrio* | 69.41 |
| UPI00082A845F | Cluster: nitrite reductase large subunit | *Erwinia* sp. ErVv1 | 72.27 |
| B8KAR6 | Cluster: Nitrite reductase (NAD(P)H), large subunit | *Vibrio* | 73.3 |
| A0A1G8E1S6 | Cluster: Assimilatory nitrite reductase (NAD(P)H) large subunit | *Vibrio xiamenensis* | 72.59 |
| A0A0C5WZ76 | Cluster: Nitrite reductase (NAD(P)H), large subunit | *Photobacterium* | 72.94 |
| A0A2G4AWG1 | Cluster: Nitrite reductase [NAD(P)H] | *Vibrionaceae* | 73.18 |

Nitrate/Nitrite Transporter

Preferably, the *Saccharomyces* yeast cell further comprises one or more genetic modifications that result in an increased transport of oxidized nitrogen source, such as nitrate or nitrite, into the yeast cell. More preferably the *Saccharomyces* yeast cell further comprising one or more genes encoding a nitrate and/or nitrite transporter.

Suitable transporters may include the sulphite transporters Ssu1 and SSu2 (as described by Cabrera et al in their article titled "Molecular Components of Nitrate and Nitrite Efflux in Yeast", published February 2014 Volume 13 Number 2 Eukaryotic Cell p. 267-278, herein incorporated by reference); and the nitrate/nitrite transporter YNT1 derived from *Pichia angusta* (also referred to as *Hansenula polymorpha*) and/or a functional homologues of one or more of such nitrate/nitrite transporters comprising an amino acid sequence with at least 40, 50, 60, 65, 70, 75, 80, 85, 90, 95, 98 or at least 99% amino acid sequence identity with one or more of the aforementioned nitrate/nitrite transporters; and/or functional homologues of one or more of such nitrate/nitrite transporters comprising an amino acid sequence having one or several substitutions, insertions and/or deletions as compared to the amino acid sequence of one or more of such aforementioned nitrate/nitrite transporters, wherein preferably the amino acid sequence of any of the above functional homologues has no more than 300, 250, 200, 150, 100, 75, 50, 40, 30, 20, 10 or 5 amino acid substitutions, insertions and/or deletions as compared to such aforementioned nitrate/nitrite transporter YNT1.

Preferably the *Saccharomyces* yeast cell comprises a nucleic acid sequence encoding the nitrate/nitrite transporter YNT1 derived from *Pichia angusta* and/or a functional homologues of such nitrate/nitrite transporter YNT1 comprising an amino acid sequence with at least 50, 60, 65, 70, 75, 80, 85, 90, 95, 98 or at least 99% amino acid sequence identity with nitrate/nitrite transporter YNT1; and/or functional homologues of such nitrate/nitrite transporter YNT1 comprising an amino acid sequence having one or several substitutions, insertions and/or deletions as compared to the amino acid sequence of one or more of such aforementioned nitrate/nitrite transporter YNT1, wherein preferably the amino acid sequence of any of the above functional homologues has no more than 300, 250, 200, 150, 100, 75, 50, 40, 30, 20, 10 or 5 amino acid substitutions, insertions and/or deletions as compared to such aforementioned nitrate/nitrite transporter YNT1.

Preferred nitrate/nitrite transporter hence include: nitrate/nitrite transporters comprising a polypeptide having an amino acid sequence of SEQ ID NO:6, as described herein; and/or functional homologues of SEQ ID NO:6 comprising an amino acid sequence with at least 40, 50, 60, 65, 70, 75, 80, 85, 90, 95, 98 or at least 99% amino acid sequence identity with SEQ ID NO:6; and/or functional homologues of SEQ ID NO:6 comprising an amino acid sequence having one or several substitutions, insertions and/or deletions as compared to the amino acid sequence of SEQ ID NO:6. Preferably the amino acid sequence of any of the above functional homologues has no more than 300, 250, 200, 150, 100, 75, 50, 40, 30, 20, 10 or 5 amino acid substitutions, insertions and/or deletions as compared to SEQ ID NO:6.

Suitably the *Saccharomyces* yeast cell may comprise a nucleotide sequence coding for an amino acid sequence of SEQ ID NO:6 or an amino acid sequence having one or several substitutions, insertions and/or deletions as compared to the amino acid sequence of any of SEQ ID NO:6. Preferably the amino acid sequence has no more than 300, 250, 200, 150, 100, 75, 50, 40, 30, 20, 10 or 5 amino acid substitutions, insertions and/or deletions as compared to SEQ ID NO:6 respectively.

Examples of suitable nitrite/nitrate transporters, their UniProt Database Accession number (as can be found on the Uniprot website (uniprot.org/as per 4 Oct. 2020), their description, the organism from which they may be derived, and their amino acid sequence identity with SEQ ID NO:6 are listed in Table 5 below.

TABLE 5

Examples of suitable nitrite/nitrate transporters, their UniProt Database Accession number (as can be found on the Uniprot website (uniprot.org/ as per 4 Oct. 2020), their description, the organism from which they may be derived, and their amino acid sequence identity with SEQ ID NO: 6.

| UNIPROT DATABASE ACCESSION NUMBER | DESCRIPTION | ORGANISM | IDENTITY TO SEQ ID 6 [%] |
|---|---|---|---|
| W1QLT0 | Cluster: Nitrate/nitrite transporter | *Ogataea* | 95.66 |
| W6MFQ5 | Cluster: Nitrate/nitrite transporter | *Kuraishia capsulata* CBS 1993 | 56.89 |
| A0A1E4TX12 | Cluster: Nitrate/nitrite transporter | *Pachysolen tannophilus* NRRL Y-2460 | 56.55 |
| A0A1E3NV96 | Cluster: Nitrate/nitrite transporter | *Wickerhamomyces anomalus* (strain ATCC 58044/CBS 1984/ NCYC 433/NRRL Y-366-8) | 56.52 |
| K0KNB9 | Cluster: Nitrate/nitrite transporter | *Wickerhamomyces ciferrii* (strain F-60-10/ ATCC 14091/CBS 111/JCM 3599/ NBRC 0793/NRRL Y-1031) | 56.46 |
| A0A0H5C0H7 | Cluster: Nitrate/nitrite transporter | *Cyberlindnera jadinii* (strain ATCC 18201/ CBS 1600/CCRC 20928/JCM 3617/ NBRC 0987/NRRL Y-1542) | 54.44 |
| A0A5P8N9I7 | Cluster: Nitrate/nitrite transporter | *Cyberlindnera americana* | 54.58 |
| A0A061BB65 | Cluster: CYFA0S24e00188g1_1 | *Cyberlindnera fabianii* | 52.72 |
| A0A060T893 | Cluster: Nitrate/nitrite transporter | *Blastobotrys adeninivorans* | 47.18 |
| B3WFS7 | Cluster: Nitrate/nitrite transporter | *Blastobotrys adeninivorans* | 47.79 |
| A0A261XZN8 | Cluster: Nitrate/nitrite transporter | *Bifiguratus adelaidae* | 47.49 |
| A0A0E9N9H8 | Cluster: Nitrate/nitrite transporter | *Saitoella complicata* (strain BCRC 22490/ CBS 7301/JCM 7358/ NBRC 10748/NRRL Y-17804) | 46.17 |
| A0A060T786 | Cluster: Nitrate/nitrite transporter | *Blastobotrys adeninivorans* | 43.91 |
| A0A0A1T938 | Cluster: Nitrate/nitrite transporter | *Torrubiella hemipterigena* | 42.57 |
| A0A3D8R1D7 | Cluster: Nitrate/nitrite transporter | *Coleophoma* | 42.66 |
| A0A370TMI7 | Cluster: Nitrate/nitrite transporter | *Venustampulla echinocandica* | 41.72 |
| A0A3N4HFN0 | Cluster: Nitrate/nitrite transporter | *Ascobolus immersus* RN42 | 42.16 |
| A0A167RLM4 | Cluster: Nitrate/nitrite transporter | *Cordyceps fumosorosea* ARSEF 2679 | 40.04 |
| A0A179I4H5 | Cluster: Nitrate/nitrite transporter | *Akanthomyces lecanii* | 40.94 |
| A0A0G2E479 | Cluster: Nitrate/nitrite transporter | *Phaeomoniella chlamydospora* | 42.33 |
| A0A6A6CV94 | Cluster: Nitrate/nitrite transporter | *Zasmidium cellare* ATCC 36951 | 42.91 |
| S3CRP8 | Cluster: Nitrate/nitrite transporter | *Glarea lozoyensis* | 40.4 |
| A0A1B8DXT4 | Cluster: Nitrate/nitrite transporter | unclassified *Pseudogymnoascus* | 42.74 |
| A0A094B0S5 | Cluster: Nitrate/nitrite transporter | *Pseudogymnoascus* | 42.94 |
| A0A6A6WTZ3 | Cluster: Nitrate/nitrite transporter | *Melanomma pulvis-pyrius* CBS 109.77 | 42.51 |
| G3JS45 | Cluster: Nitrate/nitrite transporter | *Cordyceps militaris* | 40.65 |

TABLE 5-continued

Examples of suitable nitrite/nitrate transporters, their UniProt Database Accession number (as can be found on the Uniprot website (uniprot.org/ as per 4 Oct. 2020), their description, the organism from which they may be derived, and their amino acid sequence identity with SEQ ID NO: 6.

| UNIPROT DATABASE ACCESSION NUMBER | DESCRIPTION | ORGANISM | IDENTITY TO SEQ ID 6 [%] |
|---|---|---|---|
| A0A0E9NCH7 | Cluster: Nitrate/nitrite transporter | *Saitoella complicata* (strain BCRC 22490/ CBS 7301/JCM 7358/ NBRC 10748/NRRL Y-17804) | 44.27 |
| A0A0C3CTX3 | Cluster: Nitrate/nitrite transporter | *Oidiodendron maius* Zn | 43.15 |
| A0A6G1J7V7 | Cluster: Nitrate transporter-like protein | *Lentithecium fluviatile* CBS 122367 | 42.63 |
| A0A4U0XSZ7 | Cluster: Nitrate/nitrite transporter | *Cryomyces minteri* | 41.8 |
| UPI000CE1C7E3 | Cluster: nitrate transporter-like | *Quercus suber* | 41.33 |
| A0A6A5XQJ5 | Cluster: Nitrate/nitrite transporter | *Aaosphaeria arxii* CBS 175.79 | 42.24 |
| A0A1W5CWS1 | Cluster: Nitrate/nitrite transporter | *Lasallia pustulata* | 43.11 |
| A0A6A6R7R9 | Cluster: Nitrate/nitrite transporter | *Mytilinidiaceae* | 43.99 |
| U1GKS4 | Cluster: Nitrate/nitrite transporter | *Endocarpon pusillum* (strain Z07020/HMAS-L-300199) | 42.43 |
| D5GLI8 | Cluster: Nitrate/nitrite transporter | *Tuber melanosporum* (strain Mel28) | 41.75 |
| A0A5J5EIC4 | Cluster: Nitrate/nitrite transporter | *Sphaerosporella brunnea* | 41.7 |
| UPI00144AC6B7 | Cluster: nitrate transporter | *Lindgomyces ingoldianus* | 42.6 |
| A0A6A6RHP6 | Cluster: Nitrate/nitrite transporter | *Massarina eburnea* CBS 473.64 | 42.6 |
| A0A6A6JM23 | Cluster: Nitrate/nitrite transporter | *Westerdykella ornata* | 42.63 |
| A0A317SYP8 | Cluster: Nitrate/nitrite transporter | *Tuber* | 41.34 |
| A0A232LMW8 | Cluster: Nitrate/nitrite transporter | *Elaphomyces granulatus* | 43.09 |
| A0A1L7WDP7 | Cluster: Nitrate/nitrite transporter | *Phialocephala subalpina* | 42.04 |
| A0A6A5UCT1 | Cluster: Nitrate/nitrite transporter | *Byssothecium circinans* | 43.38 |
| A0A6A6BJV5 | Cluster: Nitrate/nitrite transporter | *Aplosporella prunicola* CBS 121167 | 44.08 |
| A0A6G1LEQ8 | Cluster: Nitrate transporter | *Teratosphaeria nubilosa* | 41.68 |
| S3DBU1 | Cluster: Nitrate/nitrite transporter | *Glarea lozoyensis* | 43.51 |
| A0A4U0TQA4 | Cluster: Nitrate/nitrite transporter | *Hortaea thailandica* | 40.68 |
| A0A4U0X4U1 | Cluster: Nitrate/nitrite transporter | *Friedmanniomyces* | 40.28 |
| A0A507R2R1 | Cluster: Nitrate/nitrite transporter | *Monascus purpureus* | 41.84 |
| A0A2V1DKP2 | Cluster: Nitrate/nitrite transporter | *Periconia macrospinosa* | 41.46 |
| A0A1L9RJV0 | Cluster: Nitrate/nitrite transporter | *Aspergillus wentii* DTO 134E9 | 42.54 |
| A0A167P4D7 | Cluster: Nitrate/nitrite transporter | *Sporothrix insectorum* RCEF 264 | 41.12 |
| UPI000CE20498 | Cluster: nitrate transporter-like | *Quercus suber* | 42.71 |
| A0A4Z1P351 | Cluster: Nitrate/nitrite transporter | *Venturia* | 41.63 |
| A0A6G1K4M7 | Cluster: Nitrate transporter-like protein | *Pleomassaria siparia* CBS 279.74 | 42.16 |
| M7U767 | Cluster: Nitrate/nitrite transporter | *Sclerotiniaceae* | 42.65 |
| A0A0D2AUR8 | Cluster: Nitrate/nitrite transporter | *Verruconis gallopava* | 41.41 |
| A0A6G1H5R5 | Cluster: Nitrate transporter | *Aulographum hederae* CBS 113979 | 41.73 |

TABLE 5-continued

Examples of suitable nitrite/nitrate transporters, their UniProt Database Accession number (as can be found on the Uniprot website (uniprot.org/ as per 4 Oct. 2020), their description, the organism from which they may be derived, and their amino acid sequence identity with SEQ ID NO: 6.

| UNIPROT DATABASE ACCESSION NUMBER | DESCRIPTION | ORGANISM | IDENTITY TO SEQ ID 6 [%] |
|---|---|---|---|
| A0A1Y2TEF0 | Cluster: Nitrate/nitrite transporter | unclassified Hypoxylon | 41.77 |
| A0A177BV64 | Cluster: Nitrate/nitrite transporter | *Paraphaeosphaeria sporulosa* | 41.75 |
| A0A6A5WR45 | Cluster: Nitrate/nitrite transporter | *Amniculicola lignicola* CBS 123094 | 42.63 |
| A0A6G1KNX3 | Cluster: Nitrate transporter-like protein | *Pleomassaria siparia* CBS 279.74 | 41.41 |
| W9WHT3 | Cluster: Nitrate/nitrite transporter | *Herpotrichiellaceae* | 42.14 |
| A0A2T2P8J8 | Cluster: Nitrate/nitrite transporter | *Corynespora cassiicola Philippines* | 43.06 |
| A0A6A6T246 | Cluster: Nitrate/nitrite transporter | *Lophiostoma macrostomum* CBS 122681 | 41.41 |
| A0A2P8ABJ3 | Cluster: Nitrate/nitrite transporter | *Elsinoe australis* | 42.25 |
| A0A1Y1ZNY9 | Cluster: Nitrate/nitrite transporter | *Clohesyomyces aquaticus* | 40.77 |
| W2RSI4 | Cluster: Nitrate/nitrite transporter | *Cyphellophora europaea* CBS 101466 | 41.24 |
| A0A2V1E4S3 | Cluster: Nitrate/nitrite transporter | *Periconia macrospinosa* | 41.41 |
| A0A6A5V026 | Cluster: Nitrate/nitrite transporter | *Bimuria novae-zelandiae* CBS 107.79 | 41.15 |
| A0A2K1QG31 | Cluster: Nitrate/nitrite transporter | *Elsinoaceae* | 42.25 |
| A0A094A2I4 | Cluster: Nitrate/nitrite transporter | *Pseudogymnoascus* sp. VKM F-4281 (FW-2241) | 43.54 |
| A0A6A6XX03 | Cluster: Nitrate/nitrite transporter | *Melanomma pulvis-pyrius* CBS 109.77 | 42.07 |
| A0A2J5HKF9 | Cluster: Nitrate/nitrite transporter | *Aspergillus* | 40.56 |
| A0A6A6IDB6 | Cluster: Nitrate/nitrite transporter | *Trematosphaeria pertusa* | 42.45 |
| A0A6A5ST79 | Cluster: Nitrate/nitrite transporter | *Clathrospora elynae* | 41.85 |
| A0A3N4JV10 | Cluster: Nitrate/nitrite transporter | *Choiromyces venosus* 120613-1 | 42.06 |
| A0A6A5XFW9 | Cluster: Nitrate/nitrite transporter | *Aaosphaeria arxii* CBS 175.79 | 41.43 |
| A0A553IBL5 | Cluster: Nitrate/nitrite transporter | *Xylaria flabelliformis* | 40.24 |
| R7Z451 | Cluster: Nitrate/nitrite transporter | *Coniosporium apollinis* (strain CBS 100218) | 40.61 |
| A0A139I046 | Cluster: Nitrate/nitrite transporter | *Pseudocercospora musae* | 40.24 |
| A0A2T2NBP3 | Cluster: Nitrate/nitrite transporter | *Corynespora cassiicola Philippines* | 41.84 |
| A0A177E3H1 | Cluster: Nitrate/nitrite transporter | *Alternaria* | 42.21 |
| B0XPC3 | Cluster: Nitrate/nitrite transporter | *Neosartorya fumigata* | 42.89 |
| A0A150V198 | Cluster: Nitrate/nitrite transporter | *Acidomyces richmondensis* BFW | 42.08 |
| A0A3N4KQT8 | Cluster: Nitrate/nitrite transporter | *Morchella conica* CCBAS932 | 40.44 |
| A0A1Y2DSQ4 | Cluster: Nitrate/nitrite transporter | *Pseudomassariella vexata* | 41.05 |
| A0A2V1BSJ8 | Cluster: Nitrate/nitrite transporter | *Helotiales incertae sedis* | 42.04 |
| A0A1V1TKZ5 | Cluster: Nitrate/nitrite transporter | Fungi | 40.24 |
| K1WJ63 | Cluster: Nitrate/nitrite transporter | *Marssonina brunnea* f. sp. *multigermtubi* (strain MB_m1) | 42.06 |
| A0A6A6E950 | Cluster: Nitrate/nitrite transporter | *Zopfia rhizophila* CBS 207.26 | 41.92 |

TABLE 5-continued

Examples of suitable nitrite/nitrate transporters, their UniProt Database Accession number (as can be found on the Uniprot website (uniprot.org/ as per 4 Oct. 2020), their description, the organism from which they may be derived, and their amino acid sequence identity with SEQ ID NO: 6.

| UNIPROT DATABASE ACCESSION NUMBER | DESCRIPTION | ORGANISM | IDENTITY TO SEQ ID 6 [%] |
|---|---|---|---|
| A0A2K1R263 | Cluster: Nitrate/nitrite transporter | *Sphaceloma murrayae* | 41.83 |
| A0A2S7Q2X6 | Cluster: Nitrate/nitrite transporter | unclassified *Rutstroemia* | 42.32 |

Co-Factors

Preferably the *Saccharomyces* yeast cell further comprises suitable co-factors to enhance the activity of the above mentioned NADH-dependent nitrate reductase and/or NADH-dependent nitrite reductase. Preferred cofactors include flavin adenine dinucleotide (FAD), heme prosthetic groups, and/or molybdenum cofactor (MoCo). Preferably the *Saccharomyces* yeast cell may therefore further comprise one or more genes encoding enzymes for the synthesis of one or more of flavin adenine dinucleotide (FAD), heme prosthetic groups, and/or molybdenum cofactor (MoCo). For example, the *Saccharomyces* yeast cell may comprise one or more genes encoding for an enzyme having FAD synthase activity.

Preferably the *Saccharomyces* yeast cell is therefore a *Saccharomyces* yeast cell further comprising:

- a nucleic acid sequence encoding a GTP 3',8-cyclase;
- a nucleic acid sequence encoding a Cyclic pyranopterin monophosphate synthase;
- a nucleic acid sequence encoding a Molybdopterin synthase catalytic subunit;
- a nucleic acid sequence encoding a Molybdopterin synthase sulfur carrier subunit;
- a nucleic acid sequence encoding a Molybdopterin adenylyltransferase, and/or
- a nucleic acid sequence encoding a Molybdopterin-synthase adenylyltransferase and/or a Molybdopterin molybdenumtransferase.

A suitable set of genes encoding enzymes for the synthesis of a molybdenum cofactor (MoCo) is described in PCT patent application PCT/NL2020/050241, published as WO2020/209718 in the name of the Technische Universiteit Delft. For example, the *Saccharomyces* yeast cell may suitably further comprise a recombinant Moco pathway gene set that allows the yeast to produce Molybdenum co-factor, wherein the Moco pathway gene set comprises:

- a gene having at least 70% sequence identity with SEQ ID NO:1 as described in WO2020/209718 and encoding a GTP 3',8-cyclase;
- a gene having at least 70% sequence identity with SEQ ID NO:2 as described in WO2020/209718 and encoding a Cyclic pyranopterin monophosphate synthase;
- a gene having at least 70% sequence identity with SEQ ID NO:3 as described in WO2020/209718 and encoding a Molybdopterin synthase catalytic subunit;
- a gene having at least 70% sequence identity with SEQ ID NO:4 as described in WO2020/209718 and encoding a Molybdopterin synthase sulfur carrier subunit;
- a gene having at least 70% sequence identity with SEQ ID NO:5 as described in WO2020/209718 and encoding a Molybdopterin adenylyltransferase, and/or
- a gene having at least 70% sequence identity with SEQ ID NO:6 as described in WO2020/209718 and encoding a Molybdopterin-synthase adenylyltransferase and/or a Molybdopterin molybdenumtransferase. Further preferences are as described in WO2020/209718. The contents of WO2020/209718 and SEQ ID NO: 1, SEQ ID NO: 2, SEQ ID NO: 3, SEQ ID NO: 4, SEQ ID NO: 5 and SEQ ID NO: 6 as described in WO2020/209718 are incorporated herein by reference.

Deletion or Disruption of Glycerol 3-Phosphate Phosphohydrolase and/or Glycerol 3-Phosphate Dehydrogenase Suitably, the *Saccharomyces* yeast cell may further comprise a deletion or disruption of one or more endogenous nucleotide sequence encoding a glycerol 3-phosphate phosphohydrolase gene and/or encoding a glycerol 3-phosphate dehydrogenase gene.

Preferably enzymatic activity needed for the NADH-dependent glycerol synthesis in the yeast cell is reduced or deleted. The reduction or deletion of the enzymatic activity of glycerol 3-phosphate phosphohydrolase and/or glycerol 3-phosphate dehydrogenase can be achieved by modifying one or more genes encoding a NAD-dependent glycerol 3-phosphate dehydrogenase (GPD) and/or one or more genes encoding a glycerol phosphate phosphatase (GPP), such that the enzyme is expressed considerably less than in the wild-type or such that the gene encodes a polypeptide with reduced activity. Such modifications can be carried out using commonly known biotechnological techniques, and may in particular include one or more knock-out mutations or site-directed mutagenesis of promoter regions or coding regions of the structural genes encoding GPD and/or GPP. Alternatively, yeast strains that are defective in glycerol production may be obtained by random mutagenesis followed by selection of strains with reduced or absent activity of GPD and/or GPP. *S. cerevisiae* GPD1, GPD2, GPP1 and GPP2 genes are shown in WO2011010923, and are disclosed in SEQ ID NO: 24-27 of that application.

Preferably at least one gene encoding a GPD and/or at least one gene encoding a GPP is entirely deleted, or at least a part of the gene is deleted that encodes a part of the enzyme that is essential for its activity. In particular, good results have been achieved with a *S. cerevisiae* cell, wherein the open reading frames of the GPD1 gene and of the GPD2 gene have been inactivated. Inactivation of a structural gene (target gene) can be accomplished by a person skilled in the art by synthetically synthesizing or otherwise constructing a DNA fragment consisting of a selectable marker gene flanked by DNA sequences that are identical to sequences that flank the region of the host cell's genome that is to be deleted. In particular, good results have been obtained with the inactivation of the GPD1 and GPD2 genes in *Saccha-*

*romyces cerevisiae* by integration of the marker genes kanMX and hphMX4. Subsequently this DNA fragment is transformed into a host cell. Transformed cells that express the dominant marker gene are checked for correct replacement of the region that was designed to be deleted, for example by a diagnostic polymerase chain reaction or Southern hybridization.

Thus, in the *Saccharomyces* yeast cells of the invention, glycerol 3-phosphate phosphohydrolase activity and/or glycerol 3-phosphate dehydrogenase activity is advantageously reduced. In the cells of the invention, the specific glycerolphosphate dehydrogenase activity is preferably reduced by at least a factor 0.8, 0.5, 0.3, 0.1, 0.05 or 0.01 as compared to a strain which is genetically identical except for the genetic modification causing the reduction in specific activity, preferably under anaerobic conditions. Glycerolphosphate dehydrogenase activity may be determined as described by Overkamp et al. (2002, Yeast 19:509-520).

Glycerol Dehydrogenase, Dihydroxyacetone Kinase and Glycerol Transporter

Preferably the *Saccharomyces* yeast cell may further comprise:

- one or more nucleic acid sequences encoding a glycerol dehydrogenase; and/or
- one or more nucleic acid sequences encoding a dihydroxyacetone kinase; and/or
- one or more nucleic acid sequences encoding a glycerol transporter More preferably the *Saccharomyces* yeast cell may comprise: one or more nucleic acid sequences encoding a glycerol dehydrogenase; and/or one or more nucleic acid sequences encoding a dihydroxyacetone kinase; and/or one or more nucleic acid sequences encoding a glycerol transporter, each as described and exemplified in WO 2019/063507 A1 (hereby incorporated by reference).

The enzyme glycerol dehydrogenase catalyzes at least the following reaction:

$$glycerol+NAD+<->glycerone+NADH+H^+$$

Thus, the two substrates of this enzyme are glycerol and $NAD^+$, whereas its three products are glycerone, NADH, and $H^+$. Glycerone and dihydroxyacetone are herein synonyms. This enzyme belongs to the family of oxidoreductases, specifically those acting on the CH—OH group of donor with $NAD^+$ or $NADP^+$ as acceptor. The systematic name of this enzyme class is glycerol:NAD+2-oxidoreductase. Other names in common use include glycerin dehydrogenase, and NAD+-linked glycerol dehydrogenase. This enzyme participates in glycerolipid metabolism. Structural studies have shown that the enzyme is zinc-dependent with the active site lying between the two domains of the protein. In an embodiment the enzyme having glycerol dehydrogenase activity is preferably a $NAD^+$ linked glycerol dehydrogenase (EC 1.1.1.6). Such enzyme may be from bacterial origin or for instance from fungal origin. An example is gldA from *E. coli*. The enzyme having glycerol dehydrogenase activity may also be a $NADP^+$ linked glycerol dehydrogenase (EC 1.1.1.72). When a recombinant yeast is used for ethanol production, which typically takes place under anaerobic conditions, $NAD^+$ linked glycerol dehydrogenases are preferred.

Preferably the *Saccharomyces* yeast cell may also comprise a nucleic acid coding for an enzyme having dihydroxyacetone kinase activity. The *Saccharomyces* yeast cell preferably comprises one or more genes coding for an enzyme having dihydroxyacetone kinase activity with EC codes E.C. 2.7.1.28 and/or E.C. 2.7.1.29. The enzyme dihydroxyacetone kinase catalyzes at least one of the following reactions:

ATP+D-glyceraldehyde<=>ADP+D-glyceraldehyde 3-phosphate or

EC 2.7.1.29: ATP+glycerone<=>ADP+glycerone phosphate

This family of enzymes may include examples of the single chain form of dihydroxyacetone kinase (also called glycerone kinase) that uses ATP (EC 2.7.1.29 or EC 2.7.1.28) as the phosphate donor, rather than a phosphoprotein as in *Escherichia coli*. This form has separable domains homologous to the K and L subunits of the *E. coli* enzyme, and is found in yeasts and other eukaryotes and in some bacteria, including *Citrobacter freundii*. The member from tomato has been shown to phosphorylate dihydroxyacetone, 3,4-dihydroxy-2-butanone, and some other aldoses and ketoses. Members from mammals have been shown to catalyse both the phosphorylation of dihydroxyacetone and the splitting of ribonucleoside diphosphate-X compounds among which FAD is the best substrate. In yeast there are two isozymes of dihydroxyacetone kinase (Dak1 and Dak2). In an embodiment the *Saccharomyces* yeast cell may comprises endogenous DAK which is overexpressed. The enzyme having dihydroxy acetone kinase activity may be encoded by an endogenous gene, e.g. a DAK1, which endogenous gene is preferably placed under control of a constitutive promoter. The recombinant cell may comprise a genetic modification that increases the specific activity of dihydroxyacetone kinase in the cell.

In an embodiment the *Saccharomyces* yeast cell may further comprise one or more genes coding for a glycerol transporter or an enzyme having an amino acid sequence listed for such in WO 2019/063507 A1 (i.e. WO 2019/063507 A1 refers to SEQ ID NO: 16 and SEQ ID NO: 17 therein for the glycerol transporter which are incorporated by reference herewith) or a functional homologue thereof having a sequence identity of at least 50%, preferably at least 60%, 70%, 75%, 80%. 85%, 90%, 95%, or at least 99%. Any glycerol that is externally available in the medium (e.g. from the backset in corn mash) or secreted after internal cellular synthesis may be transported into the cell and converted to ethanol.

Fermentation Process

The invention further provides an anaerobic fermentation process for the production of a fermentation product, comprising fermenting of a feed, which feed comprises an oxidized nitrogen source and a fermentable carbon source, using a *saccharomyces* yeast cell as described above.

The fermentable carbon source preferably comprises or is consisting of one or more fermentable carbohydrates. More preferably, the fermentable carbon source comprises one or more mono-saccharides, disaccharides and/or polysaccharides. For example, the fermentable carbon source may comprise one or more carbohydrates selected from the group consisting of glucose, fructose, sucrose, maltose, xylose, arabinose, galactose, mannose and trehalose. The fermentable carbon source, preferably comprising or consisting of one or more carbohydrates, may suitably be obtained from starch, cellulose, hemicellulose lignocellulose, and/or pectin. Suitably the fermentable carbon source may be in the form of a, preferably aqueous, slurry, suspension, or a liquid.

The concentration of fermentable carbohydrate, such as for example glucose, during fermentation is preferably equal to or more than 80 g/L. That is, the initial concentration of glucose at the start of the fermentation, is preferably equal to or more than 80 g/L, more preferably equal to or more than 90 g/L, even more preferably equal to or more than 100 g/L, still more preferably equal to or more than 110 g/L, yet even more preferably equal to or more than 120 g/L, equal to or more than 130 g/L, equal to or more than 140 g/L, equal to or more than 150 g/L, equal to or more than 160 g/L, equal to or more than 170 g/L, or equal to or more than 180 g/L. The start of the fermentation may be the moment when the fermentable fermentable carbohydrate is brought into contact with the recombinant cell of the invention.

The fermentable carbon source may be prepared by contacting starch, lignocellulose, and/or pectin with an enzyme composition, wherein one or more mono-saccharides, disaccharides and/or polysaccharides are produced, and wherein the produced mono-saccharides, disaccharides and/or polysaccharides are subsequently fermented to give a fermentation product.

In one embodiment the fermentable carbohydrate is, or is comprised by a biomass hydrolysate, such as a corn stover or corn fiber hydrolysate. Such biomass hydrolysate may in its turn comprise, or be derived from corn stover and/or corn fiber.

By a "hydrolysate" is herein understood a polysaccharide-comprising material (such as corn stover, corn starch, corn fiber, or lignocellulosic material, which polysaccharides have been depolymerized through the addition of water to form mono and oligosaccharide sugars. Hydrolysates may be produced by enzymatic or acid hydrolysis of the polysaccharide-containing material.

A biomass hydrolysate may be a lignocellulosic biomass hydrolysate. Lignocellulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof. Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert. In addition, pectins and other pectic substances such as arabinans may make up considerably proportion of the dry mass of typically cell walls from non-woody plant tissues (about a quarter to half of dry mass may be pectins). Lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

In addition to the fermentable carbon source, the fermentation feed and/or fermentation medium also comprises an oxidized nitrogen source. Examples of oxidized nitrogen sources include alkali metal salts and alkaline earth metal salts of nitrite and nitrate, such as for example sodium nitrate, sodium nitrite, potassium nitrate, potassium nitrite, calcium nitrate, calcium nitrite, magnesium nitrate and/or magnesium nitrite. The oxidized nitrogen source may also be present as a dissolved or dissociated salt, that it, it may also be present as a nitrite $NO_2^-$ ion or nitrate $NO_3^-$ ion. Suitably the oxidized nitrogen source, such as a nitrate salt or a nitrite salt, may be present in combination with ammonium. For example ammonium nitrate or ammonium nitrite may be used as an oxidized nitrogen source. However, ammonium nitrate can be explosive and would need to be provided in a composition mitigating such risk.

Another example of an oxidized nitrogen source is the so-called Urea Ammonium Nitrate, also abbreviates as UAN (UAN is for example supplied by producer YARA in Norway). UAN provides four distinct forms of nitrogen: NH4, NO3, Urea and NH3. Even though UAN still comprises urea, the percentage urea used can be greatly reduced by using UAN instead of urea. Advantageously, though UAN contains ammonium nitrate, UAN is not explosive and is not classified as a "dangerous good" during air, land or sea transport.

The anaerobic fermentation process produces one or more fermentation products. Suitable fermentation products include alcohols and organic acids. Preferred fermentation products include ethanol, butanol, lactic acid and succinic acid. In addition, the process also provides dried distillers grains (DDG).

Such dried distillers grains (DDG) may advantageously be used as animal feed, for example as part of the feed for cattle, pigs or poultry. Due to the use of the *Saccharomyces* yeast cell according to the invention, the quality of the dried distillers grains (DDG) may be improved. The amount of ethyl carbamate and/or lactic acid therein may be reduced and the type and concentration of nitrogen-containing components therein may be improved. Advantageously the dried distillers grains may comprise no or a reduced amount of urethane (ethyl carbamate).

Advantageously the invention provides a product comprising distillers grains comprising equal to or less than 17 ng/g of ethyl carbamate, more preferably equal to or less than 10 ng/g of ethyl carbamate, even more preferably equal to or less than 5 ng/g and most preferably equal to or less than 1 ng/g. There is no lower limit, but practical reasons the distillers grains may comprise equal to or more than 0.001 ng/g. The distillers grains can be wet or dried and can be with or without solubles.

All patent and literature references cited in the present specification are hereby incorporated by reference in their entirety.

The following examples are offered for illustrative purposes only, and are not intended to limit the scope of the present invention in any way.

EXAMPLES

In order to incorporate an NADH-dependent nitrate and/or nitrite assimilation pathway in a *Saccharomyces* yeast cell, alternative gene combinations are to be tested. For a number of enzymes in the pathway, i.e. nitrate and/or nitrite transporters, NADH dependent nitrate reductase and/or NADH dependent nitrite reductase, multiple alternative genes are to be tested that could allow the *Saccharomyces* yeast cell to convert an external oxidized nitrogen source into intracellular ammonia, in parallel with a conversion of pentose and/or hexose sugars into ethanol, under anaerobic conditions.

Unless indicated otherwise, the methods used are standard biochemical techniques. Examples of suitable general methodology textbooks include Sambrook et al., Molecular Cloning, a Laboratory Manual (1989) and Ausubel et al., Current Protocols in Molecular Biology (1995), John Wiley & Sons, Inc.

Prophetic Example 1

Ethanol Red, a commercial *Saccharomyces cerevisiae* yeast available from LeSaffre (France) can be used to express various NADH-dependent nitrate reductases (EC 1.7.1.1), NADH-dependent nitrite reductases (EC 1.7.1.15) and/or a nitrate transporter and/or a molybdenum cofactor pathway. For example, this modified yeast can contain a NADH-dependent nitrate reductases from *Zea mays* (SEQ ID NO:1), NADH-dependent nitrite reductases from *E. coli* coding for the small subunit NirD (SEQ ID NO:3) and large subunit NirB (SEQ ID NO:4), and Siroheme synthase CysG from *E. coli* (SEQ ID NO:22) or overexpression of the *S. cerevisiae* MET8 Bifunctional dehydrogenase and ferrochelatase (YBR213W) (SEQ ID NO:23):

Furthermore, this modified yeast can express a functional pathway to produce the molybdopterin cofactor. The genes and corresponding enzymes for molybdopterin pathway from GTP can be downloaded from the MetaCyc website (metacyc.org as available on 5 Oct. 2020).

The *E. coli* molybdopterin pathway has been described by Leimkühler S, Wuebbens M M, Rajagopalan K V., in their article "*The History of the Discovery of the Molybdenum Cofactor and Novel Aspects of its Biosynthesis in Bacteria*", published in Coord Chem Rev. (2011); Vol. 255(9-10): pages 1129-1144. (doi:10.1016/j.ccr.2010.12.003). The following enzymes of the molybdopterin cofactor pathway can be expressed: MoaA (SEQ ID NO:7), MoaC (SEQ ID NO:8), MoaD (SEQ ID NO:9), MoaE (SEQ ID NO:10), MoeB (SEQ ID NO:19), MogA (SEQ ID NO:20), MoeA (SEQ ID NO:18), MobA (SEQ ID NO:11), MobB (SEQ ID NO:12), MocA (SEQ ID NO13) and/or IscS (SEQ ID NO:21) and/or ModA, ModB and/or ModC for molybdate transport (SEQ ID NO:14, SEQ ID NO:15 and SEQ ID NO:16, respectively) and/or ModE (SEQ ID NO:17).

This modified yeast can in addition or alternatively express a functional pathway to produce the molybdopterin cofactor from plants as described for example by Mendel R R, in its article titled "*Biology of the molybdenum cofactor*", published in J Exp Bot. (2007); Vol. 58(9): pages 2289-2296. (doi: 10.1093/jxb/erm024. Epub 2007 Mar. 9. PMID: 17351249.). Suitably the following enzymes from *Arabidopsis thaliana* can be expressed in yeast to produce the Cnx1 (SEQ ID NO:24), Cnx2 (SEQ ID NO: 25), Cnx3 (SEQ ID NO: 26), Cnx5=MOCS3 (SEQ ID NO:27), Cnx6=Moc2B (SEQ ID NO:28), Cnx7=Moc2A (SEQ ID NO:29):

```
SEQ ID NO: 23 (MET8):
>sp|P15807|MET8_YEAST Siroheme biosynthesis protein MET8 OS = Saccharomyces
cerevisiae (strain ATCC 204508/S288c) OX = 559292 GN = MET8 PE = 1 SV = 1
MVKSLQLAHQLKDKKILLIGGGEVGLTRLYKLIPTGCKLTLVSPDLHKSIIPKFGKFIQNEDQPDYREDAKRF

INPNWDPTKNEIYEYIRSDFKDEYLDLEDENDAWYIIMTCIPDHPESARIYHLCKERFGKQQLVNVADKPDL

CDFYFGANLEIGDRLQILISTNGLSPRFGALVRDEIRNLFTQMGDLALEDAVVKLGELRRGIRLLAPDDKDV

KYRMDWARRCTDLFGIQHCHNIDVKRLLDLFKVMFQEQNCSLQFPPRERLLSEYCSS

SEQ ID NO: 22 (CysG):
>sp|P0AEA8|CYSG_ECOLI Siroheme synthase OS = Escherichia coli (strain K12)
OX = 83333 GN = cysG PE = 1 SV = 1
MDHLPIFCQLRDRDCLIVGGGDVAERKARLLLDAGARLTVNALAFIPQFTAWADAGMLTLVEGPFDESLL

DTCWLAIAATDDDALNQRVSEAAEARRIFCNVVDAPKAASFIMPSIIDRSPLMVAVSSGGTSPVLARLLRE

KLESLLPLHLGQVAKYAGQLRGRVKQQFATMGERRRFWEKLFVNDRLAQSLANNDQKAITETTEQLINEP

LDHRGEVVLVGAGPGDAGLLTLKGLQQIQQADVVVYDRLVSDDIMNLVRRDADRVFVGKRAGYHCVPQ

EEINQILLREAQKGKRVVRLKGGDPFIFGRGGEELETLCNAGIPFSVVPGITAASGCSAYSGIPLTHRDYAQ

SVRLITGHLKTGGELDWENLAAEKQTLVFYMGLNQAATIQQKLIEHGMPGEMPVAIVENGTAVTQRVIDG

TLTQLGELAQQMNSPSLIIIGRVVGLRDKLNWFSNH
```

SEQ ID NO: 24 (CNX1):
>sp|Q39054|CNX1_ARATH Molybdopterin biosynthesis protein CNX1 OS = *Arabidopsis thaliana* OX = 3702 GN = CNX1 PE = 1 SV = 2
MEGQGCCGGGGGKTEMIPTEEALRIVFGVSKRLPPVIVSLYEALGKVLAEDIRAPDPLPP

YPASVKDGYAVVASDGPGEYPVITESRAGNDGLGVTVTPGTVAYVTTGGPIPDGADAVVQ

VEDTKVIGDVSTESKRVKILIQTKKGTDIRRVGCDIEKDATVLTTGERIGASEIGLLATA

GVTMVKVYPMPIVAILSTGDELVEPTAGTLGRGQIRDSNRAMLVAAVMQQQCKVVDLGIV

RDDRKELEKVLDEAVSSGVDIILTSGGVSMGDRDFVKPLLEEKGKVYFSKVLMKPGKPLT

FAEIRAKPTESMLGKTVLAFGLPGNPVSCLVCFNIFVVPTIRQLAGWTSPHPLRVRLRLQ

EPIKSDPIRPEFHRAIIKWKDNDGSGTPGFVAESTGHQMSSRLLSMRSANALLELPATGN

VLSAGSSVSAIIVSDISAFSIDKKASLSEPGSIRKEKKYDEVPGPEYKVAILTVSDTVSA

GAGPDRSGPRAVSVVDSSSEKLGGAKVVATAVVPDEVERIKDILQKWSDVDEMDLILTLG

GTGFTPRDVTPEATKKVIERETPGLLFVMMQESLKITPFAMLSRSAAGIRGSTLIINMPG

NPNAVAECMEALLPALKHALKQIKGDKREKHPKHIPHAEATLPTDTWDQSYKSAYETGEK

KEEAGCSCTH

SEQ ID NO: 25 (CNX2):
>sp|Q39055|CNX2_ARATH GTP 3',8-cyclase, mitochondrial OS = *Arabidopsis thaliana* OX = 3702 GN = CNX2 PE = 1 SV = 1
MRRCFSKITDCHLGFKNSNFLLVGSEVGSGSVTRTITTTTSERLFSSSYAAHQVDQIKDN

PVSDMLIDKFGRLHTYLRISLTERCNLRCQYCMPSEGVELTPKPQLLSQSEIVRLAGLFV

SAGVNKIRLTGGEPTVRKDIEEICLQLSSLKGLKNLAITTNGITLAKKLPRLKECGLDSL

NISLDTLVPAKFEFLTRRKGHDRVMKSIDTAIELGYNPVKVNCVIMRGLNDDEICDFVEL

TRDKPINVRFIEFMPFDGNVWNVKKLVPYAEVMDKVVKRFPSIKRMQDHPTETAKNFTID

GHCGSVSFITSMTEHFCAGCNRLRLLADGNFKVCLFGPSEVSLRDPLRSGADDEALREII

GAAVKRKKAAHAGMLDIAKTANRPMIHIGG

SEQ ID NO: 26 (CNX3):
>sp|Q39056|CNX3_ARATH Cyclic pyranopterin monophosphate synthase, mitochondrial OS = *Arabidopsis thaliana* OX = 3702 GN = CNX3 PE = 1 SV = 1
MISTLRRAVFLRRFPAVVSPIKRAFSSRIDDEFDPQIMNINELNQEMQSIFGQEPSPDGP

GTMDFSELKSSKIEPLRSKNIDFRQQIEYHKSTHSSKNDSQAIEQYAKVASDMSKLTHVG

IAGEAQMVDVSSKDNSKRTALACCKVILGKRVFDLVLANQMGKGDVLGVAKIAGINGAKQ

TSSLIPLCHNIALTHVRVDLRLNPEDFSVDIEGEASCTGKTGVEMEAMTAVSVAGLTVYD

MCKAASKDISITDVRLERKTGGKSGSWSRL

SEQ ID NO: 27 (MOCS3):
>sp|Q9ZNW0|MOCS3_ARATH Adenylyltransferase and sulfurtransferase MOCS3 OS = *Arabidopsis thaliana* OX = 3702 GN = MOCS3 PE = 2 SV = 1
MMSNGGDSSEIVRELEELKLKKAEIEHRISTLEAKLQDTAAVELYDAVSNGDSYLTAPEL

EHGLSPDQIYRYSROLLLPSFAVEGQSNLLKSSVLVIGAGGLGSPALLYLAACGVGQLGI

IDHDVVELNNMHRQIIHTEAFIGHPKVKSAAAACRSINSTIKVDEYVEALRTSNALEILS

QYDIIVDATDNPPSRYMISDCCVLLGKPLVSGAALGMEGQLTVYNHNGGPCYRCLFPTPP

PTSACQRCSDSGVLGVVPGVIGCLQALETIKLASLVGEPLSERMLLFDALSARMRIVKIR

GRSSQCTVCGDNSSFNKQTFKDFDYEDFTQFPLFAGPLNLLPAESRISSKEFKEILQKKE

QHVLLDVRPSHHYKIVSLPDSLNIPLANLETRLNELTSALKEKGNGHANTESCTNPSVFV

VCRRGNDSQRAVQYLRESGFDSAKDIIGGLEAWAANVNPNFPTY

-continued

SEQ ID NO: 28 (Moc2B):
>sp|O22827|MOC2B_ARATH Molybdopterin synthase catalytic subunit OS = *Arabidopsis thaliana* OX = 3702 GN = MOCS2 PE = 2 SV = 1
MSAEEKNLIEILEEGHKVDVVKYIDYVSAPQAGAIATFSGTTRDMFEGKTVLELRYEAYV

PMATRCLSSICTTARSTWDIHKIAVAHRLGPVPVGETSVLIAVSSVHRADGLDACKFLID

ELKASVPIWKKEVYTNGEIWKENSEFMEKRLELAEKRDSIVKKTVVEEHRRRGCCGSKVR

VEEDEEHKDITGDNKSSS

SEQ ID NO: 29 (MOC2A):
>sp|Q9S7A3|MOC2A_ARATH Molybdopterin synthase sulfur carrier subunit OS = *Arabidopsis thaliana* OX = 3702 GN = At4g10100 PE = 3 SV = 1
MDKEVTKIESDDTSSVEIKVLLFARARELTGVPDLTLKMPSGSTTQKCLDELVLKFPSLE

EVRSCVVLALNEEYTTDSAIVQHRDELAIIPPISGG

SEQ ID NO: 7 (MoaA):
>sp|P30745|MOAA_ECOLI GTP 3',8-cyclase OS = *Escherichia coli* (strain K12) OX = 83333 GN = moaA PE = 1 SV = 1
MASQLTDAFARKFYYLRLSITDVCNFRCTYCLPDGYKPSGVTNKGFLTVDEIRRVTRAFA

RLGTEKVRLTGGEPSLRRDFTDIIAAVRENDAIRQIAVTTNGYRLERDVASWRDAGLTGI

NVSVDSLDARQFHAITGQDKFNQVMAGIDAAFEAGFEKVKVNTVLMRDVNHHQLDTFLNW

IQHRPIQLRFIELMETGEGSELFRKHHISGQVLRDELLRRGWIHQLRQRSDGPAQVFCHP

DYAGEIGLIMPYEKDFCATCNRLRVSSIGKLHLCLFGEGGVNLRDLLEDDTQQQALEARI

SAALREKKQTHFLHQNNTGITQNLSYIGG

SEQ ID NO: 8 (MoaC):
>sp|P0A738|MOAC_ECOLI Cyclic pyranopterin monophosphate synthase OS = *Escherichia coli* (strain K12) OX = 83333 GN = moaC PE = 1 SV = 2
MSQLTHINAAGEAHMVDVSAKAETVREARAEAFVTMRSETLAMIIDGRHHKGDVFATARI

AGIQAAKRTWDLIPLCHPLMLSKVEVNLQAEPEHNRVRIETLCRLTGKTGVEMEALTAAS

VAALTIYDMCKAVQKDMVIGPVRLLAKSGGKSGDFKVEADD

SEQ ID NO: 9 (MoaD):
>sp|P30748|MOAD_ECOLI Molybdopterin synthase sulfur carrier subunit OS = *Escherichia coli* (strain K12) OX = 83333 GN = moaD PE = 1 SV = 2
MIKVLFFAQVRELVGTDATEVAADFPTVEALRQHMAAQSDRWALALEDGKLLAAVNQTLV

SFDHPLTDGDEVAFFPPVTGG

SEQ ID NO: 10 (MoaE):
>sp|P30749|MOAE_ECOLI Molybdopterin synthase catalytic subunit OS = *Escherichia coli* (strain K12) OX = 83333 GN = moaE PE = 1 SV = 3
MAETKIVVGPQPFSVGEEYPWLAERDEDGAVVTFTGKVRNHNLGDSVNALTLEHYPGMTE

KALAEIVDEARNRWPLGRVTVIHRIGELWPGDEIVFVGVTSAHRSSAFEAGQFIMDYLKT

RAPFWKREATPEGDRWVEARESDQQAAKRW

SEQ ID NO: 18 (MoeA):
>sp|P12281|MOEA_ECOLI Molybdopterin molybdenumtransferase OS = *Escherichia coli* (strain K12) OX = 83333 GN = moeA PE = 1 SV = 1
MEFTTGLMSLDTALNEMLSRVTPLTAQETLPLVQCFGRILASDVVSPLDVPGFDNSAMDG

YAVRLADIASGQPLPVAGKSFAGQPYHGEWPAGTCIRIMTGAPVPEGCEAVVMQEQTEQM

DNGVRFTAEVRSGQNIRRRGEDISAGAVVFPAGTRLTTAELPVIASLGIAEVPVIRKVRV

ALFSTGDELQLPGQPLGDGQIYDTNRLAVHLMLEQLGCEVINLGIIRDDPHALRAAFIEA

DSQADVVISSGGVSVGEADYTKTILEELGEIAFWKLAIKPGKPFAFGKLSNSWFCGLPGN

PVSATLTFYQLVQPLLAKLSGNTASGLPARQRVRTASRLKKTPGRLDFQRGVLQRNADGE

LEVTTTGHQGSHIFSSFSLGNCFIVLERDRGNVEVGEWVEVEPFNALFGGL

-continued

SEQ ID NO: 19 (MoeB):
>sp|P12282|MOEB_ECOLI Molybdopterin-synthase adenylyltransferase OS = *Escherichia coli* (strain K12) OX = 83333 GN = moeB PE = 1 SV = 1
MAELSDQEMLRYNRQIILRGFDFDGQEALKDSRVLIVGLGGLGCAASQYLASAGVGNLTL

LDFDTVSLSNLQRQTLHSDATVGQPKVESARDALTRINPHIAITPVNALLDDAELAALIA

EHDLVLDCTDNVAVRNQLNAGCFAAKVPLVSGAAIRMEGQITVFTYQDGEPCYRCLSRLF

GENALTCVEAGVMAPLIGVIGSLQAMEAIKMLAGYGKPASGKIVMYDAMTCQFREMKLMR

NPGCEVCGQ

SEQ ID NO: 20 (mogA):
>sp|P0AF03|MOG_ECOLI Molybdopterin adenylyltransferase OS = *Escherichia coli* (strain K12) OX = 83333 GN = mog PE = 1 SV = 1
MNTLRIGLVSISDRASSGVYQDKGIPALEEWLTSALTTPFELETRLIPDEQAIIEQTLCE

LVDEMSCHLVLTTGGTGPARRDVTPDATLAVADREMPGFGEQMRQISLHFVPTAILSRQV

GVIRKQALILNLPGQPKSIKETLEGVKDAEGNVVVHGIFASVPYCIQLLEGPYVETAPEV

VAAFRPKSARRDVSE

SEQ ID NO: 11 (MobA):
>sp|P32173|MOBA_ECOLI Molybdenum cofactor guanylyltransferase OS = *Escherichia coli* (strain K12) OX = 83333 GN = mobA PE = 1 SV = 1
MNLMTTITGVVLAGGKARRMGGVDKGLLELNGKPLWQHVADALMTQLSHVVVNANRHQEI

YQASGLKVIEDSLADYPGPLAGMLSVMQQEAGEWFLFCPCDTPYIPPDLAARLNHQRKDA

PVVWVHDGERDHPTIALVNRAIEPLLLEYLQAGERRVMVFMRLAGGHAVDFSDHKDAFVN

VNTPEELARWQEKR

SEQ ID NO: 13 (mocA):
>sp|Q46810|MOCA_ECOLI Molybdenum cofactor cytidylyltransferase OS = *Escherichia coli* (strain K12) OX = 83333 GN = mocA PE = 1 SV = 1
MSAIDCIITAAGLSSRMGQWKMMLPWEQGTILDTSIKNALQFCSRIILVTGYRGNELHER

YANQSNITIIHNPDYAQGLLTSVKAAVPAVQTEHCFLTHGDMPTLTIDIFRKIWSLRNDG

AILPLHNGIPGHPILVSKPCLMQAIQRPNVTNMRQALLMGDHYSVEIENAEIILDIDTPD DFITAKERYTEI

SEQ ID NO: 14 (modA):
>sp|P37329|MODA_ECOLI Molybdate-binding protein ModA OS = *Escherichia coli* (strain K12) OX = 83333 GN = modA PE = 1 SV = 1
MARKWLNLFAGAALSFAVAGNALADEGKITVFAAASLTNAMQDIATQFKKEKGVDVVSSF

ASSSTLARQIEAGAPADLFISADQKWMDYAVDKKAIDTATRQTLLGNSLVVVAPKASVQK

DFTIDSKTNWTSLLNGGRLAVGDPEHVPAGIYAKEALQKLGAWDTLSPKLAPAEDVRGAL

ALVERNEAPLGIVYGSDAVASKGVKVVATFPEDSHKKVEYPVAVVEGHNNATVKAFYDYL

KGPQAAEIFKRYGFTIK

SEQ ID NO: 15 (modB):
>sp|P39423|MODB_BPT4 NAD--protein ADP-ribosyltransferase modB OS = *Enterobacteria phage* T4 OX = 10665 GN = modB PE = 1 SV = 2
MIINLADVEQLSIKAESVDFQYDMYKKVCEKFTDFEQSVLWQCMEAKKNEALHKHLNEII

KKHLTKSPYQLYRGISKSTKELIKDLQVGEVFSTNRVDSFTTSLHTACSFSYAEYFTETI

LRLKTDKAFNYSDHISDIILSSPNTEFKYTYEDTDGLDSERTDNLMMIVREQEWMIPIGK

SEQ ID NO: 16 (modC):
>sp|P09833|MODC_ECOLI Molybdenum import ATP-binding protein ModC OS = *Escherichia coli* (strain K12) OX = 83333 GN = modC PE = 3 SV = 4
MLELNFSQTLGNHCLTINETLPANGITAIFGVSGAGKTSLINAISGLTRPQKGRIVLNGR

VLNDAEKGICLTPEKRRVGYVFQDARLFPHYKVRGNLRYGMSKSMVDQFDKLVALLGIEP

LLDRLPGSLSGGEKQRVAIGRALLTAPELLLLDEPLASLDIPRKRELLPYLQRLTREINI

PMLYVSHSLDEILHLADRVMVLENGQVKAFGALEEVWGSSVMNPWLPKEQQSSILKVTVL

EHHPHYAMTALALGDQHLWVNKLDEPLQAALRIRIQASDVSLVLQPPQQTSIRNVLRAKV

VNSYDDNGQVEVELEVGGKTLWARISPWARDELAIKPGLWLYAQIKSVSITA

-continued

SEQ ID NO: 21 (IscS):
>sp|P0A6B7|ISCS_ECOLI Cysteine desulfurase IscS OS = *Escherichia coli* (strain K12) OX = 83333 GN = iscS PE = 1 SV = 1

MKLPIYLDYSATTPVDPRVAEKMMQFMTMDGTFGNPASRSHRFGWQAEEAVDIARNQIAD

LVGADPREIVFTSGATESDNLAIKGAANFYQKKGKHIITSKTEHKAVLDTCRQLEREGFE

VTYLAPQRNGIIDLKELEAAMRDDTILVSIMHVNNEIGVVQDIAAIGEMCRARGIIYHVD

ATQSVGKLPIDLSQLKVDLMSFSGHKIYGPKGIGALYVRRKPRVRIEAQMHGGGHERGMR

SGTLPVHQIVGMGEAYRIAKEEMATEMERLRGLRNRLWNGIKDIEEVYLNGDLEHGAPNI

LNVSFNYVEGESLIMALKDLAVSSGSACTSASLEPSYVLRALGLNDELAHSSIRFSLGRF

TTEEEIDYTIELVRKSIGRLRDLSPLWEMYKQGVDLNSIEWAHH

The strain construction approach is described in WO2013144257A1 (publication of patent application PCT/EP2013/056623) and WO 2015/028582. Expression cassettes from various genes of interest are recombined in vivo into a pathway at a specific locus upon transformation of this yeast (U.S. Pat. No. 9,738,890 B2).

The open reading frames (ORFs), are synthesized at TWIST (South San Francisco, CA 94080, 35 USA). The promoter, ORF and terminator sequences are assembled into expression cassettes with Golden Gate technology, as described by Engler et al (2011) and ligated into BsaI-digested backbone vectors that decorated the expression cassettes with the connectors for the in vivo recombination step. The expression cassettes including connectors are amplified by PCR. In addition, a 5'- and a 3'-DNA fragment of approximately 500 by of the up- and downstream part of the integration locus is amplified using PCR and decorated by a connector sequence. Upon transformation of yeast cells with these DNA fragments, in vivo recombination and integration into the genome takes place at the desired location. CRISPR-Cas9 technology is used to make a unique double stranded break at the integration locus to target the pathway to this specific locus (DiCarlo et al., 2013, Nucleic Acids Res 41:4336-4343) and WO16110512.

The strains are tested in anaerobic fermentation. Corn mash (30% (w/w) solids) is prepared by mixing 333 g corn flour (Limagrain, Belgium) per kg mash, with 300 ml/kg thin stillage and 367 ml/kg demineralized water. The pH is adjusted to 5.5 with 2M KOH solution. Starch in the mixture is liquefied by adding 0.02 g/kg of a commercial alpha-amylase (Termamyl, Novozymes), and incubated for 4 hours at 80'C in a rotary shaker. After liquefaction the pH is adjusted to 4.5 with 2M H2SO4 solution. The strains are pre-cultured by inoculating 200 ml YepH (20 g/l phytone peptone, 10 g/l yeast extract) supplemented with 2% w/v glucose, from a cryovial and incubated in a 500 ml shake flask. To determine the inoculation volume of the yeast, the dry cell weight (DCW) content of the culture is determined by filtration and drying via a CEM-SMART microwave. A quantity of the preculture corresponding to the required inoculation size for the propagations are centrifuged (3 min, 4500×g), washed once with sterile demineralized water, centrifuged once more, resuspended in propagation medium and transferred to the propagation flasks. Propagations are performed in 100 ml Erlenmeyer shake flasks with a foam stopper for 6 h at 32'C, 150 rpm, creating a semi-aerobic environment. The propagation medium is diluted to a 70% (v/v) solution, checked for pH 4.5 and is supplied with 4.2 g/l KNO3 and antibiotics (neomycin and PenG). For each strain 0.088 g/l commercial amyloglucosidase enzyme (Spirizyme Excel, novozymes) is added. Fermentations were performed in simultaneous saccharification fermentation (SSF) mode, using 500 ml schott bottles filled with 200 ml of corn mash and fitted with an Ankom gas production system cap (Ankom, Macedon, NY, USA), effectively rendering the fermentations anaerobic. The corn mash is used as such, with addition of 3.4 g/l KNO3 and antibiotics, pH 4.5. The inoculation of the fermenters is done by transferring 10% of the propagation medium to the fermenters, reaching 400 ml of volume. The pH is not controlled during the fermentations, while temperature is controlled at 32° C. Fermentation samples were taken throughout the run and different components were measured by HPLC analysis using a Dionex Ultimate 3000 HPLC system with column oven TCC-3400 and Autosampler WPS-3000 equipped with a guard column (Bio-Rad H cartridge) and an Aminex HPX-87H column (300×7.8 mm; Bio-Rad, Hercules, USA); elution took place at 65'C with 5 mM H2804 at 0.55 ml/min; the eluate is monitored using a Refractive Index detector RefractoMax 521. $CO_2$ is measured online during the fermentation.

The invention claimed is:

1. A *Saccharomyces* yeast cell, comprising one or more nucleic acid sequences encoding an enzyme having NADH-dependent nitrate reductase activity and one or more nucleic acid sequences encoding an enzyme having NADH-dependent nitrite reductase activity;

wherein the one or more nucleic acid sequences encoding an enzyme having NADH-dependent nitrate reductase activity encode the amino acid sequence set forth by SEQ ID NO: 1 or an amino acid sequence having at least 80% sequence identity to SEQ ID NO: 1; and wherein the one or more nucleic acid sequences encoding an enzyme having NADH-dependent nitrite reductase activity encode the amino acid sequence set forth by SEQ ID NO: 3 or an amino acid sequence having at least 80% sequence identity to SEQ ID NO: 3 and the amino acid sequence set forth by SEQ ID NO: 4 or an amino acid sequence having at least 80% sequence identity to SEQ ID NO: 4.

2. The *Saccharomyces* yeast cell according to claim 1, wherein the *Saccharomyces* yeast cell further comprises one or more nucleic acid sequences encoding a nitrate/nitrite transporter.

3. The *Saccharomyces* yeast cell according to claim 1, further comprising flavin adenine dinucleotide (FAD), one or more heme prosthetic groups, a molybdenum cofactor (MoCo), or any combination thereof.

4. The *Saccharomyces* yeast cell according to claim 1, further comprising one or more nucleic acid sequences encoding enzymes for the synthesis of one or more of a flavin adenine dinucleotide (FAD), one or more heme prosthetic groups, or a molybdenum cofactor (MoCo).

5. The *Saccharomyces* yeast cell according to claim 1, further comprising one or more of:

a nucleic acid sequence encoding a GTP 3',8-cyclase;

a nucleic acid sequence encoding a Cyclic pyranopterin monophosphate synthase;

a nucleic acid sequence encoding a Molybdopterin synthase catalytic subunit;

a nucleic acid sequence encoding a Molybdopterin synthase sulfur carrier subunit;

a nucleic acid sequence encoding a Molybdopterin adenylyltransferase;

a nucleic acid sequence encoding a Molybdopterin-synthase adenylyltransferase; or a nucleic acid sequence encoding a Molybdopterin molybdenumtransferase.

6. The *Saccharomyces* yeast cell according to claim 1, further comprising one or more of:

a polypeptide selected from the group consisting of SEQ ID NO:6 and a functional homologue having at least 80% amino acid sequence identity to SEQ ID NO:6; or a polypeptide selected from the group consisting of SEQ ID NO: 22 and a functional homologue having at least 80% amino acid sequence identity to SEQ ID NO: 22.

7. The *Saccharomyces* yeast cell according to claim 1, wherein the *Saccharomyces* yeast cells are either free of glycerol phosphate phosphatase activity or have reduced glycerol phosphate phosphatase activity compared to corresponding wild-type cells.

8. The *Saccharomyces* yeast cell according to claim 1, wherein the *Saccharomyces* yeast cells are either free of glycerol 3-phosphate dehydrogenase activity or have reduced glycerol 3-phosphate dehydrogenase activity compared to corresponding wild-type cells.

9. The *Saccharomyces* yeast cell according to claim 1, wherein the *Saccharomyces* yeast cell further comprises one or more of:

one or more nucleic acid sequences encoding a glycerol dehydrogenase;

one or more nucleic acid sequences encoding a dihydroxyacetone kinase; or one or more nucleic acid sequences encoding a glycerol transporter.

10. An anaerobic fermentation process for production of a fermentation product, comprising fermenting a feed, which feed comprises an oxidized nitrogen source and a fermentable carbon source, using a *Saccharomyces* yeast cell as claimed in claim 1.

11. The anaerobic fermentation process according to claim 10 wherein the *Saccharomyces* yeast cell produces less glycerol compared to corresponding wild-type cells.

12. The anaerobic fermentation process according to claim 10, wherein the *Saccharomyces* yeast cell produces less ethyl carbamate compared to corresponding wild-type cells.

13. The anaerobic fermentation process according to claim 10, wherein the fermentable carbon source comprises or consists of one or more monosaccharides, disaccharides or polysaccharides.

14. The anaerobic fermentation process according to claim 10, wherein the oxidized nitrogen source comprises or consists of one or more of:

an acid, salt or ion of nitrate; or an acid, salt or ion of nitrite.

15. The anaerobic fermentation process according to claim 10, wherein the oxidized nitrogen source comprises one or more of nitrate or nitrite in combination with one or more other nitrogen sources selected from the group consisting of ammonium, ammonia and urea.

16. The anaerobic fermentation process according to claim 10, wherein the fermentation product is selected from the group consisting of ethanol, n-butanol, isobutanol, lactic acid, 3-hydroxy-propionic acid, acrylic acid, acetic acid, succinic acid, fumaric acid, malic acid, itaconic acid, maleic acid, citric acid, and adipic acid.

17. The anaerobic fermentation process according to claim 10, wherein further a fermentation co-product is produced.

18. The anaerobic fermentation process according to claim 17, wherein the fermentation co-product comprises equal to or less than 17 ng/g of ethyl carbamate.

19. The *Saccharomyces* yeast cell according to claim 1, wherein the *Saccharomyces* yeast cell is a *Saccharomyces cerevisiae* yeast cell.

20. The *Saccharomyces* yeast cell according to claim 19, wherein the *Saccharomyces cerevisiae* yeast cell comprises a genomic mutation in at least one gene selected from the group consisting of glycerol 3-phosphate dehydrogenase 1 (GPD1), glycerol 3-phosphate dehydrogenase 2 (GPD2), glycerol phosphate phosphatase 1 (GPP1) and glycerol phosphate phosphatase 2 (GPP2).

* * * * *

SEQUENCE LISTING

<160> NUMBER OF SEQ ID NOS: 29

<210> SEQ ID NO 1
<211> LENGTH: 910
<212> TYPE: PRT
<213> ORGANISM: Zea mays
<220> FEATURE:
<221> NAME/KEY: MISC_FEATURE
<222> LOCATION: (1)..(910)
<223> OTHER INFORMATION: NR1 nitrate reductase

<400> SEQUENCE: 1

-continued

```
Met Ala Ala Val Glu Pro Arg Gln Phe Gly Arg Leu Glu Pro Gly Ser
1               5                   10                  15

Ser Pro Val Arg Val Ala Thr Asn Gly Ala Lys Ala Tyr Pro Pro Pro
            20                  25                  30

Ala Ser His Leu Pro Arg Arg Ala Asp Ser Pro Val Arg Gly Cys Ser
        35                  40                  45

Phe Pro Pro Leu Val Ser Pro Pro Arg Arg Leu Asp Asp Ala Ser Asp
    50                  55                  60

Asp Glu Asp Glu Glu Gln Glu Asp Trp Arg Glu Leu Tyr Gly Ser His
65                  70                  75                  80

Leu Gln Leu Glu Val Glu Pro Ala Val Gln Asp Ala Arg Asp Glu Gly
                85                  90                  95

Thr Ala Asp Ala Trp Ile Glu Arg Asn Pro Cys Leu Val Arg Leu Thr
            100                 105                 110

Gly Lys His Pro Leu Asn Cys Glu Pro Pro Leu Ala Arg Leu Met His
        115                 120                 125

His Gly Phe Ile Thr Pro Ala Pro Leu His Tyr Val Arg Asn His Gly
    130                 135                 140

Ala Val Pro Arg Gly Asp Trp Ala Thr Trp Thr Val Glu Val Thr Gly
145                 150                 155                 160

Leu Val Arg Arg Pro Ala Arg Leu Thr Met Glu Glu Leu Ala Arg Asp
                165                 170                 175

Phe Pro Ala Val Glu Ile Pro Val Thr Leu Ala Cys Ala Gly Asn Arg
            180                 185                 190

Arg Lys Glu Gln Asn Met Val Gln Gln Thr Val Gly Phe Asn Trp Gly
        195                 200                 205

Ala Ala Gly Val Ser Thr Ser Val Trp Arg Gly Ala Arg Leu Arg Asp
    210                 215                 220

Val Leu Arg Arg Cys Gly Ile Val Pro Arg Lys Gly Gly Ala Leu Asn
225                 230                 235                 240

Val Cys Phe Glu Gly Ala Glu Asp Leu Pro Gly Gly Gly Gly Ser Lys
                245                 250                 255

Tyr Gly Thr Ser Val Thr Arg Glu Trp Ala Leu Asp Pro Ser Arg Asp
            260                 265                 270

Ile Met Leu Ala Tyr Met Gln Asn Gly Glu Pro Leu Leu Pro Asp His
        275                 280                 285

Gly Phe Pro Val Arg Val Ile Ile Pro Gly Cys Ile Gly Gly Arg Met
    290                 295                 300

Val Lys Trp Leu Lys Arg Ile Ile Val Thr Pro Ala Glu Ser Asp Asn
305                 310                 315                 320

Tyr Tyr His Phe Lys Asp Asn Arg Val Leu Pro Ser His Val Asp Ala
                325                 330                 335

Glu Leu Ala Asn Ala Glu Ala Trp Trp Tyr Lys Pro Glu Tyr Ile Ile
            340                 345                 350

Asn Glu Leu Asn Ile Asn Ser Val Ile Thr Thr Pro Gly His Asp Glu
        355                 360                 365

Ile Leu Pro Ile Asn Ser Ile Thr Thr Gln Arg Gly Tyr Thr Met Lys
    370                 375                 380

Gly Tyr Ala Tyr Ser Gly Gly Gly Lys Lys Val Thr Arg Val Glu Val
385                 390                 395                 400

Thr Leu Asp Gly Gly Glu Thr Trp Leu Val Cys His Leu Asp His Pro
                405                 410                 415

Glu Lys Pro Asn Lys Tyr Gly Lys Tyr Trp Cys Trp Cys Phe Trp Ser
```

-continued

```
            420                 425                 430

Val Glu Val Glu Val Leu Asp Leu Leu Gly Ala Lys Glu Ile Ala Val
        435                 440                 445

Arg Ala Trp Asp Gln Ser Leu Asn Thr Gln Pro Glu Lys Leu Ile Trp
    450                 455                 460

Asn Leu Met Gly Met Met Asn Asn Cys Trp Phe Lys Val Lys Val Asn
465                 470                 475                 480

Val Cys Arg Pro His Lys Gly Glu Ile Gly Leu Val Phe Glu His Pro
                485                 490                 495

Thr Gln Pro Gly Asn Gln Pro Gly Gly Trp Met Ala Arg Gln Lys His
            500                 505                 510

Leu Glu Thr Ala Glu Ala Ala Ala Pro Gly Leu Lys Arg Ser Thr Ser
        515                 520                 525

Thr Pro Phe Met Asn Thr Thr Asp Val Gly Lys Gln Phe Thr Met Ser
    530                 535                 540

Glu Val Arg Lys His Ala Ser Gln Glu Ser Ala Trp Ile Ala Val His
545                 550                 555                 560

Gly His Val Tyr Asp Cys Thr Lys Phe Leu Lys Asp His Pro Gly Gly
                565                 570                 575

Ala Asp Ser Ile Leu Ile Asn Ala Gly Thr Asp Cys Thr Glu Glu Phe
            580                 585                 590

Asp Ala Ile His Ser Asp Lys Ala Lys Ala Leu Leu Asp Thr Tyr Arg
        595                 600                 605

Ile Gly Glu Leu Ile Thr Thr Gly Thr Gly Tyr Ser Ser Asp Asn Ser
    610                 615                 620

Val His Gly Gly Ser Val Leu Ser His Leu Ala Pro Ile Arg Glu Ala
625                 630                 635                 640

Val Arg Ala Pro Ala Leu Ser Asn Pro Arg Asp Lys Ile His Cys Arg
                645                 650                 655

Leu Val Gly Lys Lys Glu Leu Ser Arg Asp Val Arg Leu Phe Arg Phe
            660                 665                 670

Ser Leu Pro Ser Pro Asp Gln Val Leu Gly Leu Pro Ile Gly Lys His
        675                 680                 685

Ile Phe Val Cys Ala Ser Ile Glu Gly Lys Leu Cys Met Arg Ala Tyr
    690                 695                 700

Thr Pro Thr Ser Met Val Asp Glu Ile Gly His Phe Asp Leu Leu Val
705                 710                 715                 720

Lys Val Tyr Phe Lys Asn Glu His Pro Lys Phe Pro Asn Gly Gly Leu
                725                 730                 735

Met Thr Gln Tyr Leu Asp Ser Leu Pro Val Gly Ser Tyr Ile Asp Val
            740                 745                 750

Lys Gly Pro Leu Gly His Val Glu Tyr Thr Gly Arg Gly Ser Phe Val
        755                 760                 765

Ile Asn Gly Lys Gln Arg His Ala Ser Arg Leu Ala Met Ile Cys Gly
    770                 775                 780

Gly Ser Gly Ile Thr Pro Met Tyr Gln Ile Ile Gln Ala Val Leu Arg
785                 790                 795                 800

Asp Gln Pro Glu Asp His Thr Glu Met His Leu Val Tyr Ala Asn Arg
                805                 810                 815

Thr Glu Asp Asp Ile Leu Leu Arg Asp Glu Leu Asp Arg Trp Ala Ala
            820                 825                 830

Glu Tyr Pro Asp Arg Leu Lys Val Trp Tyr Val Ile Asp Gln Val Lys
        835                 840                 845
```

-continued

```
Arg Pro Glu Glu Gly Trp Lys Tyr Ser Val Gly Phe Val Thr Glu Ala
    850                 855                 860

Val Leu Arg Glu His Val Pro Glu Gly Gly Asp Asp Thr Leu Ala Leu
865                 870                 875                 880

Ala Cys Gly Pro Pro Pro Met Ile Gln Phe Ala Ile Ser Pro Asn Leu
                885                 890                 895

Glu Lys Met Lys Tyr Asp Met Ala Asn Ser Phe Val Val Phe
            900                 905                 910


<210> SEQ ID NO 2
<211> LENGTH: 926
<212> TYPE: PRT
<213> ORGANISM: Spinacia oleracea
<220> FEATURE:
<221> NAME/KEY: MISC_FEATURE
<222> LOCATION: (1)..(926)
<223> OTHER INFORMATION: NIA Nitrate reductase

<400> SEQUENCE: 2

Met Ala Ala Ser Val Asp Arg Gln Tyr His Pro Ala Pro Met Ser Gly
1               5                   10                  15

Val Val Arg Thr Pro Phe Ser Asn His His Arg Ser Asp Ser Pro Val
            20                  25                  30

Arg Asn Gly Tyr Thr Phe Ser Asn Pro Pro Ser Ser Asn Gly Val Val
        35                  40                  45

Lys Pro Gly Glu Lys Ile Lys Leu Val Asp Asn Asn Ser Asn Ser Asn
    50                  55                  60

Asn Gly Ser Asn Asn Asn Asn Asn Arg Tyr Asp Ser Asp Ser Glu Glu
65                  70                  75                  80

Asp Asp Asp Glu Asn Glu Met Asn Val Trp Asn Glu Met Ile Lys Lys
                85                  90                  95

Gly Asn Ser Glu Leu Glu Pro Ser Ser Val Asp Ser Arg Asp Glu Gly
            100                 105                 110

Thr Ala Asp Gln Trp Ile Glu Arg Asn Pro Ser Met Ile Arg Leu Thr
        115                 120                 125

Gly Lys His Pro Phe Asn Ser Glu Pro Pro Leu Thr Arg Leu Met His
    130                 135                 140

His Gly Phe Leu Thr Pro Val Pro Leu His Tyr Val Arg Asn His Gly
145                 150                 155                 160

Pro Val Pro Asn Ala Lys Trp Glu Asp Trp Thr Val Glu Val Thr Gly
                165                 170                 175

Leu Val Lys Arg Pro Ile Arg Phe Thr Met Asp Gln Leu Val Asn Asp
            180                 185                 190

Phe Gln Ser Arg Glu Phe Pro Val Thr Leu Val Cys Ala Gly Asn Arg
        195                 200                 205

Arg Lys Glu Gln Asn Met Thr Lys Gln Ser Ile Gly Phe Asn Trp Gly
    210                 215                 220

Ser Ala Ala Val Ser Thr Ser Val Trp Arg Gly Val Pro Leu Arg Asp
225                 230                 235                 240

Val Leu Lys Arg Cys Gly Val Met Ser Ser Leu Lys Gly Ala Leu Asn
                245                 250                 255

Val Cys Phe Glu Gly Ala Glu Asp Leu Pro Gly Gly Gly Gly Ser Lys
            260                 265                 270

Tyr Gly Thr Ser Val Lys Arg Glu Phe Ala Met Asp Pro Ala Arg Asp
        275                 280                 285
```

-continued

```
Ile Ile Leu Ala Tyr Met Gln Asn Gly Glu Lys Leu Ser Pro Asp His
    290                 295                 300

Gly Tyr Pro Val Arg Met Ile Ile Pro Gly Phe Ile Gly Gly Arg Met
305                 310                 315                 320

Val Lys Trp Leu Lys Arg Ile Ile Val Thr Thr Thr Glu Ser Asp Asn
                325                 330                 335

Tyr Tyr His Tyr Lys Asp Asn Arg Val Leu Pro Ser His Val Asp Ala
            340                 345                 350

Glu Leu Ala Asn Ser Glu Ala Trp Trp Tyr Lys Gln Glu Tyr Ile Ile
        355                 360                 365

Asn Glu Leu Asn Val Asn Ser Val Ile Thr Ser Pro Cys His Glu Glu
    370                 375                 380

Ile Leu Pro Ile Asn Ala Trp Thr Thr Gln Arg Pro Tyr Thr Met Arg
385                 390                 395                 400

Gly Tyr Ala Tyr Ser Gly Gly Gly Arg Lys Val Thr Arg Val Glu Val
                405                 410                 415

Thr Met Asp Gly Gly Asp Thr Trp Asp Ile Cys Glu Leu Asp His Gln
            420                 425                 430

Glu Arg Gly Ser Lys Tyr Gly Lys Phe Trp Cys Trp Cys Phe Trp Ser
        435                 440                 445

Leu Glu Val Glu Val Leu Asp Leu Leu Gly Ala Lys Glu Ile Gly Val
    450                 455                 460

Arg Ala Trp Asp Glu Ser Leu Asn Thr Gln Pro Glu Lys Leu Ile Trp
465                 470                 475                 480

Asn Val Met Gly Met Met Asn Asn Cys Trp Phe Arg Val Lys Thr Asn
                485                 490                 495

Val Cys Lys Pro His Lys Gly Glu Ile Gly Ile Val Phe Glu His Pro
            500                 505                 510

Thr Gln Pro Gly Asn Lys Ser Gly Gly Trp Met Ala Arg Glu Arg His
        515                 520                 525

Leu Glu Ile Ser Asp Ser Gly Pro Thr Leu Lys Arg Thr Ala Ser Thr
    530                 535                 540

Pro Phe Met Asn Thr Thr Ser Lys Met Tyr Ser Met Ser Glu Val Lys
545                 550                 555                 560

Lys His Asn Thr Ala Asp Ser Ala Trp Ile Val Val His Gly Asn Val
                565                 570                 575

Tyr Asn Ala Thr Arg Phe Leu Lys Asp His Pro Gly Gly Ser Asp Ser
            580                 585                 590

Ile Leu Ile Asn Ala Gly Thr Asp Cys Thr Glu Glu Phe Asp Ala Ile
        595                 600                 605

His Ser Asp Lys Ala Lys Arg Leu Leu Glu Asp Phe Arg Ile Gly Glu
    610                 615                 620

Leu Ile Ser Thr Gly Tyr Thr Ser Asp Ser Ser Ser Pro Gly Asn Ser
625                 630                 635                 640

Val His Gly Gly Ser Val Tyr Ser Gly Leu Ala Gly Leu Ala Pro Ile
                645                 650                 655

Thr Glu Ala Val Pro Leu Arg Asn Val Ala Leu Asn Pro Arg Val Lys
            660                 665                 670

Ile Pro Cys Lys Leu Ile Glu Lys Val Ser Leu Ser His Asp Val Arg
        675                 680                 685

Arg Phe Arg Phe Gly Leu Pro Ser Glu Asp Gln Val Leu Gly Leu Pro
    690                 695                 700

Val Gly Lys His Ile Phe Leu Cys Ala Asn Val Asp Asp Lys Leu Cys
```

```
705                 710                 715                 720

Met Arg Ala Tyr Thr Pro Ser Ser Thr Ile Asp Val Val Gly Tyr Phe
                725                 730                 735

Asp Leu Val Val Lys Val Tyr Phe Lys Asp Val His Pro Arg Phe Pro
            740                 745                 750

Asn Gly Gly Val Met Ser Gln His Leu Asp Ser Leu Ser Leu Gly Ser
        755                 760                 765

Ile Val Asp Val Lys Gly Pro Leu Gly His Ile Glu Tyr Leu Gly Lys
    770                 775                 780

Gly Asn Phe Thr Val His Gly Lys Pro Lys Phe Ala Lys Lys Leu Ala
785                 790                 795                 800

Met Ile Ser Gly Gly Thr Gly Ile Thr Pro Ile Tyr Gln Val Met Gln
                805                 810                 815

Ala Ile Leu Lys Asp Pro Glu Asp Lys Thr Glu Met His Val Val Tyr
            820                 825                 830

Ala Asn Arg Thr Glu Glu Asp Ile Leu Leu Arg Glu Glu Leu Asp Lys
        835                 840                 845

Trp Ala Asp Glu Phe Arg Asp Arg Val Lys Val Trp Tyr Val Val Glu
    850                 855                 860

Lys Ala Glu Glu Gly Trp Lys Tyr Asp Thr Gly Phe Ile Ser Glu Lys
865                 870                 875                 880

Ile Leu Arg Asp His Val Pro Ala Val Gly Asp Asp Val Leu Ala Leu
                885                 890                 895

Thr Cys Gly Pro Pro Pro Met Ile Gln Phe Ala Val Gln Pro Asn Leu
            900                 905                 910

Asp Lys Met Gly Phe Asp Ile Lys Glu Gln Leu Leu Ile Phe
        915                 920                 925


<210> SEQ ID NO 3
<211> LENGTH: 108
<212> TYPE: PRT
<213> ORGANISM: Escherichia coli
<220> FEATURE:
<221> NAME/KEY: MISC_FEATURE
<222> LOCATION: (1)..(108)
<223> OTHER INFORMATION: nirD Nitrite reductase Escherichia coli (small
      subunit)

<400> SEQUENCE: 3

Met Ser Gln Trp Lys Asp Ile Cys Lys Ile Asp Asp Ile Leu Pro Glu
1               5                   10                  15

Thr Gly Val Cys Ala Leu Leu Gly Asp Glu Gln Val Ala Ile Phe Arg
            20                  25                  30

Pro Tyr His Ser Asp Gln Val Phe Ala Ile Ser Asn Ile Asp Pro Phe
        35                  40                  45

Phe Glu Ser Ser Val Leu Ser Arg Gly Leu Ile Ala Glu His Gln Gly
    50                  55                  60

Glu Leu Trp Val Ala Ser Pro Leu Lys Lys Gln Arg Phe Arg Leu Ser
65                  70                  75                  80

Asp Gly Leu Cys Met Glu Asp Glu Gln Phe Ser Val Lys His Tyr Glu
                85                  90                  95

Ala Arg Val Lys Asp Gly Val Val Gln Leu Arg Gly
            100                 105


<210> SEQ ID NO 4
<211> LENGTH: 847
<212> TYPE: PRT
```

<213> ORGANISM: Escherichia coli
<220> FEATURE:
<221> NAME/KEY: MISC_FEATURE
<222> LOCATION: (1)..(847)
<223> OTHER INFORMATION: nirB Nitite reductase Escherichia coli (large subunit)

<400> SEQUENCE: 4

```
Met Ser Lys Val Arg Leu Ala Ile Ile Gly Asn Gly Met Val Gly His
1               5                   10                  15

Arg Phe Ile Glu Asp Leu Leu Asp Lys Ser Asp Ala Ala Asn Phe Asp
            20                  25                  30

Ile Thr Val Phe Cys Glu Glu Pro Arg Ile Ala Tyr Asp Arg Val His
        35                  40                  45

Leu Ser Ser Tyr Phe Ser His His Thr Ala Glu Glu Leu Ser Leu Val
    50                  55                  60

Arg Glu Gly Phe Tyr Glu Lys His Gly Ile Lys Val Leu Val Gly Glu
65                  70                  75                  80

Arg Ala Ile Thr Ile Asn Arg Gln Glu Lys Val Ile His Ser Ser Ala
                85                  90                  95

Gly Arg Thr Val Phe Tyr Asp Lys Leu Ile Met Ala Thr Gly Ser Tyr
            100                 105                 110

Pro Trp Ile Pro Pro Ile Lys Gly Ser Asp Thr Gln Asp Cys Phe Val
        115                 120                 125

Tyr Arg Thr Ile Glu Asp Leu Asn Ala Ile Glu Ser Cys Ala Arg Arg
    130                 135                 140

Ser Lys Arg Gly Ala Val Val Gly Gly Gly Leu Leu Gly Leu Glu Ala
145                 150                 155                 160

Ala Gly Ala Leu Lys Asn Leu Gly Ile Glu Thr His Val Ile Glu Phe
                165                 170                 175

Ala Pro Met Leu Met Ala Glu Gln Leu Asp Gln Met Gly Gly Glu Gln
            180                 185                 190

Leu Arg Arg Lys Ile Glu Ser Met Gly Val Arg Val His Thr Ser Lys
        195                 200                 205

Asn Thr Leu Glu Ile Val Gln Glu Gly Val Glu Ala Arg Lys Thr Met
    210                 215                 220

Arg Phe Ala Asp Gly Ser Glu Leu Glu Val Asp Phe Ile Val Phe Ser
225                 230                 235                 240

Thr Gly Ile Arg Pro Arg Asp Lys Leu Ala Thr Gln Cys Gly Leu Asp
                245                 250                 255

Val Ala Pro Arg Gly Gly Ile Val Ile Asn Asp Ser Cys Gln Thr Ser
            260                 265                 270

Asp Pro Asp Ile Tyr Ala Ile Gly Glu Cys Ala Ser Trp Asn Asn Arg
        275                 280                 285

Val Phe Gly Leu Val Ala Pro Gly Tyr Lys Met Ala Gln Val Ala Val
    290                 295                 300

Asp His Ile Leu Gly Ser Glu Asn Ala Phe Glu Gly Ala Asp Leu Ser
305                 310                 315                 320

Ala Lys Leu Lys Leu Leu Gly Val Asp Val Gly Gly Ile Gly Asp Ala
                325                 330                 335

His Gly Arg Thr Pro Gly Ala Arg Ser Tyr Val Tyr Leu Asp Glu Ser
            340                 345                 350

Lys Glu Ile Tyr Lys Arg Leu Ile Val Ser Glu Asp Asn Lys Thr Leu
        355                 360                 365

Leu Gly Ala Val Leu Val Gly Asp Thr Ser Asp Tyr Gly Asn Leu Leu
```

-continued

```
    370                 375                 380

Gln Leu Val Leu Asn Ala Ile Glu Leu Pro Glu Asn Pro Asp Ser Leu
385                 390                 395                 400

Ile Leu Pro Ala His Ser Gly Ser Gly Lys Pro Ser Ile Gly Val Asp
                405                 410                 415

Lys Leu Pro Asp Ser Ala Gln Ile Cys Ser Cys Phe Asp Val Thr Lys
            420                 425                 430

Gly Asp Leu Ile Ala Ala Ile Asn Lys Gly Cys His Thr Val Ala Ala
        435                 440                 445

Leu Lys Ala Glu Thr Lys Ala Gly Thr Gly Cys Gly Gly Cys Ile Pro
    450                 455                 460

Leu Val Thr Gln Val Leu Asn Ala Glu Leu Ala Lys Gln Gly Ile Glu
465                 470                 475                 480

Val Asn Asn Asn Leu Cys Glu His Phe Ala Tyr Ser Arg Gln Glu Leu
                485                 490                 495

Phe His Leu Ile Arg Val Glu Gly Ile Lys Thr Phe Glu Glu Leu Leu
            500                 505                 510

Ala Lys His Gly Lys Gly Tyr Gly Cys Glu Val Cys Lys Pro Thr Val
        515                 520                 525

Gly Ser Leu Leu Ala Ser Cys Trp Asn Glu Tyr Ile Leu Lys Pro Glu
    530                 535                 540

His Thr Pro Leu Gln Asp Ser Asn Asp Asn Phe Leu Ala Asn Ile Gln
545                 550                 555                 560

Lys Asp Gly Thr Tyr Ser Val Ile Pro Arg Ser Pro Gly Gly Glu Ile
                565                 570                 575

Thr Pro Glu Gly Leu Met Ala Val Gly Arg Ile Ala Arg Glu Phe Asn
            580                 585                 590

Leu Tyr Thr Lys Ile Thr Gly Ser Gln Arg Leu Ala Met Phe Gly Ala
        595                 600                 605

Gln Lys Asp Asp Leu Pro Glu Ile Trp Arg Gln Leu Ile Glu Ala Gly
    610                 615                 620

Phe Glu Thr Gly His Ala Tyr Ala Lys Ala Leu Arg Met Ala Lys Thr
625                 630                 635                 640

Cys Val Gly Ser Thr Trp Cys Arg Tyr Gly Val Gly Asp Ser Val Gly
                645                 650                 655

Leu Gly Val Glu Leu Glu Asn Arg Tyr Lys Gly Ile Arg Thr Pro His
            660                 665                 670

Lys Met Lys Phe Gly Val Ser Gly Cys Thr Arg Glu Cys Ser Glu Ala
        675                 680                 685

Gln Gly Lys Asp Val Gly Ile Ile Ala Thr Glu Lys Gly Trp Asn Leu
    690                 695                 700

Tyr Val Cys Gly Asn Gly Gly Met Lys Pro Arg His Ala Asp Leu Leu
705                 710                 715                 720

Ala Ala Asp Ile Asp Arg Glu Thr Leu Ile Lys Tyr Leu Asp Arg Phe
                725                 730                 735

Met Met Phe Tyr Ile Arg Thr Ala Asp Lys Leu Thr Arg Thr Ala Pro
            740                 745                 750

Trp Leu Glu Asn Leu Glu Gly Gly Ile Asp Tyr Leu Lys Ala Val Ile
        755                 760                 765

Ile Asp Asp Lys Leu Gly Leu Asn Ala His Leu Glu Glu Glu Met Ala
    770                 775                 780

Arg Leu Arg Glu Ala Val Leu Cys Glu Trp Thr Glu Thr Val Asn Thr
785                 790                 795                 800
```

-continued

```
Pro Ser Ala Gln Thr Arg Phe Lys His Phe Ile Asn Ser Asp Lys Arg
                805                 810                 815

Asp Pro Asn Val Gln Met Val Pro Glu Arg Glu Gln His Arg Pro Ala
            820                 825                 830

Thr Pro Tyr Glu Arg Ile Pro Val Thr Leu Val Glu Asp Asn Ala
        835                 840                 845


<210> SEQ ID NO 5
<211> LENGTH: 1104
<212> TYPE: PRT
<213> ORGANISM: Emericella nidulans
<220> FEATURE:
<221> NAME/KEY: MISC_FEATURE
<222> LOCATION: (1)..(1104)
<223> OTHER INFORMATION: niiA Nitrite reductase Emericella nidulans
      (Aspergillus nidulans)

<400> SEQUENCE: 5

Met Pro Leu Leu Asp Gly Pro Arg Asn Gly Glu Thr Val Thr Ala Ser
1               5                   10                  15

Ala His Asn Gly Ile Pro Ile Ile Asp Gly Val Asp Pro Ser Thr Leu
            20                  25                  30

Arg Gly Asp Ile Asp Gln Asp Pro Asn Arg Arg Gln Lys Ile Val Val
        35                  40                  45

Val Gly Leu Gly Met Val Ala Val Ala Phe Ile Glu Lys Leu Val Lys
    50                  55                  60

Leu Asp Ser Glu Arg Arg Lys Tyr Asp Ile Val Val Ile Gly Glu Glu
65                  70                  75                  80

Pro His Ile Ala Tyr Asn Arg Val Gly Leu Ser Ser Tyr Phe Glu His
                85                  90                  95

Arg Lys Ile Glu Asp Leu Tyr Leu Asn Pro Lys Glu Trp Tyr Gly Ser
            100                 105                 110

Phe Lys Asp Arg Ser Phe Asp Tyr Tyr Leu Asn Thr Arg Val Thr Asp
        115                 120                 125

Val Phe Pro Gln His Lys Thr Val Lys Thr Ser Thr Gly Asp Ile Val
    130                 135                 140

Ser Tyr Asp Ile Leu Val Leu Ala Thr Gly Ser Asp Ala Val Leu Pro
145                 150                 155                 160

Thr Ser Thr Pro Gly His Asp Ala Lys Gly Ile Phe Val Tyr Arg Thr
                165                 170                 175

Ile Ser Asp Leu Glu Arg Leu Met Glu Phe Ala Ala Asn His Lys Gly
            180                 185                 190

Gln Thr Gly Val Thr Val Gly Gly Gly Leu Leu Gly Leu Glu Ala Ala
        195                 200                 205

Lys Ala Met Thr Asp Leu Glu Asp Phe Gly Ser Val Lys Leu Ile Asp
    210                 215                 220

Arg Asn Lys Trp Val Leu Ala Arg Gln Leu Asp Gly Asp Ala Gly Ser
225                 230                 235                 240

Leu Val Thr Lys Lys Ile Arg Asp Leu Gly Leu Glu Val Leu His Glu
                245                 250                 255

Lys Arg Val Ala Lys Ile His Thr Asp Asp Asp Asn Asn Val Thr Gly
            260                 265                 270

Ile Leu Phe Glu Asp Gly Gln Glu Leu Asp Cys Cys Cys Ile Cys Phe
        275                 280                 285

Ala Ile Gly Ile Arg Pro Arg Asp Glu Leu Gly Gly Ser Thr Gly Ile
    290                 295                 300
```

-continued

```
Gln Cys Ala Lys Arg Gly Gly Phe Val Ile Asp Glu Ser Leu Arg Thr
305                 310                 315                 320

Ser Val Asn Asp Ile Tyr Ala Ile Gly Glu Cys Ala Ser Trp Glu Asn
                325                 330                 335

Gln Thr Phe Gly Ile Ile Ala Pro Gly Ile Glu Met Ala Asp Val Leu
            340                 345                 350

Ser Phe Asn Leu Thr Asn Pro Asp Lys Glu Pro Lys Arg Phe Asn Arg
        355                 360                 365

Pro Asp Leu Ser Thr Lys Leu Lys Leu Leu Gly Val Asp Val Ala Ser
    370                 375                 380

Phe Gly Asp Phe Phe Ala Asp Arg Asp Gly Pro Lys Phe Leu Pro Gly
385                 390                 395                 400

Gln Arg Pro Ser Ala Glu Ser Ile Gly Ala Ala Asp Pro Asn Arg Glu
                405                 410                 415

Glu Glu Pro Gln Val Lys Ala Leu Thr Tyr Arg Asp Pro Phe Gly Gly
            420                 425                 430

Val Tyr Lys Lys Tyr Leu Phe Thr Met Asp Gly Lys Tyr Leu Leu Gly
        435                 440                 445

Gly Met Met Ile Gly Asp Thr Lys Asp Tyr Val Lys Leu Asn Gln Met
    450                 455                 460

Val Lys Ser Gln Lys Pro Leu Glu Val Pro Pro Ser Glu Phe Ile Leu
465                 470                 475                 480

Gly Ala Gln Ser Gly Gly Glu Glu Asn Ala Asp Asp Leu Asp Asp Ser
                485                 490                 495

Thr Gln Ile Cys Ser Cys His Asn Val Thr Lys Gly Asp Val Val Glu
            500                 505                 510

Ser Val Lys Ser Gly Thr Cys Lys Thr Ile Ala Asp Val Lys Ser Cys
        515                 520                 525

Thr Lys Ala Gly Thr Gly Cys Gly Gly Cys Met Pro Leu Val Gln Ser
    530                 535                 540

Ile Phe Asn Lys Thr Met Leu Asp Met Gly Gln Glu Val Ser Asn Asn
545                 550                 555                 560

Leu Cys Val His Ile Pro Tyr Ser Arg Ala Asp Leu Tyr Asn Val Ile
                565                 570                 575

Ala Ile Arg Gln Leu Arg Thr Phe Asp Asp Val Met Lys Ser Ala Gly
            580                 585                 590

Lys Cys Pro Asp Ser Leu Gly Cys Glu Ile Cys Lys Pro Ala Ile Ala
        595                 600                 605

Ser Ile Leu Ser Ser Leu Phe Asn Pro His Leu Met Asp Lys Glu Tyr
    610                 615                 620

His Glu Leu Gln Glu Thr Asn Asp Arg Phe Leu Ala Asn Ile Gln Arg
625                 630                 635                 640

Asn Gly Thr Phe Ser Val Val Pro Arg Val Pro Gly Gly Glu Ile Thr
                645                 650                 655

Ala Asp Lys Leu Ile Ala Ile Gly Gln Val Ala Lys Lys Tyr Asn Leu
            660                 665                 670

Tyr Cys Lys Ile Thr Gly Gly Gln Arg Ile Asp Met Phe Gly Ala Arg
        675                 680                 685

Lys Gln Asp Leu Leu Asp Ile Trp Thr Glu Leu Val Asp Ala Gly Met
    690                 695                 700

Glu Ser Gly His Ala Tyr Ala Lys Ser Leu Arg Thr Val Lys Ser Cys
705                 710                 715                 720
```

```
Val Gly Thr Thr Trp Cys Arg Phe Gly Val Gly Asp Ser Val Gly Met
            725                 730                 735

Ala Ile Arg Leu Glu Gln Arg Tyr Lys Ser Ile Arg Ala Pro His Lys
            740                 745                 750

Phe Lys Gly Ala Val Ser Gly Cys Val Arg Glu Cys Ala Glu Ala Gln
        755                 760                 765

Asn Lys Asp Phe Gly Leu Ile Ala Thr Glu Lys Gly Phe Asn Ile Phe
    770                 775                 780

Val Gly Gly Asn Gly Gly Ala Lys Pro Arg His Ser Glu Leu Leu Ala
785                 790                 795                 800

Lys Asp Val Pro Pro Glu Glu Val Ile Pro Ile Leu Asp Arg Tyr Val
            805                 810                 815

Ile Phe Tyr Ile Arg Thr Ala Asp Lys Leu Gln Arg Thr Ala Arg Trp
            820                 825                 830

Leu Glu Ser Leu Pro Gly Gly Ile Glu Tyr Leu Lys Asp Val Val Leu
        835                 840                 845

Asn Asp Lys Leu Gly Ile Ala Ala Glu Met Glu Arg Gln Met Gln Glu
    850                 855                 860

Leu Val Asp Ser Tyr Phe Cys Glu Trp Thr Glu Thr Val Arg Asn Pro
865                 870                 875                 880

Lys Arg Arg Lys Tyr Phe Gln Gln Phe Ala Asn Thr Asp Glu Thr Val
            885                 890                 895

Glu Asn Val Glu Ile Val Lys Glu Arg Glu Gln Val Arg Pro Thr Tyr
            900                 905                 910

Trp Pro Lys Asp Gly Ala Asn Glu Asp Phe Lys Gly His Gln Trp Ser
        915                 920                 925

Ser Leu Ser Trp Gln Pro Val Ile Lys Ala Asp Tyr Phe Ser Asp Gly
    930                 935                 940

Pro Pro Ala Ile Ser Ser Ala Asn Ile Lys Arg Gly Asp Thr Gln Leu
945                 950                 955                 960

Ala Ile Phe Lys Val Lys Gly Lys Tyr Tyr Ala Thr Gln Gln Met Cys
            965                 970                 975

Pro His Lys Arg Thr Phe Val Leu Ser Asp Gly Leu Ile Gly Asp Asp
            980                 985                 990

Asp Asn Gly Lys Tyr Trp Val Ser  Cys Pro Tyr His Lys  Arg Asn Phe
        995                 1000                1005

Glu Leu  Asn Gly Glu Gln Ala  Gly Arg Cys Gln Asn  Asp Glu Ala
    1010                1015                1020

Met Asn  Ile Ala Thr Phe Pro  Val Glu Glu Arg Glu  Asp Gly Trp
    1025                1030                1035

Ile Tyr  Met Lys Leu Pro Pro  Val Glu Glu Leu Asp  Ser Val Leu
    1040                1045                1050

Gly Thr  Glu Lys Trp Lys Val  Lys Lys Gly Glu Ala  Val Asp Pro
    1055                1060                1065

Phe Glu  Ala Tyr Asp Lys Lys  Tyr Ser Gly Met Lys  Gly Lys Arg
    1070                1075                1080

Ala Gly  Ala Lys Gly Ile Glu  Gly Ser Lys Pro Thr  Arg Ser Pro
    1085                1090                1095

Ser Asn  Thr Ile Asp Trp
    1100
```

<210> SEQ ID NO 6
<211> LENGTH: 508
<212> TYPE: PRT

<213> ORGANISM: Ogataea angusta
<220> FEATURE:
<221> NAME/KEY: MISC_FEATURE
<222> LOCATION: (1)..(508)
<223> OTHER INFORMATION: YNT1 Nitrate/Nitrite transporter Pichia angusta (Hansenula polymorpha)

<400> SEQUENCE: 6

```
Met Gln Leu Ser Thr Leu Trp Glu Pro Pro Ile Val Asn Pro Arg Asn
1               5                   10                  15

Leu Lys Ala Thr Ser Ile Pro Ile Phe Asn Leu Trp Asn Val Tyr Gly
            20                  25                  30

Arg Asn Phe Phe Phe Gly Trp Phe Gly Phe Phe Val Cys Phe Leu Ser
        35                  40                  45

Trp Phe Ala Phe Pro Pro Leu Leu His Gly Met Leu Lys Lys Asp Leu
    50                  55                  60

Arg Leu Thr Ala Val Asp Ile Ser Asn Asn Asn Ile Cys Gly Leu Thr
65                  70                  75                  80

Gly Thr Leu Leu Gly Arg Phe Ile Leu Gly Pro Leu Asn Asp Lys Tyr
                85                  90                  95

Gly Pro Arg Ile Thr Leu Thr Gly Val Leu Val Ala Gly Ala Ile Pro
            100                 105                 110

Thr Ala Phe Val Pro Leu Val Thr Asn Val Ala Gly Leu His Ala Ile
        115                 120                 125

Arg Phe Phe Ile Ser Phe Leu Gly Ser Ser Phe Ile Cys Cys Ser Gln
    130                 135                 140

Phe Cys Ala Val Phe Phe Asp Asn Asn Ile Ile Gly Thr Ala Asn Ala
145                 150                 155                 160

Ile Ser Ala Gly Trp Gly Asn Ala Gly Gly Gly Val Ala Phe Phe Val
                165                 170                 175

Met Pro Ala Ile Ser Asn Ala Leu Glu Asn Arg Gly Tyr Ser Leu His
            180                 185                 190

His Ser Trp Ser Tyr Ser Phe Val Ile Gly Pro Phe Leu Ile Leu Met
        195                 200                 205

Ile Thr Ala Ile Leu Ile Phe Val Phe Gly Ser Asp Cys Pro Arg Gly
    210                 215                 220

Arg Trp Ser Leu Arg Gly Asp Ile Leu Gly Ile Asn Met Asp Asn Met
225                 230                 235                 240

Leu Val Lys Ser Val Ser Val Thr Arg His Phe Ser Lys Glu Gly Glu
                245                 250                 255

Leu Thr Ser Val Phe Val Glu Pro Val Asn Ala Ile Asp Lys Val Val
            260                 265                 270

Val Glu Pro Asn Gln Asp Gln Glu Ile Leu Glu Val Ala Asp Ile Ile
        275                 280                 285

Asn Gly Asp Glu Ile Ile Glu Asp Pro Ser Leu Asn Asp Val Val Lys
    290                 295                 300

Ile Cys Leu Ser Pro Arg Thr Met Leu Val Gly Leu Cys Tyr Met Cys
305                 310                 315                 320

Ser Phe Gly Thr Glu Leu Ala Val Glu Ser Ile Ile Ser Asn Leu Phe
                325                 330                 335

Gly Gln Lys Met Thr Asn Trp Ser Thr Ser Lys Ala Gly Ala Trp Gly
            340                 345                 350

Ser Met Leu Gly Leu Leu Asn Val Val Ala Arg Pro Ala Gly Gly Ile
        355                 360                 365

Ile Ser Asp Phe Leu Tyr Gln Arg Phe Lys Thr Thr Lys Ala Lys Lys
```

```
    370                 375                 380

Phe Trp Met Ile Phe Thr Gly Leu Met Gln Gly Ile Phe Leu Ile Trp
385                 390                 395                 400

Ile Gly Leu Val Pro Glu Leu Ser Ile Ala Gly Leu Ile Val Ser Val
                405                 410                 415

Ser Phe Leu Cys Leu Trp Phe Glu Met Gly Asn Gly Ala Asn Tyr Ala
            420                 425                 430

Cys Val Pro Val Val Asn Arg His His Ser Gly Ile Val Ser Gly Val
        435                 440                 445

Thr Gly Ala Met Gly Asn Leu Gly Gly Ile Leu Phe Ser Leu Val Phe
    450                 455                 460

Arg Tyr Thr Ile Ser Asn Gly Val Asn Asn Tyr Phe Lys Ala Phe Trp
465                 470                 475                 480

Ile Ile Gly Ile Val Cys Thr Ala Val Asn Leu Val Cys Val Leu Ile
                485                 490                 495

Pro Ile Arg Glu Glu Arg Pro Arg Lys Ala Glu Asn
            500                 505


<210> SEQ ID NO 7
<211> LENGTH: 329
<212> TYPE: PRT
<213> ORGANISM: Escherichia coli
<220> FEATURE:
<221> NAME/KEY: MISC_FEATURE
<222> LOCATION: (1)..(329)
<223> OTHER INFORMATION: GTP 3',8-cyclase (moaA)

<400> SEQUENCE: 7

Met Ala Ser Gln Leu Thr Asp Ala Phe Ala Arg Lys Phe Tyr Tyr Leu
1               5                   10                  15

Arg Leu Ser Ile Thr Asp Val Cys Asn Phe Arg Cys Thr Tyr Cys Leu
            20                  25                  30

Pro Asp Gly Tyr Lys Pro Ser Gly Val Thr Asn Lys Gly Phe Leu Thr
        35                  40                  45

Val Asp Glu Ile Arg Arg Val Thr Arg Ala Phe Ala Arg Leu Gly Thr
    50                  55                  60

Glu Lys Val Arg Leu Thr Gly Gly Glu Pro Ser Leu Arg Arg Asp Phe
65                  70                  75                  80

Thr Asp Ile Ile Ala Ala Val Arg Glu Asn Asp Ala Ile Arg Gln Ile
                85                  90                  95

Ala Val Thr Thr Asn Gly Tyr Arg Leu Glu Arg Asp Val Ala Ser Trp
            100                 105                 110

Arg Asp Ala Gly Leu Thr Gly Ile Asn Val Ser Val Asp Ser Leu Asp
        115                 120                 125

Ala Arg Gln Phe His Ala Ile Thr Gly Gln Asp Lys Phe Asn Gln Val
    130                 135                 140

Met Ala Gly Ile Asp Ala Ala Phe Glu Ala Gly Phe Glu Lys Val Lys
145                 150                 155                 160

Val Asn Thr Val Leu Met Arg Asp Val Asn His His Gln Leu Asp Thr
                165                 170                 175

Phe Leu Asn Trp Ile Gln His Arg Pro Ile Gln Leu Arg Phe Ile Glu
            180                 185                 190

Leu Met Glu Thr Gly Glu Gly Ser Glu Leu Phe Arg Lys His His Ile
        195                 200                 205

Ser Gly Gln Val Leu Arg Asp Glu Leu Leu Arg Arg Gly Trp Ile His
    210                 215                 220
```

```
Gln Leu Arg Gln Arg Ser Asp Gly Pro Ala Gln Val Phe Cys His Pro
225                 230                 235                 240

Asp Tyr Ala Gly Glu Ile Gly Leu Ile Met Pro Tyr Glu Lys Asp Phe
                245                 250                 255

Cys Ala Thr Cys Asn Arg Leu Arg Val Ser Ser Ile Gly Lys Leu His
            260                 265                 270

Leu Cys Leu Phe Gly Glu Gly Gly Val Asn Leu Arg Asp Leu Leu Glu
        275                 280                 285

Asp Asp Thr Gln Gln Gln Ala Leu Glu Ala Arg Ile Ser Ala Ala Leu
    290                 295                 300

Arg Glu Lys Lys Gln Thr His Phe Leu His Gln Asn Asn Thr Gly Ile
305                 310                 315                 320

Thr Gln Asn Leu Ser Tyr Ile Gly Gly
                325


<210> SEQ ID NO 8
<211> LENGTH: 161
<212> TYPE: PRT
<213> ORGANISM: Escherichia coli
<220> FEATURE:
<221> NAME/KEY: MISC_FEATURE
<222> LOCATION: (1)..(161)
<223> OTHER INFORMATION: Cyclic pyranopterin monophosphate synthase
      (MoaC)

<400> SEQUENCE: 8

Met Ser Gln Leu Thr His Ile Asn Ala Ala Gly Glu Ala His Met Val
1               5                   10                  15

Asp Val Ser Ala Lys Ala Glu Thr Val Arg Glu Ala Arg Ala Glu Ala
            20                  25                  30

Phe Val Thr Met Arg Ser Glu Thr Leu Ala Met Ile Ile Asp Gly Arg
        35                  40                  45

His His Lys Gly Asp Val Phe Ala Thr Ala Arg Ile Ala Gly Ile Gln
    50                  55                  60

Ala Ala Lys Arg Thr Trp Asp Leu Ile Pro Leu Cys His Pro Leu Met
65                  70                  75                  80

Leu Ser Lys Val Glu Val Asn Leu Gln Ala Glu Pro Glu His Asn Arg
                85                  90                  95

Val Arg Ile Glu Thr Leu Cys Arg Leu Thr Gly Lys Thr Gly Val Glu
            100                 105                 110

Met Glu Ala Leu Thr Ala Ala Ser Val Ala Ala Leu Thr Ile Tyr Asp
        115                 120                 125

Met Cys Lys Ala Val Gln Lys Asp Met Val Ile Gly Pro Val Arg Leu
    130                 135                 140

Leu Ala Lys Ser Gly Gly Lys Ser Gly Asp Phe Lys Val Glu Ala Asp
145                 150                 155                 160

Asp


<210> SEQ ID NO 9
<211> LENGTH: 81
<212> TYPE: PRT
<213> ORGANISM: Escherichia coli
<220> FEATURE:
<221> NAME/KEY: MISC_FEATURE
<222> LOCATION: (1)..(81)
<223> OTHER INFORMATION: Molybdopterin synthase sulfur carrier subunit
      (MoaD)

<400> SEQUENCE: 9
```

Met Ile Lys Val Leu Phe Phe Ala Gln Val Arg Glu Leu Val Gly Thr
1 5 10 15

Asp Ala Thr Glu Val Ala Ala Asp Phe Pro Thr Val Glu Ala Leu Arg
20 25 30

Gln His Met Ala Ala Gln Ser Asp Arg Trp Ala Leu Ala Leu Glu Asp
35 40 45

Gly Lys Leu Leu Ala Ala Val Asn Gln Thr Leu Val Ser Phe Asp His
50 55 60

Pro Leu Thr Asp Gly Asp Glu Val Ala Phe Phe Pro Pro Val Thr Gly
65 70 75 80

Gly

<210> SEQ ID NO 10
<211> LENGTH: 150
<212> TYPE: PRT
<213> ORGANISM: Escherichia coli
<220> FEATURE:
<221> NAME/KEY: MISC_FEATURE
<222> LOCATION: (1)..(150)
<223> OTHER INFORMATION: Molybdopterin synthase catalytic subunit (MoaE)

<400> SEQUENCE: 10

Met Ala Glu Thr Lys Ile Val Val Gly Pro Gln Pro Phe Ser Val Gly
1 5 10 15

Glu Glu Tyr Pro Trp Leu Ala Glu Arg Asp Glu Asp Gly Ala Val Val
20 25 30

Thr Phe Thr Gly Lys Val Arg Asn His Asn Leu Gly Asp Ser Val Asn
35 40 45

Ala Leu Thr Leu Glu His Tyr Pro Gly Met Thr Glu Lys Ala Leu Ala
50 55 60

Glu Ile Val Asp Glu Ala Arg Asn Arg Trp Pro Leu Gly Arg Val Thr
65 70 75 80

Val Ile His Arg Ile Gly Glu Leu Trp Pro Gly Asp Glu Ile Val Phe
85 90 95

Val Gly Val Thr Ser Ala His Arg Ser Ser Ala Phe Glu Ala Gly Gln
100 105 110

Phe Ile Met Asp Tyr Leu Lys Thr Arg Ala Pro Phe Trp Lys Arg Glu
115 120 125

Ala Thr Pro Glu Gly Asp Arg Trp Val Glu Ala Arg Glu Ser Asp Gln
130 135 140

Gln Ala Ala Lys Arg Trp
145 150

<210> SEQ ID NO 11
<211> LENGTH: 194
<212> TYPE: PRT
<213> ORGANISM: Escherichia coli
<220> FEATURE:
<221> NAME/KEY: MISC_FEATURE
<222> LOCATION: (1)..(194)
<223> OTHER INFORMATION: Molybdenum cofactor guanylyltransferase (MobA)

<400> SEQUENCE: 11

Met Asn Leu Met Thr Thr Ile Thr Gly Val Val Leu Ala Gly Gly Lys
1 5 10 15

Ala Arg Arg Met Gly Gly Val Asp Lys Gly Leu Leu Glu Leu Asn Gly
20 25 30

Lys Pro Leu Trp Gln His Val Ala Asp Ala Leu Met Thr Gln Leu Ser

```
        35                  40                  45

His Val Val Val Asn Ala Asn Arg His Gln Glu Ile Tyr Gln Ala Ser
    50                  55                  60

Gly Leu Lys Val Ile Glu Asp Ser Leu Ala Asp Tyr Pro Gly Pro Leu
65                  70                  75                  80

Ala Gly Met Leu Ser Val Met Gln Gln Glu Ala Gly Glu Trp Phe Leu
                85                  90                  95

Phe Cys Pro Cys Asp Thr Pro Tyr Ile Pro Pro Asp Leu Ala Ala Arg
            100                 105                 110

Leu Asn His Gln Arg Lys Asp Ala Pro Val Val Trp Val His Asp Gly
        115                 120                 125

Glu Arg Asp His Pro Thr Ile Ala Leu Val Asn Arg Ala Ile Glu Pro
    130                 135                 140

Leu Leu Leu Glu Tyr Leu Gln Ala Gly Glu Arg Arg Val Met Val Phe
145                 150                 155                 160

Met Arg Leu Ala Gly Gly His Ala Val Asp Phe Ser Asp His Lys Asp
                165                 170                 175

Ala Phe Val Asn Val Asn Thr Pro Glu Glu Leu Ala Arg Trp Gln Glu
            180                 185                 190

Lys Arg


<210> SEQ ID NO 12
<211> LENGTH: 175
<212> TYPE: PRT
<213> ORGANISM: Escherichia coli
<220> FEATURE:
<221> NAME/KEY: MISC_FEATURE
<222> LOCATION: (1)..(175)
<223> OTHER INFORMATION: Molybdopterin-guanine dinucleotide biosynthesis
      adapter protein (MobB)

<400> SEQUENCE: 12

Met Ala Gly Lys Thr Met Ile Pro Leu Leu Ala Phe Ala Ala Trp Ser
1               5                   10                  15

Gly Thr Gly Lys Thr Thr Leu Leu Lys Lys Leu Ile Pro Ala Leu Cys
            20                  25                  30

Ala Arg Gly Ile Arg Pro Gly Leu Ile Lys His Thr His His Asp Met
        35                  40                  45

Asp Val Asp Lys Pro Gly Lys Asp Ser Tyr Glu Leu Arg Lys Ala Gly
    50                  55                  60

Ala Ala Gln Thr Ile Val Ala Ser Gln Gln Arg Trp Ala Leu Met Thr
65                  70                  75                  80

Glu Thr Pro Asp Glu Glu Glu Leu Asp Leu Gln Phe Leu Ala Ser Arg
                85                  90                  95

Met Asp Thr Ser Lys Leu Asp Leu Ile Leu Val Glu Gly Phe Lys His
            100                 105                 110

Glu Glu Ile Ala Lys Ile Val Leu Phe Arg Asp Gly Ala Gly His Arg
        115                 120                 125

Pro Glu Glu Leu Val Ile Asp Arg His Val Ile Ala Val Ala Ser Asp
    130                 135                 140

Val Pro Leu Asn Leu Asp Val Ala Leu Leu Asp Ile Asn Asp Val Glu
145                 150                 155                 160

Gly Leu Ala Asp Phe Val Val Glu Trp Met Gln Lys Gln Asn Gly
                165                 170                 175


<210> SEQ ID NO 13
```

```
<211> LENGTH: 192
<212> TYPE: PRT
<213> ORGANISM: Escherichia coli
<220> FEATURE:
<221> NAME/KEY: MISC_FEATURE
<222> LOCATION: (1)..(192)
<223> OTHER INFORMATION: Molybdenum cofactor cytidylyltransferase (MocA)

<400> SEQUENCE: 13

Met Ser Ala Ile Asp Cys Ile Ile Thr Ala Ala Gly Leu Ser Ser Arg
1               5                   10                  15

Met Gly Gln Trp Lys Met Met Leu Pro Trp Glu Gln Gly Thr Ile Leu
            20                  25                  30

Asp Thr Ser Ile Lys Asn Ala Leu Gln Phe Cys Ser Arg Ile Ile Leu
        35                  40                  45

Val Thr Gly Tyr Arg Gly Asn Glu Leu His Glu Arg Tyr Ala Asn Gln
    50                  55                  60

Ser Asn Ile Thr Ile Ile His Asn Pro Asp Tyr Ala Gln Gly Leu Leu
65                  70                  75                  80

Thr Ser Val Lys Ala Ala Val Pro Ala Val Gln Thr Glu His Cys Phe
                85                  90                  95

Leu Thr His Gly Asp Met Pro Thr Leu Thr Ile Asp Ile Phe Arg Lys
            100                 105                 110

Ile Trp Ser Leu Arg Asn Asp Gly Ala Ile Leu Pro Leu His Asn Gly
        115                 120                 125

Ile Pro Gly His Pro Ile Leu Val Ser Lys Pro Cys Leu Met Gln Ala
    130                 135                 140

Ile Gln Arg Pro Asn Val Thr Asn Met Arg Gln Ala Leu Leu Met Gly
145                 150                 155                 160

Asp His Tyr Ser Val Glu Ile Glu Asn Ala Glu Ile Ile Leu Asp Ile
                165                 170                 175

Asp Thr Pro Asp Asp Phe Ile Thr Ala Lys Glu Arg Tyr Thr Glu Ile
            180                 185                 190


<210> SEQ ID NO 14
<211> LENGTH: 257
<212> TYPE: PRT
<213> ORGANISM: Escherichia coli
<220> FEATURE:
<221> NAME/KEY: MISC_FEATURE
<222> LOCATION: (1)..(257)
<223> OTHER INFORMATION: Molybdate-binding protein (ModA)

<400> SEQUENCE: 14

Met Ala Arg Lys Trp Leu Asn Leu Phe Ala Gly Ala Ala Leu Ser Phe
1               5                   10                  15

Ala Val Ala Gly Asn Ala Leu Ala Asp Glu Gly Lys Ile Thr Val Phe
            20                  25                  30

Ala Ala Ala Ser Leu Thr Asn Ala Met Gln Asp Ile Ala Thr Gln Phe
        35                  40                  45

Lys Lys Glu Lys Gly Val Asp Val Val Ser Ser Phe Ala Ser Ser Ser
    50                  55                  60

Thr Leu Ala Arg Gln Ile Glu Ala Gly Ala Pro Ala Asp Leu Phe Ile
65                  70                  75                  80

Ser Ala Asp Gln Lys Trp Met Asp Tyr Ala Val Asp Lys Lys Ala Ile
                85                  90                  95

Asp Thr Ala Thr Arg Gln Thr Leu Leu Gly Asn Ser Leu Val Val Val
            100                 105                 110
```

```
Ala Pro Lys Ala Ser Val Gln Lys Asp Phe Thr Ile Asp Ser Lys Thr
        115                 120                 125

Asn Trp Thr Ser Leu Leu Asn Gly Gly Arg Leu Ala Val Gly Asp Pro
    130                 135                 140

Glu His Val Pro Ala Gly Ile Tyr Ala Lys Glu Ala Leu Gln Lys Leu
145                 150                 155                 160

Gly Ala Trp Asp Thr Leu Ser Pro Lys Leu Ala Pro Ala Glu Asp Val
                165                 170                 175

Arg Gly Ala Leu Ala Leu Val Glu Arg Asn Glu Ala Pro Leu Gly Ile
            180                 185                 190

Val Tyr Gly Ser Asp Ala Val Ala Ser Lys Gly Val Lys Val Val Ala
        195                 200                 205

Thr Phe Pro Glu Asp Ser His Lys Lys Val Glu Tyr Pro Val Ala Val
    210                 215                 220

Val Glu Gly His Asn Asn Ala Thr Val Lys Ala Phe Tyr Asp Tyr Leu
225                 230                 235                 240

Lys Gly Pro Gln Ala Ala Glu Ile Phe Lys Arg Tyr Gly Phe Thr Ile
                245                 250                 255

Lys


<210> SEQ ID NO 15
<211> LENGTH: 180
<212> TYPE: PRT
<213> ORGANISM: Escherichia coli
<220> FEATURE:
<221> NAME/KEY: MISC_FEATURE
<222> LOCATION: (1)..(180)
<223> OTHER INFORMATION: ModB_BPT4 NAD--protein ADP-ribosyltransferase
      modB

<400> SEQUENCE: 15

Met Ile Ile Asn Leu Ala Asp Val Glu Gln Leu Ser Ile Lys Ala Glu
1               5                   10                  15

Ser Val Asp Phe Gln Tyr Asp Met Tyr Lys Lys Val Cys Glu Lys Phe
            20                  25                  30

Thr Asp Phe Glu Gln Ser Val Leu Trp Gln Cys Met Glu Ala Lys Lys
        35                  40                  45

Asn Glu Ala Leu His Lys His Leu Asn Glu Ile Ile Lys Lys His Leu
    50                  55                  60

Thr Lys Ser Pro Tyr Gln Leu Tyr Arg Gly Ile Ser Lys Ser Thr Lys
65                  70                  75                  80

Glu Leu Ile Lys Asp Leu Gln Val Gly Glu Val Phe Ser Thr Asn Arg
                85                  90                  95

Val Asp Ser Phe Thr Thr Ser Leu His Thr Ala Cys Ser Phe Ser Tyr
            100                 105                 110

Ala Glu Tyr Phe Thr Glu Thr Ile Leu Arg Leu Lys Thr Asp Lys Ala
        115                 120                 125

Phe Asn Tyr Ser Asp His Ile Ser Asp Ile Ile Leu Ser Ser Pro Asn
    130                 135                 140

Thr Glu Phe Lys Tyr Thr Tyr Glu Asp Thr Asp Gly Leu Asp Ser Glu
145                 150                 155                 160

Arg Thr Asp Asn Leu Met Met Ile Val Arg Glu Gln Glu Trp Met Ile
                165                 170                 175

Pro Ile Gly Lys
            180
```

<210> SEQ ID NO 16
<211> LENGTH: 352
<212> TYPE: PRT
<213> ORGANISM: Escherichia coli
<220> FEATURE:
<221> NAME/KEY: MISC_FEATURE
<222> LOCATION: (1)..(352)
<223> OTHER INFORMATION: Molybdenum import ATP-binding protein (ModC)

<400> SEQUENCE: 16

```
Met Leu Glu Leu Asn Phe Ser Gln Thr Leu Gly Asn His Cys Leu Thr
1               5                   10                  15

Ile Asn Glu Thr Leu Pro Ala Asn Gly Ile Thr Ala Ile Phe Gly Val
            20                  25                  30

Ser Gly Ala Gly Lys Thr Ser Leu Ile Asn Ala Ile Ser Gly Leu Thr
        35                  40                  45

Arg Pro Gln Lys Gly Arg Ile Val Leu Asn Gly Arg Val Leu Asn Asp
    50                  55                  60

Ala Glu Lys Gly Ile Cys Leu Thr Pro Glu Lys Arg Arg Val Gly Tyr
65                  70                  75                  80

Val Phe Gln Asp Ala Arg Leu Phe Pro His Tyr Lys Val Arg Gly Asn
                85                  90                  95

Leu Arg Tyr Gly Met Ser Lys Ser Met Val Asp Gln Phe Asp Lys Leu
            100                 105                 110

Val Ala Leu Leu Gly Ile Glu Pro Leu Leu Asp Arg Leu Pro Gly Ser
        115                 120                 125

Leu Ser Gly Gly Glu Lys Gln Arg Val Ala Ile Gly Arg Ala Leu Leu
    130                 135                 140

Thr Ala Pro Glu Leu Leu Leu Leu Asp Glu Pro Leu Ala Ser Leu Asp
145                 150                 155                 160

Ile Pro Arg Lys Arg Glu Leu Leu Pro Tyr Leu Gln Arg Leu Thr Arg
                165                 170                 175

Glu Ile Asn Ile Pro Met Leu Tyr Val Ser His Ser Leu Asp Glu Ile
            180                 185                 190

Leu His Leu Ala Asp Arg Val Met Val Leu Glu Asn Gly Gln Val Lys
        195                 200                 205

Ala Phe Gly Ala Leu Glu Glu Val Trp Gly Ser Ser Val Met Asn Pro
    210                 215                 220

Trp Leu Pro Lys Glu Gln Gln Ser Ser Ile Leu Lys Val Thr Val Leu
225                 230                 235                 240

Glu His His Pro His Tyr Ala Met Thr Ala Leu Ala Leu Gly Asp Gln
                245                 250                 255

His Leu Trp Val Asn Lys Leu Asp Glu Pro Leu Gln Ala Ala Leu Arg
            260                 265                 270

Ile Arg Ile Gln Ala Ser Asp Val Ser Leu Val Leu Gln Pro Pro Gln
        275                 280                 285

Gln Thr Ser Ile Arg Asn Val Leu Arg Ala Lys Val Val Asn Ser Tyr
    290                 295                 300

Asp Asp Asn Gly Gln Val Glu Val Glu Leu Glu Val Gly Gly Lys Thr
305                 310                 315                 320

Leu Trp Ala Arg Ile Ser Pro Trp Ala Arg Asp Glu Leu Ala Ile Lys
                325                 330                 335

Pro Gly Leu Trp Leu Tyr Ala Gln Ile Lys Ser Val Ser Ile Thr Ala
            340                 345                 350
```

<210> SEQ ID NO 17

```
<211> LENGTH: 289
<212> TYPE: PRT
<213> ORGANISM: Escherichia coli
<220> FEATURE:
<221> NAME/KEY: MISC_FEATURE
<222> LOCATION: (1)..(289)
<223> OTHER INFORMATION: DNA-binding transcriptional dual regulator
      (ModE)

<400> SEQUENCE: 17

Met Gln Ala Glu Ile Leu Leu Thr Leu Lys Leu Gln Gln Lys Leu Phe
1               5                   10                  15

Ala Asp Pro Arg Arg Ile Ser Leu Leu Lys His Ile Ala Leu Ser Gly
            20                  25                  30

Ser Ile Ser Gln Gly Ala Lys Asp Ala Gly Ile Ser Tyr Lys Ser Ala
        35                  40                  45

Trp Asp Ala Ile Asn Glu Met Asn Gln Leu Ser Glu His Ile Leu Val
    50                  55                  60

Glu Arg Ala Thr Gly Gly Lys Gly Gly Gly Gly Ala Val Leu Thr Arg
65                  70                  75                  80

Tyr Gly Gln Arg Leu Ile Gln Leu Tyr Asp Leu Leu Ala Gln Ile Gln
                85                  90                  95

Gln Lys Ala Phe Asp Val Leu Ser Asp Asp Asp Ala Leu Pro Leu Asn
            100                 105                 110

Ser Leu Leu Ala Ala Ile Ser Arg Phe Ser Leu Gln Thr Ser Ala Arg
        115                 120                 125

Asn Gln Trp Phe Gly Thr Ile Thr Ala Arg Asp His Asp Asp Val Gln
    130                 135                 140

Gln His Val Asp Val Leu Leu Ala Asp Gly Lys Thr Arg Leu Lys Val
145                 150                 155                 160

Ala Ile Thr Ala Gln Ser Gly Ala Arg Leu Gly Leu Asp Glu Gly Lys
                165                 170                 175

Glu Val Leu Ile Leu Leu Lys Ala Pro Trp Val Gly Ile Thr Gln Asp
            180                 185                 190

Glu Ala Val Ala Gln Asn Ala Asp Asn Gln Leu Pro Gly Ile Ile Ser
        195                 200                 205

His Ile Glu Arg Gly Ala Glu Gln Cys Glu Val Leu Met Ala Leu Pro
    210                 215                 220

Asp Gly Gln Thr Leu Cys Ala Thr Val Pro Val Asn Glu Ala Thr Ser
225                 230                 235                 240

Leu Gln Gln Gly Gln Asn Val Thr Ala Tyr Phe Asn Ala Asp Ser Val
                245                 250                 255

Ile Ile Ala Thr Leu Cys Tyr Lys Ile Thr Ser Ile Ser Lys Glu Lys
            260                 265                 270

Leu His Asp Ser Phe Gly Thr Phe Lys Val Tyr Asp Ile Glu Val Val
        275                 280                 285

Glu


<210> SEQ ID NO 18
<211> LENGTH: 411
<212> TYPE: PRT
<213> ORGANISM: Escherichia coli
<220> FEATURE:
<221> NAME/KEY: MISC_FEATURE
<222> LOCATION: (1)..(411)
<223> OTHER INFORMATION: Molybdopterin molybdenumtransferase (MoeA)

<400> SEQUENCE: 18
```

-continued

```
Met Glu Phe Thr Thr Gly Leu Met Ser Leu Asp Thr Ala Leu Asn Glu
1               5                   10                  15

Met Leu Ser Arg Val Thr Pro Leu Thr Ala Gln Glu Thr Leu Pro Leu
            20                  25                  30

Val Gln Cys Phe Gly Arg Ile Leu Ala Ser Asp Val Val Ser Pro Leu
        35                  40                  45

Asp Val Pro Gly Phe Asp Asn Ser Ala Met Asp Gly Tyr Ala Val Arg
    50                  55                  60

Leu Ala Asp Ile Ala Ser Gly Gln Pro Leu Pro Val Ala Gly Lys Ser
65                  70                  75                  80

Phe Ala Gly Gln Pro Tyr His Gly Glu Trp Pro Ala Gly Thr Cys Ile
                85                  90                  95

Arg Ile Met Thr Gly Ala Pro Val Pro Glu Gly Cys Glu Ala Val Val
            100                 105                 110

Met Gln Glu Gln Thr Glu Gln Met Asp Asn Gly Val Arg Phe Thr Ala
        115                 120                 125

Glu Val Arg Ser Gly Gln Asn Ile Arg Arg Arg Gly Glu Asp Ile Ser
    130                 135                 140

Ala Gly Ala Val Val Phe Pro Ala Gly Thr Arg Leu Thr Thr Ala Glu
145                 150                 155                 160

Leu Pro Val Ile Ala Ser Leu Gly Ile Ala Glu Val Pro Val Ile Arg
                165                 170                 175

Lys Val Arg Val Ala Leu Phe Ser Thr Gly Asp Glu Leu Gln Leu Pro
            180                 185                 190

Gly Gln Pro Leu Gly Asp Gly Gln Ile Tyr Asp Thr Asn Arg Leu Ala
        195                 200                 205

Val His Leu Met Leu Glu Gln Leu Gly Cys Glu Val Ile Asn Leu Gly
    210                 215                 220

Ile Ile Arg Asp Asp Pro His Ala Leu Arg Ala Ala Phe Ile Glu Ala
225                 230                 235                 240

Asp Ser Gln Ala Asp Val Val Ile Ser Ser Gly Gly Val Ser Val Gly
                245                 250                 255

Glu Ala Asp Tyr Thr Lys Thr Ile Leu Glu Glu Leu Gly Glu Ile Ala
            260                 265                 270

Phe Trp Lys Leu Ala Ile Lys Pro Gly Lys Pro Phe Ala Phe Gly Lys
        275                 280                 285

Leu Ser Asn Ser Trp Phe Cys Gly Leu Pro Gly Asn Pro Val Ser Ala
    290                 295                 300

Thr Leu Thr Phe Tyr Gln Leu Val Gln Pro Leu Leu Ala Lys Leu Ser
305                 310                 315                 320

Gly Asn Thr Ala Ser Gly Leu Pro Ala Arg Gln Arg Val Arg Thr Ala
                325                 330                 335

Ser Arg Leu Lys Lys Thr Pro Gly Arg Leu Asp Phe Gln Arg Gly Val
            340                 345                 350

Leu Gln Arg Asn Ala Asp Gly Glu Leu Glu Val Thr Thr Thr Gly His
        355                 360                 365

Gln Gly Ser His Ile Phe Ser Ser Phe Ser Leu Gly Asn Cys Phe Ile
    370                 375                 380

Val Leu Glu Arg Asp Arg Gly Asn Val Glu Val Gly Glu Trp Val Glu
385                 390                 395                 400

Val Glu Pro Phe Asn Ala Leu Phe Gly Gly Leu
                405                 410
```

<210> SEQ ID NO 19
<211> LENGTH: 249
<212> TYPE: PRT
<213> ORGANISM: Escherichia coli
<220> FEATURE:
<221> NAME/KEY: MISC_FEATURE
<222> LOCATION: (1)..(249)
<223> OTHER INFORMATION: Molybdopterin-synthase adenylyltransferase (MoeB)

<400> SEQUENCE: 19

```
Met Ala Glu Leu Ser Asp Gln Glu Met Leu Arg Tyr Asn Arg Gln Ile
1               5                   10                  15

Ile Leu Arg Gly Phe Asp Phe Asp Gly Gln Glu Ala Leu Lys Asp Ser
            20                  25                  30

Arg Val Leu Ile Val Gly Leu Gly Gly Leu Gly Cys Ala Ala Ser Gln
        35                  40                  45

Tyr Leu Ala Ser Ala Gly Val Gly Asn Leu Thr Leu Leu Asp Phe Asp
    50                  55                  60

Thr Val Ser Leu Ser Asn Leu Gln Arg Gln Thr Leu His Ser Asp Ala
65                  70                  75                  80

Thr Val Gly Gln Pro Lys Val Glu Ser Ala Arg Asp Ala Leu Thr Arg
                85                  90                  95

Ile Asn Pro His Ile Ala Ile Thr Pro Val Asn Ala Leu Leu Asp Asp
            100                 105                 110

Ala Glu Leu Ala Ala Leu Ile Ala Glu His Asp Leu Val Leu Asp Cys
        115                 120                 125

Thr Asp Asn Val Ala Val Arg Asn Gln Leu Asn Ala Gly Cys Phe Ala
    130                 135                 140

Ala Lys Val Pro Leu Val Ser Gly Ala Ala Ile Arg Met Glu Gly Gln
145                 150                 155                 160

Ile Thr Val Phe Thr Tyr Gln Asp Gly Glu Pro Cys Tyr Arg Cys Leu
                165                 170                 175

Ser Arg Leu Phe Gly Glu Asn Ala Leu Thr Cys Val Glu Ala Gly Val
            180                 185                 190

Met Ala Pro Leu Ile Gly Val Ile Gly Ser Leu Gln Ala Met Glu Ala
        195                 200                 205

Ile Lys Met Leu Ala Gly Tyr Gly Lys Pro Ala Ser Gly Lys Ile Val
    210                 215                 220

Met Tyr Asp Ala Met Thr Cys Gln Phe Arg Glu Met Lys Leu Met Arg
225                 230                 235                 240

Asn Pro Gly Cys Glu Val Cys Gly Gln
                245
```

<210> SEQ ID NO 20
<211> LENGTH: 195
<212> TYPE: PRT
<213> ORGANISM: Escherichia coli
<220> FEATURE:
<221> NAME/KEY: MISC_FEATURE
<222> LOCATION: (1)..(195)
<223> OTHER INFORMATION: Molybdopterin adenylyltransferase (MOG)

<400> SEQUENCE: 20

```
Met Asn Thr Leu Arg Ile Gly Leu Val Ser Ile Ser Asp Arg Ala Ser
1               5                   10                  15

Ser Gly Val Tyr Gln Asp Lys Gly Ile Pro Ala Leu Glu Glu Trp Leu
            20                  25                  30

Thr Ser Ala Leu Thr Thr Pro Phe Glu Leu Glu Thr Arg Leu Ile Pro
```

```
        35                  40                  45

Asp Glu Gln Ala Ile Ile Glu Gln Thr Leu Cys Glu Leu Val Asp Glu
    50                  55                  60

Met Ser Cys His Leu Val Leu Thr Thr Gly Gly Thr Gly Pro Ala Arg
65                  70                  75                  80

Arg Asp Val Thr Pro Asp Ala Thr Leu Ala Val Ala Asp Arg Glu Met
                85                  90                  95

Pro Gly Phe Gly Glu Gln Met Arg Gln Ile Ser Leu His Phe Val Pro
            100                 105                 110

Thr Ala Ile Leu Ser Arg Gln Val Gly Val Ile Arg Lys Gln Ala Leu
        115                 120                 125

Ile Leu Asn Leu Pro Gly Gln Pro Lys Ser Ile Lys Glu Thr Leu Glu
    130                 135                 140

Gly Val Lys Asp Ala Glu Gly Asn Val Val Val His Gly Ile Phe Ala
145                 150                 155                 160

Ser Val Pro Tyr Cys Ile Gln Leu Leu Glu Gly Pro Tyr Val Glu Thr
                165                 170                 175

Ala Pro Glu Val Val Ala Ala Phe Arg Pro Lys Ser Ala Arg Arg Asp
            180                 185                 190

Val Ser Glu
        195


<210> SEQ ID NO 21
<211> LENGTH: 404
<212> TYPE: PRT
<213> ORGANISM: Escherichia coli
<220> FEATURE:
<221> NAME/KEY: MISC_FEATURE
<222> LOCATION: (1)..(404)
<223> OTHER INFORMATION: Cysteine desulfurase IscS

<400> SEQUENCE: 21

Met Lys Leu Pro Ile Tyr Leu Asp Tyr Ser Ala Thr Thr Pro Val Asp
1               5                   10                  15

Pro Arg Val Ala Glu Lys Met Met Gln Phe Met Thr Met Asp Gly Thr
            20                  25                  30

Phe Gly Asn Pro Ala Ser Arg Ser His Arg Phe Gly Trp Gln Ala Glu
        35                  40                  45

Glu Ala Val Asp Ile Ala Arg Asn Gln Ile Ala Asp Leu Val Gly Ala
    50                  55                  60

Asp Pro Arg Glu Ile Val Phe Thr Ser Gly Ala Thr Glu Ser Asp Asn
65                  70                  75                  80

Leu Ala Ile Lys Gly Ala Ala Asn Phe Tyr Gln Lys Lys Gly Lys His
                85                  90                  95

Ile Ile Thr Ser Lys Thr Glu His Lys Ala Val Leu Asp Thr Cys Arg
            100                 105                 110

Gln Leu Glu Arg Glu Gly Phe Glu Val Thr Tyr Leu Ala Pro Gln Arg
        115                 120                 125

Asn Gly Ile Ile Asp Leu Lys Glu Leu Glu Ala Ala Met Arg Asp Asp
    130                 135                 140

Thr Ile Leu Val Ser Ile Met His Val Asn Asn Glu Ile Gly Val Val
145                 150                 155                 160

Gln Asp Ile Ala Ala Ile Gly Glu Met Cys Arg Ala Arg Gly Ile Ile
                165                 170                 175

Tyr His Val Asp Ala Thr Gln Ser Val Gly Lys Leu Pro Ile Asp Leu
            180                 185                 190
```

Ser Gln Leu Lys Val Asp Leu Met Ser Phe Ser Gly His Lys Ile Tyr
195 200 205

Gly Pro Lys Gly Ile Gly Ala Leu Tyr Val Arg Arg Lys Pro Arg Val
210 215 220

Arg Ile Glu Ala Gln Met His Gly Gly Gly His Glu Arg Gly Met Arg
225 230 235 240

Ser Gly Thr Leu Pro Val His Gln Ile Val Gly Met Gly Glu Ala Tyr
245 250 255

Arg Ile Ala Lys Glu Glu Met Ala Thr Glu Met Glu Arg Leu Arg Gly
260 265 270

Leu Arg Asn Arg Leu Trp Asn Gly Ile Lys Asp Ile Glu Glu Val Tyr
275 280 285

Leu Asn Gly Asp Leu Glu His Gly Ala Pro Asn Ile Leu Asn Val Ser
290 295 300

Phe Asn Tyr Val Glu Gly Glu Ser Leu Ile Met Ala Leu Lys Asp Leu
305 310 315 320

Ala Val Ser Ser Gly Ser Ala Cys Thr Ser Ala Ser Leu Glu Pro Ser
325 330 335

Tyr Val Leu Arg Ala Leu Gly Leu Asn Asp Glu Leu Ala His Ser Ser
340 345 350

Ile Arg Phe Ser Leu Gly Arg Phe Thr Thr Glu Glu Glu Ile Asp Tyr
355 360 365

Thr Ile Glu Leu Val Arg Lys Ser Ile Gly Arg Leu Arg Asp Leu Ser
370 375 380

Pro Leu Trp Glu Met Tyr Lys Gln Gly Val Asp Leu Asn Ser Ile Glu
385 390 395 400

Trp Ala His His

<210> SEQ ID NO 22
<211> LENGTH: 457
<212> TYPE: PRT
<213> ORGANISM: Escherichia coli
<220> FEATURE:
<221> NAME/KEY: MISC_FEATURE
<222> LOCATION: (1)..(457)
<223> OTHER INFORMATION: Siroheme synthase CysG

<400> SEQUENCE: 22

Met Asp His Leu Pro Ile Phe Cys Gln Leu Arg Asp Arg Asp Cys Leu
1 5 10 15

Ile Val Gly Gly Gly Asp Val Ala Glu Arg Lys Ala Arg Leu Leu Leu
20 25 30

Asp Ala Gly Ala Arg Leu Thr Val Asn Ala Leu Ala Phe Ile Pro Gln
35 40 45

Phe Thr Ala Trp Ala Asp Ala Gly Met Leu Thr Leu Val Glu Gly Pro
50 55 60

Phe Asp Glu Ser Leu Leu Asp Thr Cys Trp Leu Ala Ile Ala Ala Thr
65 70 75 80

Asp Asp Asp Ala Leu Asn Gln Arg Val Ser Glu Ala Ala Glu Ala Arg
85 90 95

Arg Ile Phe Cys Asn Val Val Asp Ala Pro Lys Ala Ala Ser Phe Ile
100 105 110

Met Pro Ser Ile Ile Asp Arg Ser Pro Leu Met Val Ala Val Ser Ser
115 120 125

Gly Gly Thr Ser Pro Val Leu Ala Arg Leu Leu Arg Glu Lys Leu Glu

```
    130                 135                 140

Ser Leu Leu Pro Leu His Leu Gly Gln Val Ala Lys Tyr Ala Gly Gln
145                 150                 155                 160

Leu Arg Gly Arg Val Lys Gln Gln Phe Ala Thr Met Gly Glu Arg Arg
                165                 170                 175

Arg Phe Trp Glu Lys Leu Phe Val Asn Asp Arg Leu Ala Gln Ser Leu
            180                 185                 190

Ala Asn Asn Asp Gln Lys Ala Ile Thr Glu Thr Thr Glu Gln Leu Ile
        195                 200                 205

Asn Glu Pro Leu Asp His Arg Gly Glu Val Val Leu Val Gly Ala Gly
    210                 215                 220

Pro Gly Asp Ala Gly Leu Leu Thr Leu Lys Gly Leu Gln Gln Ile Gln
225                 230                 235                 240

Gln Ala Asp Val Val Val Tyr Asp Arg Leu Val Ser Asp Asp Ile Met
                245                 250                 255

Asn Leu Val Arg Arg Asp Ala Asp Arg Val Phe Val Gly Lys Arg Ala
            260                 265                 270

Gly Tyr His Cys Val Pro Gln Glu Glu Ile Asn Gln Ile Leu Leu Arg
        275                 280                 285

Glu Ala Gln Lys Gly Lys Arg Val Val Arg Leu Lys Gly Gly Asp Pro
    290                 295                 300

Phe Ile Phe Gly Arg Gly Gly Glu Glu Leu Glu Thr Leu Cys Asn Ala
305                 310                 315                 320

Gly Ile Pro Phe Ser Val Val Pro Gly Ile Thr Ala Ala Ser Gly Cys
                325                 330                 335

Ser Ala Tyr Ser Gly Ile Pro Leu Thr His Arg Asp Tyr Ala Gln Ser
            340                 345                 350

Val Arg Leu Ile Thr Gly His Leu Lys Thr Gly Gly Glu Leu Asp Trp
        355                 360                 365

Glu Asn Leu Ala Ala Glu Lys Gln Thr Leu Val Phe Tyr Met Gly Leu
    370                 375                 380

Asn Gln Ala Ala Thr Ile Gln Gln Lys Leu Ile Glu His Gly Met Pro
385                 390                 395                 400

Gly Glu Met Pro Val Ala Ile Val Glu Asn Gly Thr Ala Val Thr Gln
                405                 410                 415

Arg Val Ile Asp Gly Thr Leu Thr Gln Leu Gly Glu Leu Ala Gln Gln
            420                 425                 430

Met Asn Ser Pro Ser Leu Ile Ile Ile Gly Arg Val Val Gly Leu Arg
        435                 440                 445

Asp Lys Leu Asn Trp Phe Ser Asn His
    450                 455


<210> SEQ ID NO 23
<211> LENGTH: 274
<212> TYPE: PRT
<213> ORGANISM: Saccharomyces cerevisiae
<220> FEATURE:
<221> NAME/KEY: MISC_FEATURE
<222> LOCATION: (1)..(274)
<223> OTHER INFORMATION: MET8_YEAST Siroheme biosynthesis protein MET8

<400> SEQUENCE: 23

Met Val Lys Ser Leu Gln Leu Ala His Gln Leu Lys Asp Lys Lys Ile
1               5                   10                  15

Leu Leu Ile Gly Gly Gly Glu Val Gly Leu Thr Arg Leu Tyr Lys Leu
            20                  25                  30
```

```
Ile Pro Thr Gly Cys Lys Leu Thr Leu Val Ser Pro Asp Leu His Lys
        35                  40                  45

Ser Ile Ile Pro Lys Phe Gly Lys Phe Ile Gln Asn Glu Asp Gln Pro
    50                  55                  60

Asp Tyr Arg Glu Asp Ala Lys Arg Phe Ile Asn Pro Asn Trp Asp Pro
65                  70                  75                  80

Thr Lys Asn Glu Ile Tyr Glu Tyr Ile Arg Ser Asp Phe Lys Asp Glu
                85                  90                  95

Tyr Leu Asp Leu Glu Asp Glu Asn Asp Ala Trp Tyr Ile Ile Met Thr
            100                 105                 110

Cys Ile Pro Asp His Pro Glu Ser Ala Arg Ile Tyr His Leu Cys Lys
        115                 120                 125

Glu Arg Phe Gly Lys Gln Gln Leu Val Asn Val Ala Asp Lys Pro Asp
    130                 135                 140

Leu Cys Asp Phe Tyr Phe Gly Ala Asn Leu Glu Ile Gly Asp Arg Leu
145                 150                 155                 160

Gln Ile Leu Ile Ser Thr Asn Gly Leu Ser Pro Arg Phe Gly Ala Leu
                165                 170                 175

Val Arg Asp Glu Ile Arg Asn Leu Phe Thr Gln Met Gly Asp Leu Ala
            180                 185                 190

Leu Glu Asp Ala Val Val Lys Leu Gly Glu Leu Arg Arg Gly Ile Arg
        195                 200                 205

Leu Leu Ala Pro Asp Asp Lys Asp Val Lys Tyr Arg Met Asp Trp Ala
    210                 215                 220

Arg Arg Cys Thr Asp Leu Phe Gly Ile Gln His Cys His Asn Ile Asp
225                 230                 235                 240

Val Lys Arg Leu Leu Asp Leu Phe Lys Val Met Phe Gln Glu Gln Asn
                245                 250                 255

Cys Ser Leu Gln Phe Pro Pro Arg Glu Arg Leu Leu Ser Glu Tyr Cys
            260                 265                 270

Ser Ser
```

<210> SEQ ID NO 24
<211> LENGTH: 670
<212> TYPE: PRT
<213> ORGANISM: Arabidopsis thaliana
<220> FEATURE:
<221> NAME/KEY: MISC_FEATURE
<222> LOCATION: (1)..(670)
<223> OTHER INFORMATION: Molybdopterin biosynthesis protein CNX1

<400> SEQUENCE: 24

```
Met Glu Gly Gln Gly Cys Cys Gly Gly Gly Gly Gly Lys Thr Glu Met
1               5                   10                  15

Ile Pro Thr Glu Glu Ala Leu Arg Ile Val Phe Gly Val Ser Lys Arg
            20                  25                  30

Leu Pro Pro Val Ile Val Ser Leu Tyr Glu Ala Leu Gly Lys Val Leu
        35                  40                  45

Ala Glu Asp Ile Arg Ala Pro Asp Pro Leu Pro Pro Tyr Pro Ala Ser
    50                  55                  60

Val Lys Asp Gly Tyr Ala Val Val Ala Ser Asp Gly Pro Gly Glu Tyr
65                  70                  75                  80

Pro Val Ile Thr Glu Ser Arg Ala Gly Asn Asp Gly Leu Gly Val Thr
                85                  90                  95

Val Thr Pro Gly Thr Val Ala Tyr Val Thr Thr Gly Gly Pro Ile Pro
```

-continued

```
            100                 105                 110

Asp Gly Ala Asp Ala Val Val Gln Val Glu Asp Thr Lys Val Ile Gly
        115                 120                 125

Asp Val Ser Thr Glu Ser Lys Arg Val Lys Ile Leu Ile Gln Thr Lys
    130                 135                 140

Lys Gly Thr Asp Ile Arg Arg Val Gly Cys Asp Ile Glu Lys Asp Ala
145                 150                 155                 160

Thr Val Leu Thr Thr Gly Glu Arg Ile Gly Ala Ser Glu Ile Gly Leu
                165                 170                 175

Leu Ala Thr Ala Gly Val Thr Met Val Lys Val Tyr Pro Met Pro Ile
            180                 185                 190

Val Ala Ile Leu Ser Thr Gly Asp Glu Leu Val Glu Pro Thr Ala Gly
        195                 200                 205

Thr Leu Gly Arg Gly Gln Ile Arg Asp Ser Asn Arg Ala Met Leu Val
    210                 215                 220

Ala Ala Val Met Gln Gln Gln Cys Lys Val Val Asp Leu Gly Ile Val
225                 230                 235                 240

Arg Asp Asp Arg Lys Glu Leu Glu Lys Val Leu Asp Glu Ala Val Ser
                245                 250                 255

Ser Gly Val Asp Ile Ile Leu Thr Ser Gly Gly Val Ser Met Gly Asp
            260                 265                 270

Arg Asp Phe Val Lys Pro Leu Leu Glu Glu Lys Gly Lys Val Tyr Phe
        275                 280                 285

Ser Lys Val Leu Met Lys Pro Gly Lys Pro Leu Thr Phe Ala Glu Ile
    290                 295                 300

Arg Ala Lys Pro Thr Glu Ser Met Leu Gly Lys Thr Val Leu Ala Phe
305                 310                 315                 320

Gly Leu Pro Gly Asn Pro Val Ser Cys Leu Val Cys Phe Asn Ile Phe
                325                 330                 335

Val Val Pro Thr Ile Arg Gln Leu Ala Gly Trp Thr Ser Pro His Pro
            340                 345                 350

Leu Arg Val Arg Leu Arg Leu Gln Glu Pro Ile Lys Ser Asp Pro Ile
        355                 360                 365

Arg Pro Glu Phe His Arg Ala Ile Ile Lys Trp Lys Asp Asn Asp Gly
    370                 375                 380

Ser Gly Thr Pro Gly Phe Val Ala Glu Ser Thr Gly His Gln Met Ser
385                 390                 395                 400

Ser Arg Leu Leu Ser Met Arg Ser Ala Asn Ala Leu Leu Glu Leu Pro
                405                 410                 415

Ala Thr Gly Asn Val Leu Ser Ala Gly Ser Ser Val Ser Ala Ile Ile
            420                 425                 430

Val Ser Asp Ile Ser Ala Phe Ser Ile Asp Lys Lys Ala Ser Leu Ser
        435                 440                 445

Glu Pro Gly Ser Ile Arg Lys Glu Lys Lys Tyr Asp Glu Val Pro Gly
    450                 455                 460

Pro Glu Tyr Lys Val Ala Ile Leu Thr Val Ser Asp Thr Val Ser Ala
465                 470                 475                 480

Gly Ala Gly Pro Asp Arg Ser Gly Pro Arg Ala Val Ser Val Val Asp
                485                 490                 495

Ser Ser Ser Glu Lys Leu Gly Gly Ala Lys Val Val Ala Thr Ala Val
            500                 505                 510

Val Pro Asp Glu Val Glu Arg Ile Lys Asp Ile Leu Gln Lys Trp Ser
        515                 520                 525
```

```
Asp Val Asp Glu Met Asp Leu Ile Leu Thr Leu Gly Gly Thr Gly Phe
    530                 535                 540

Thr Pro Arg Asp Val Thr Pro Glu Ala Thr Lys Lys Val Ile Glu Arg
545                 550                 555                 560

Glu Thr Pro Gly Leu Leu Phe Val Met Met Gln Glu Ser Leu Lys Ile
                565                 570                 575

Thr Pro Phe Ala Met Leu Ser Arg Ser Ala Ala Gly Ile Arg Gly Ser
            580                 585                 590

Thr Leu Ile Ile Asn Met Pro Gly Asn Pro Asn Ala Val Ala Glu Cys
        595                 600                 605

Met Glu Ala Leu Leu Pro Ala Leu Lys His Ala Leu Lys Gln Ile Lys
    610                 615                 620

Gly Asp Lys Arg Glu Lys His Pro Lys His Ile Pro His Ala Glu Ala
625                 630                 635                 640

Thr Leu Pro Thr Asp Thr Trp Asp Gln Ser Tyr Lys Ser Ala Tyr Glu
                645                 650                 655

Thr Gly Glu Lys Lys Glu Glu Ala Gly Cys Ser Cys Thr His
            660                 665                 670


<210> SEQ ID NO 25
<211> LENGTH: 390
<212> TYPE: PRT
<213> ORGANISM: Arabidopsis thaliana
<220> FEATURE:
<221> NAME/KEY: MISC_FEATURE
<222> LOCATION: (1)..(390)
<223> OTHER INFORMATION: GTP 3',8-cyclase, mitochondrial CNX2

<400> SEQUENCE: 25

Met Arg Arg Cys Phe Ser Lys Ile Thr Asp Cys His Leu Gly Phe Lys
1               5                   10                  15

Asn Ser Asn Phe Leu Leu Val Gly Ser Glu Val Gly Ser Gly Ser Val
            20                  25                  30

Thr Arg Thr Ile Thr Thr Thr Thr Ser Glu Arg Leu Phe Ser Ser Ser
        35                  40                  45

Tyr Ala Ala His Gln Val Asp Gln Ile Lys Asp Asn Pro Val Ser Asp
    50                  55                  60

Met Leu Ile Asp Lys Phe Gly Arg Leu His Thr Tyr Leu Arg Ile Ser
65                  70                  75                  80

Leu Thr Glu Arg Cys Asn Leu Arg Cys Gln Tyr Cys Met Pro Ser Glu
                85                  90                  95

Gly Val Glu Leu Thr Pro Lys Pro Gln Leu Leu Ser Gln Ser Glu Ile
            100                 105                 110

Val Arg Leu Ala Gly Leu Phe Val Ser Ala Gly Val Asn Lys Ile Arg
        115                 120                 125

Leu Thr Gly Gly Glu Pro Thr Val Arg Lys Asp Ile Glu Glu Ile Cys
    130                 135                 140

Leu Gln Leu Ser Ser Leu Lys Gly Leu Lys Asn Leu Ala Ile Thr Thr
145                 150                 155                 160

Asn Gly Ile Thr Leu Ala Lys Lys Leu Pro Arg Leu Lys Glu Cys Gly
                165                 170                 175

Leu Asp Ser Leu Asn Ile Ser Leu Asp Thr Leu Val Pro Ala Lys Phe
            180                 185                 190

Glu Phe Leu Thr Arg Arg Lys Gly His Asp Arg Val Met Lys Ser Ile
        195                 200                 205
```

Asp Thr Ala Ile Glu Leu Gly Tyr Asn Pro Val Lys Val Asn Cys Val
    210                 215                 220

Ile Met Arg Gly Leu Asn Asp Asp Glu Ile Cys Asp Phe Val Glu Leu
225                 230                 235                 240

Thr Arg Asp Lys Pro Ile Asn Val Arg Phe Ile Glu Phe Met Pro Phe
                245                 250                 255

Asp Gly Asn Val Trp Asn Val Lys Lys Leu Val Pro Tyr Ala Glu Val
            260                 265                 270

Met Asp Lys Val Val Lys Arg Phe Pro Ser Ile Lys Arg Met Gln Asp
        275                 280                 285

His Pro Thr Glu Thr Ala Lys Asn Phe Thr Ile Asp Gly His Cys Gly
    290                 295                 300

Ser Val Ser Phe Ile Thr Ser Met Thr Glu His Phe Cys Ala Gly Cys
305                 310                 315                 320

Asn Arg Leu Arg Leu Leu Ala Asp Gly Asn Phe Lys Val Cys Leu Phe
                325                 330                 335

Gly Pro Ser Glu Val Ser Leu Arg Asp Pro Leu Arg Ser Gly Ala Asp
            340                 345                 350

Asp Glu Ala Leu Arg Glu Ile Ile Gly Ala Ala Val Lys Arg Lys Lys
        355                 360                 365

Ala Ala His Ala Gly Met Leu Asp Ile Ala Lys Thr Ala Asn Arg Pro
    370                 375                 380

Met Ile His Ile Gly Gly
385                 390

<210> SEQ ID NO 26
<211> LENGTH: 270
<212> TYPE: PRT
<213> ORGANISM: Arabidopsis thaliana
<220> FEATURE:
<221> NAME/KEY: MISC_FEATURE
<222> LOCATION: (1)..(270)
<223> OTHER INFORMATION: Cyclic pyranopterin monophosphate synthase, mitochondrial

<400> SEQUENCE: 26

Met Ile Ser Thr Leu Arg Arg Ala Val Phe Leu Arg Arg Phe Pro Ala
1               5                   10                  15

Val Val Ser Pro Ile Lys Arg Ala Phe Ser Ser Arg Ile Asp Asp Glu
            20                  25                  30

Phe Asp Pro Gln Ile Met Asn Ile Asn Glu Leu Asn Gln Glu Met Gln
        35                  40                  45

Ser Ile Phe Gly Gln Glu Pro Ser Pro Asp Gly Pro Gly Thr Met Asp
    50                  55                  60

Phe Ser Glu Leu Lys Ser Ser Lys Ile Glu Pro Leu Arg Ser Lys Asn
65                  70                  75                  80

Ile Asp Phe Arg Gln Gln Ile Glu Tyr His Lys Ser Thr His Ser Ser
                85                  90                  95

Lys Asn Asp Ser Gln Ala Ile Glu Gln Tyr Ala Lys Val Ala Ser Asp
            100                 105                 110

Met Ser Lys Leu Thr His Val Gly Ile Ala Gly Glu Ala Gln Met Val
        115                 120                 125

Asp Val Ser Ser Lys Asp Asn Ser Lys Arg Thr Ala Leu Ala Cys Cys
    130                 135                 140

Lys Val Ile Leu Gly Lys Arg Val Phe Asp Leu Val Leu Ala Asn Gln
145                 150                 155                 160

```
Met Gly Lys Gly Asp Val Leu Gly Val Ala Lys Ile Ala Gly Ile Asn
            165                 170                 175

Gly Ala Lys Gln Thr Ser Ser Leu Ile Pro Leu Cys His Asn Ile Ala
            180                 185                 190

Leu Thr His Val Arg Val Asp Leu Arg Leu Asn Pro Glu Asp Phe Ser
        195                 200                 205

Val Asp Ile Glu Gly Glu Ala Ser Cys Thr Gly Lys Thr Gly Val Glu
    210                 215                 220

Met Glu Ala Met Thr Ala Val Ser Val Ala Gly Leu Thr Val Tyr Asp
225                 230                 235                 240

Met Cys Lys Ala Ala Ser Lys Asp Ile Ser Ile Thr Asp Val Arg Leu
            245                 250                 255

Glu Arg Lys Thr Gly Gly Lys Ser Gly Ser Trp Ser Arg Leu
            260                 265                 270


<210> SEQ ID NO 27
<211> LENGTH: 464
<212> TYPE: PRT
<213> ORGANISM: Arabidopsis thaliana
<220> FEATURE:
<221> NAME/KEY: MISC_FEATURE
<222> LOCATION: (1)..(464)
<223> OTHER INFORMATION: Adenylyltransferase and sulfurtransferase MOCS3

<400> SEQUENCE: 27

Met Met Ser Asn Gly Gly Asp Ser Ser Glu Ile Val Arg Glu Leu Glu
1               5                   10                  15

Glu Leu Lys Leu Lys Lys Ala Glu Ile Glu His Arg Ile Ser Thr Leu
            20                  25                  30

Glu Ala Lys Leu Gln Asp Thr Ala Ala Val Glu Leu Tyr Asp Ala Val
        35                  40                  45

Ser Asn Gly Asp Ser Tyr Leu Thr Ala Pro Glu Leu Glu His Gly Leu
    50                  55                  60

Ser Pro Asp Gln Ile Tyr Arg Tyr Ser Arg Gln Leu Leu Leu Pro Ser
65                  70                  75                  80

Phe Ala Val Glu Gly Gln Ser Asn Leu Leu Lys Ser Ser Val Leu Val
                85                  90                  95

Ile Gly Ala Gly Gly Leu Gly Ser Pro Ala Leu Leu Tyr Leu Ala Ala
            100                 105                 110

Cys Gly Val Gly Gln Leu Gly Ile Ile Asp His Asp Val Val Glu Leu
        115                 120                 125

Asn Asn Met His Arg Gln Ile Ile His Thr Glu Ala Phe Ile Gly His
    130                 135                 140

Pro Lys Val Lys Ser Ala Ala Ala Ala Cys Arg Ser Ile Asn Ser Thr
145                 150                 155                 160

Ile Lys Val Asp Glu Tyr Val Glu Ala Leu Arg Thr Ser Asn Ala Leu
                165                 170                 175

Glu Ile Leu Ser Gln Tyr Asp Ile Ile Val Asp Ala Thr Asp Asn Pro
            180                 185                 190

Pro Ser Arg Tyr Met Ile Ser Asp Cys Cys Val Leu Leu Gly Lys Pro
        195                 200                 205

Leu Val Ser Gly Ala Ala Leu Gly Met Glu Gly Gln Leu Thr Val Tyr
    210                 215                 220

Asn His Asn Gly Gly Pro Cys Tyr Arg Cys Leu Phe Pro Thr Pro Pro
225                 230                 235                 240

Pro Thr Ser Ala Cys Gln Arg Cys Ser Asp Ser Gly Val Leu Gly Val
```

```
                245                 250                 255

Val Pro Gly Val Ile Gly Cys Leu Gln Ala Leu Glu Thr Ile Lys Leu
            260                 265                 270

Ala Ser Leu Val Gly Glu Pro Leu Ser Glu Arg Met Leu Leu Phe Asp
        275                 280                 285

Ala Leu Ser Ala Arg Met Arg Ile Val Lys Ile Arg Gly Arg Ser Ser
    290                 295                 300

Gln Cys Thr Val Cys Gly Asp Asn Ser Ser Phe Asn Lys Gln Thr Phe
305                 310                 315                 320

Lys Asp Phe Asp Tyr Glu Asp Phe Thr Gln Phe Pro Leu Phe Ala Gly
                325                 330                 335

Pro Leu Asn Leu Leu Pro Ala Glu Ser Arg Ile Ser Ser Lys Glu Phe
            340                 345                 350

Lys Glu Ile Leu Gln Lys Lys Glu Gln His Val Leu Leu Asp Val Arg
        355                 360                 365

Pro Ser His His Tyr Lys Ile Val Ser Leu Pro Asp Ser Leu Asn Ile
    370                 375                 380

Pro Leu Ala Asn Leu Glu Thr Arg Leu Asn Glu Leu Thr Ser Ala Leu
385                 390                 395                 400

Lys Glu Lys Gly Asn Gly His Ala Asn Thr Glu Ser Cys Thr Asn Pro
                405                 410                 415

Ser Val Phe Val Val Cys Arg Arg Gly Asn Asp Ser Gln Arg Ala Val
            420                 425                 430

Gln Tyr Leu Arg Glu Ser Gly Phe Asp Ser Ala Lys Asp Ile Ile Gly
        435                 440                 445

Gly Leu Glu Ala Trp Ala Ala Asn Val Asn Pro Asn Phe Pro Thr Tyr
    450                 455                 460


<210> SEQ ID NO 28
<211> LENGTH: 198
<212> TYPE: PRT
<213> ORGANISM: Arabidopsis thaliana
<220> FEATURE:
<221> NAME/KEY: MISC_FEATURE
<222> LOCATION: (1)..(198)
<223> OTHER INFORMATION: Molybdopterin synthase catalytic subunit

<400> SEQUENCE: 28

Met Ser Ala Glu Glu Lys Asn Leu Ile Glu Ile Leu Glu Glu Gly His
1               5                   10                  15

Lys Val Asp Val Val Lys Tyr Ile Asp Tyr Val Ser Ala Pro Gln Ala
            20                  25                  30

Gly Ala Ile Ala Thr Phe Ser Gly Thr Thr Arg Asp Met Phe Glu Gly
        35                  40                  45

Lys Thr Val Leu Glu Leu Arg Tyr Glu Ala Tyr Val Pro Met Ala Thr
    50                  55                  60

Arg Cys Leu Ser Ser Ile Cys Thr Thr Ala Arg Ser Thr Trp Asp Ile
65                  70                  75                  80

His Lys Ile Ala Val Ala His Arg Leu Gly Pro Val Pro Val Gly Glu
                85                  90                  95

Thr Ser Val Leu Ile Ala Val Ser Ser Val His Arg Ala Asp Gly Leu
            100                 105                 110

Asp Ala Cys Lys Phe Leu Ile Asp Glu Leu Lys Ala Ser Val Pro Ile
        115                 120                 125

Trp Lys Lys Glu Val Tyr Thr Asn Gly Glu Ile Trp Lys Glu Asn Ser
    130                 135                 140
```

-continued

```
Glu Phe Met Glu Lys Arg Leu Glu Leu Ala Glu Lys Arg Asp Ser Ile
145                 150                 155                 160

Val Lys Lys Thr Val Val Glu Glu His Arg Arg Arg Gly Cys Cys Gly
                165                 170                 175

Ser Lys Val Arg Val Glu Glu Asp Glu Glu His Lys Asp Ile Thr Gly
            180                 185                 190

Asp Asn Lys Ser Ser Ser
        195


<210> SEQ ID NO 29
<211> LENGTH: 96
<212> TYPE: PRT
<213> ORGANISM: Arabidopsis thaliana
<220> FEATURE:
<221> NAME/KEY: MISC_FEATURE
<222> LOCATION: (1)..(96)
<223> OTHER INFORMATION: Molybdopterin synthase sulfur carrier subunit

<400> SEQUENCE: 29

Met Asp Lys Glu Val Thr Lys Ile Glu Ser Asp Asp Thr Ser Ser Val
1               5                   10                  15

Glu Ile Lys Val Leu Leu Phe Ala Arg Ala Arg Glu Leu Thr Gly Val
            20                  25                  30

Pro Asp Leu Thr Leu Lys Met Pro Ser Gly Ser Thr Thr Gln Lys Cys
        35                  40                  45

Leu Asp Glu Leu Val Leu Lys Phe Pro Ser Leu Glu Glu Val Arg Ser
    50                  55                  60

Cys Val Val Leu Ala Leu Asn Glu Glu Tyr Thr Thr Asp Ser Ala Ile
65                  70                  75                  80

Val Gln His Arg Asp Glu Leu Ala Ile Ile Pro Pro Ile Ser Gly Gly
                85                  90                  95
```